(12) United States Patent
Finkelmeier et al.

(10) Patent No.: US 8,858,960 B2
(45) Date of Patent: Oct. 14, 2014

(54) METHOD OF PRODUCING A PHARMACEUTICAL PRODUCT

(75) Inventors: Steven D. Finkelmeier, Collegeville, PA (US); Robert Glinecke, Collegeville, PA (US); Luigi Martini, Harlow (GB)

(73) Assignee: GlaxoSmithKline, LLC, Philadelphia, PA (US)

( * ) Notice: Subject to any disclaimer, the term of this patent is extended or adjusted under 35 U.S.C. 154(b) by 936 days.

(21) Appl. No.: 11/719,679

(22) PCT Filed: Nov. 18, 2005

(86) PCT No.: PCT/US2005/042216
§ 371 (c)(1),
(2), (4) Date: May 18, 2007

(87) PCT Pub. No.: WO2006/055928
PCT Pub. Date: May 26, 2006

(65) Prior Publication Data
US 2009/0155315 A1    Jun. 18, 2009

Related U.S. Application Data

(60) Provisional application No. 60/661,552, filed on Mar. 14, 2005.

(51) Int. Cl.
*A61J 3/06* (2006.01)
*A61K 9/20* (2006.01)
*A61J 3/10* (2006.01)
*A61K 9/24* (2006.01)

(52) U.S. Cl.
CPC .................. *A61J 3/10* (2013.01); *A61K 9/2072* (2013.01); *A61J 3/06* (2013.01); *A61K 9/2095* (2013.01); *A61K 9/2086* (2013.01); *A61K 9/209* (2013.01)
USPC .......................................... 424/400; 264/241

(58) Field of Classification Search
None
See application file for complete search history.

(56) References Cited

U.S. PATENT DOCUMENTS

| 3,547,682 | A |   | 12/1970 | Erb |
|---|---|---|---|---|
| 3,809,289 | A |   | 5/1974 | Komendowski |
| 4,028,024 | A |   | 6/1977 | Moreland ................ 425/133.1 |
| 4,425,181 | A |   | 1/1984 | Bahr et al. |
| 4,571,924 | A |   | 2/1986 | Bahrani |
| 4,738,817 | A | * | 4/1988 | Wittwer et al. .......... 264/328.14 |
| 4,827,780 | A |   | 5/1989 | Sarrine et al. |
| 4,996,061 | A |   | 2/1991 | Webb et al. .................. 424/475 |
| 5,277,341 | A |   | 1/1994 | Privas |
| 5,348,062 | A |   | 9/1994 | Hartzell et al. |
| 5,360,795 | A | * | 11/1994 | Townsend et al. ............... 514/43 |
| 5,369,940 | A |   | 12/1994 | Solomon |
| 2,714,861 | A |   | 8/1995 | Castronuovo |
| 5,443,459 | A |   | 8/1995 | Wong et al. |
| 5,460,827 | A |   | 10/1995 | Sanderson et al. |
| 5,508,040 | A |   | 4/1996 | Chen |
| 5,609,010 | A |   | 3/1997 | Sauter |
| 5,824,338 | A |   | 10/1998 | Jacobs et al. |
| 5,966,910 | A |   | 10/1999 | Ribani et al. |
| 6,010,706 | A |   | 1/2000 | Candau et al. |
| 6,108,030 | A |   | 8/2000 | Yamamoto et al. |
| 6,126,767 | A |   | 10/2000 | Smith et al. |
| 6,170,152 | B1 |   | 1/2001 | Ohta et al. |
| 6,561,977 | B2 |   | 5/2003 | Williams et al. |
| 6,591,585 | B2 |   | 7/2003 | Stolz |
| 6,772,026 | B2 |   | 8/2004 | Bradbury et al. |
| 6,799,413 | B2 |   | 10/2004 | Aylward |
| 2003/0186828 | A1 | * | 10/2003 | Holderbaum et al. ........ 510/224 |
| 2004/0181528 | A1 |   | 9/2004 | Tirinato et al. |
| 2004/0200043 | A1 |   | 10/2004 | Wong et al. |
| 2005/0175696 | A1 |   | 8/2005 | Edgren et al. |
| 2006/0000470 | A1 |   | 1/2006 | Clarke et al. |
| 2006/0001866 | A1 |   | 1/2006 | Clarke et al. |
| 2006/0002594 | A1 |   | 1/2006 | Clarke et al. |
| 2006/0002986 | A1 |   | 1/2006 | Clarke et al. |
| 2006/0016830 | A1 |   | 1/2006 | Clarke et al. |
| 2006/0017916 | A1 |   | 1/2006 | Clarke et al. |
| 2006/0141001 | A1 |   | 6/2006 | Finkelmeier et al. |
| 2007/0193225 | A1 |   | 8/2007 | Bailey et al. |
| 2008/0306622 | A1 |   | 12/2008 | Bailey et al. |
| 2009/0149507 | A1 |   | 6/2009 | Kirsh et al. |

FOREIGN PATENT DOCUMENTS

| ES | 2173891 |   | 11/2002 |
|---|---|---|---|
| JP | 62133960 |   | 6/1987 |
| JP | 069375 |   | 1/1994 |
| JP | 6009375 | * | 1/1994 |
| JP | 072649 |   | 1/1995 |
| JP | 08501544 |   | 2/1996 |
| JP | 2003505498 |   | 2/2003 |
| JP | 2004522746 |   | 7/2004 |
| RU | 767415 |   | 9/1980 |

(Continued)

OTHER PUBLICATIONS

Written Opinion for Singapore Application No. 2008-03605-5 dated Jan. 4, 2010.
International Search Report of PCT/US2006/061032 corresponding to WO 2007/062323.
International Preliminary Report on Patentability (IPER) dated Nov. 17, 2010 for PCT/US2006/061032.
Colombian Office Action dated May 4, 2011 for application No. 07-050.152.
Japanese Office Action dated Nov. 15, 2011 for Japanese application No. 2007-543377.
Colombian Office Action dated Jan. 5, 2012 for Colombian application No. 07-050.152.
Israeli Office Action dated Oct. 14, 2011 for Israeli application No. 191474.

(Continued)

*Primary Examiner* — Suzanne Ziska
(74) *Attorney, Agent, or Firm* — Ohlandt, Greeley, Ruggiero, Perle, LLP

(57) ABSTRACT

A pharmaceutical and pharmaceutical-like product is provided. The product provides a plurality of components having active agents that are delivered in a single delivery entity or vehicle. The product allows for selective control of the release rates of each of the active agents while still being delivered in a single product.

17 Claims, 33 Drawing Sheets

(56) References Cited

FOREIGN PATENT DOCUMENTS

| WO | 2001/08666 | | 2/2001 | |
| WO | WO 01/08666 | * | 2/2001 | ............... A61J 3/07 |
| WO | WO 02/085332 | | 10/2002 | |
| WO | 2006055928 | | 5/2006 | |
| WO | 2007/062323 | | 5/2007 | |

OTHER PUBLICATIONS

Philippine Office Action dated Dec. 3, 2011 for Philippine application No. 12007501057.
Japanese Office Action (with English translation) dated Jun. 12, 2012 for Japanese application No. 2007-543377.
Canadian Office Action dated Jun. 21, 2012 for Canadian application No. 2,630,248.
Canadian Office Action dated Mar. 7, 2012 for Canadian application No. 2,588,418.
Indonesian Office Action dated Aug. 10, 2012 for Indonesian application No. W-00200701538.
Colombian Office Action dated May 17, 2013 for Colombian application No. 07050.152.
Mexican Office Action dated Apr. 10, 2013 for Mexican application No. MX/A/2007/005991.
Canadian Office Action dated Jul. 4, 2013 for Canadian application No. 2,630,248.
Mexican Office Action dated Jul. 4, 2013 for Mexican application No. MX/A/2008/003696.
Official Action for Russian Application No. 2007122763/15(024795) dated Oct. 9, 2009 V.I. Chueshov; "*Industrial Technology of Medicaments*" ed.; 2002; NFAU Publishers; pp. 406-408.
Japanese Office Action dated Feb. 18, 2014 for Japanese application No. 2012-226155.

* cited by examiner

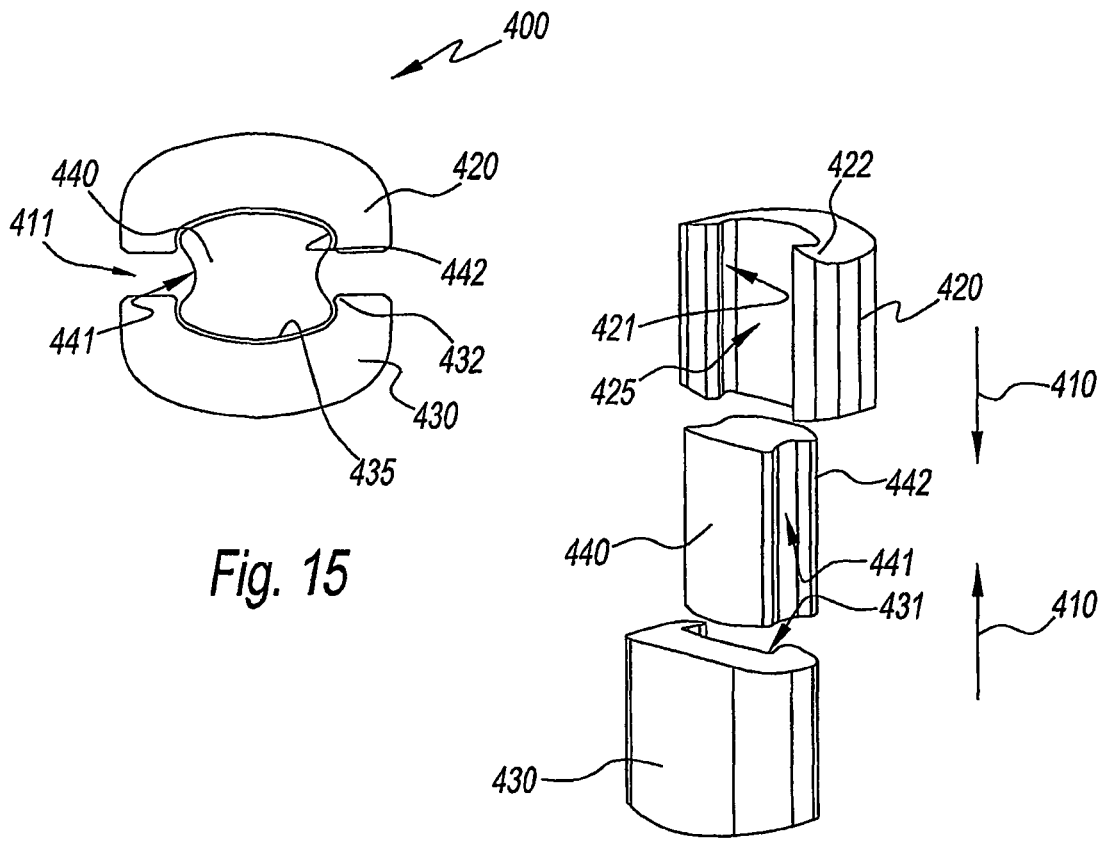
Fig. 15
Fig. 16
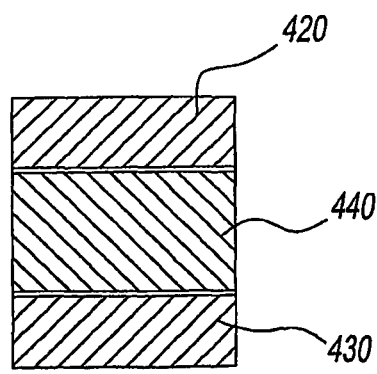
Fig. 17

SECTION A-A

SECTION B-B

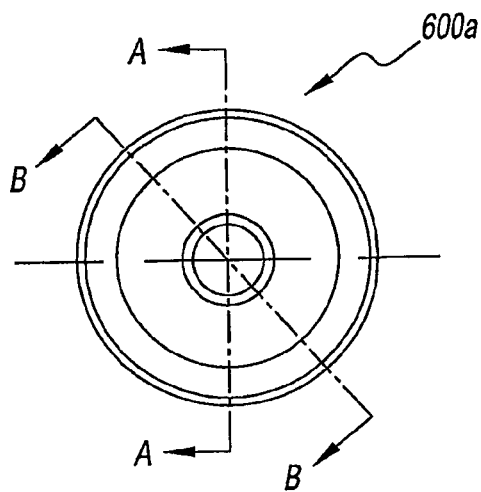
Fig. 31a
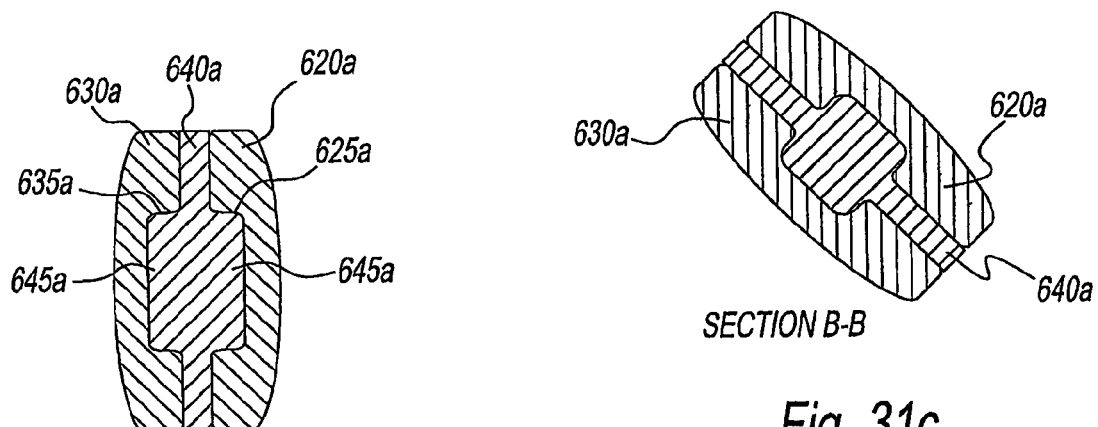
SECTION A-A
Fig. 31b
SECTION B-B
Fig. 31c

SECTION A-A

SECTION B-B

SECTION A-A

SECTION A-A

SECTION B-B

SECTION A-A

SECTION B-B

SECTION A-A

SECTION B-B

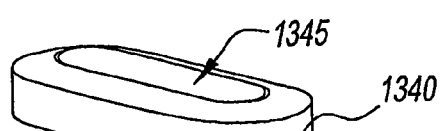
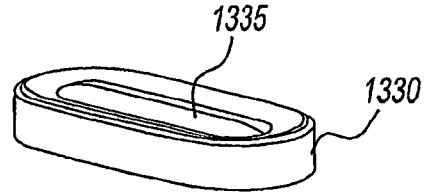
Fig. 54
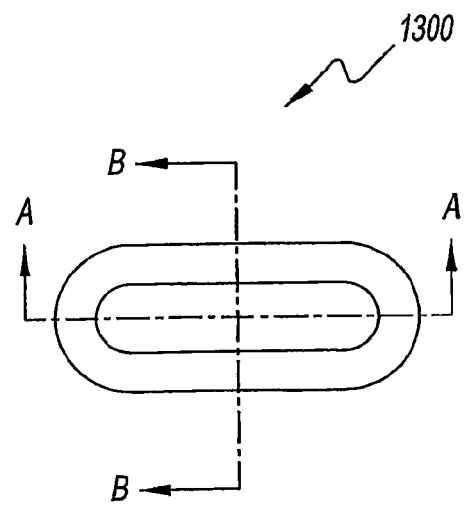
Fig. 55
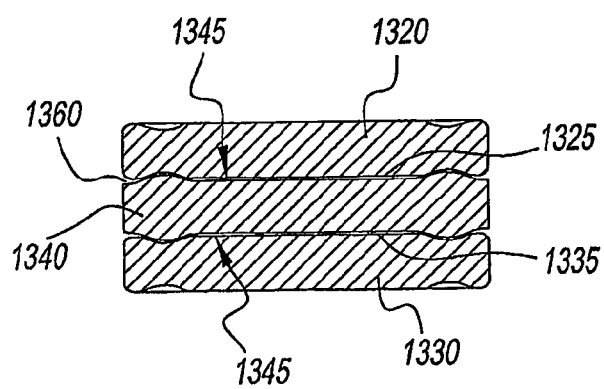
Fig. 56
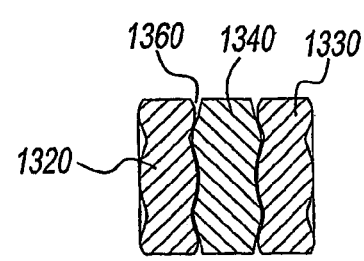
Fig. 57

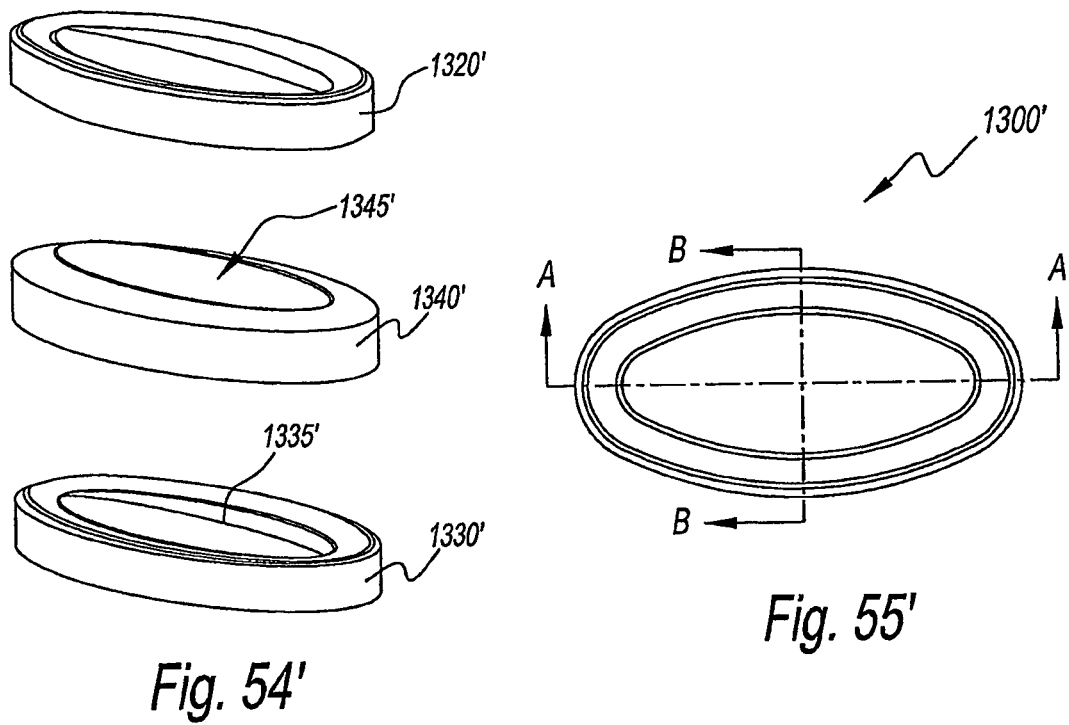
Fig. 54'
Fig. 55'
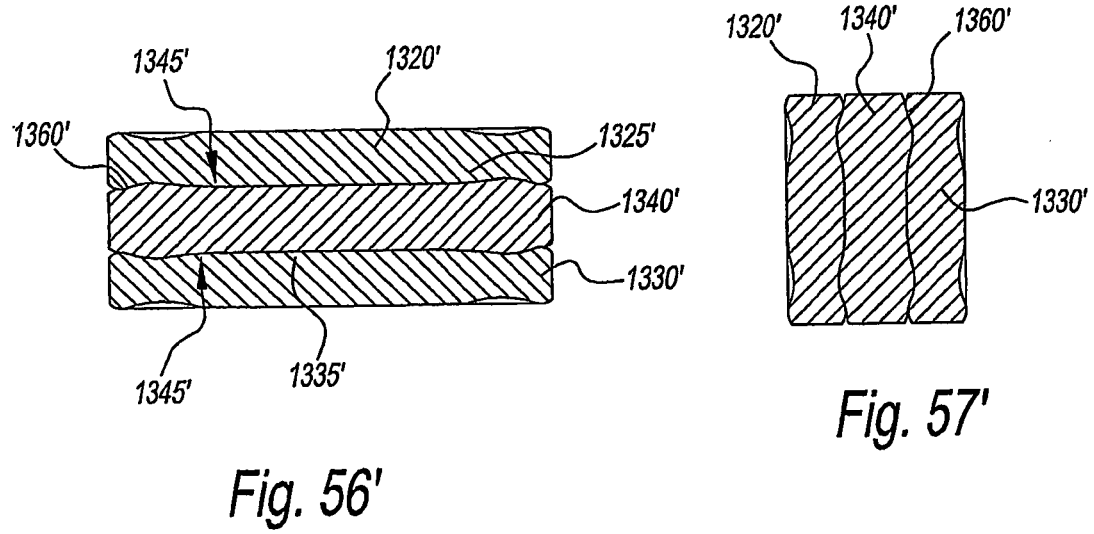
Fig. 56'
Fig. 57'

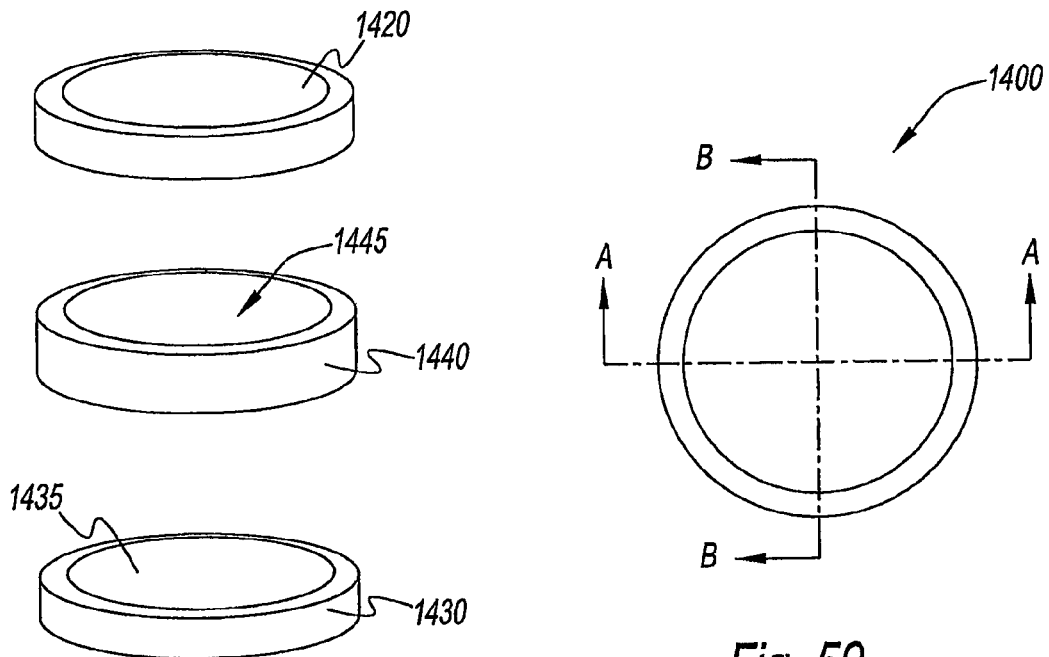
Fig. 58
Fig. 59
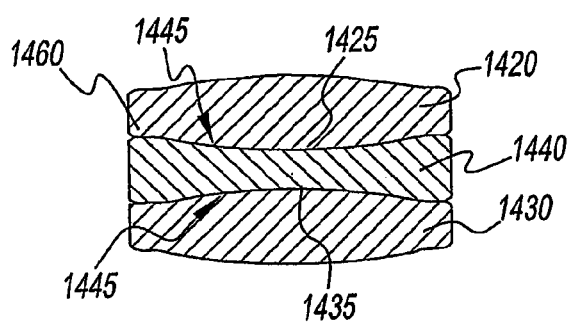
SECTION A-A
Fig. 60
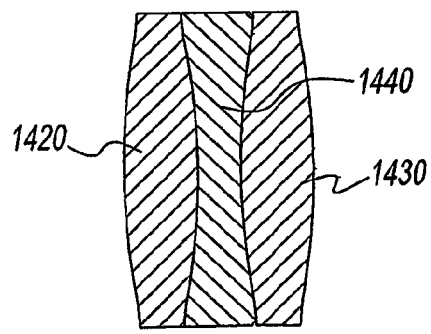
SECTION A-A
Fig. 61

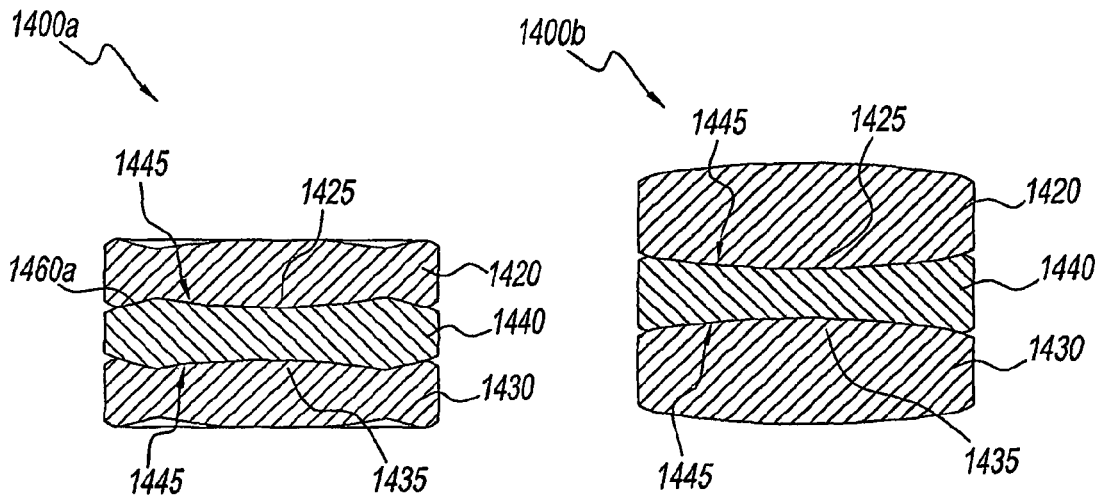
Fig. 61a
Fig. 61b
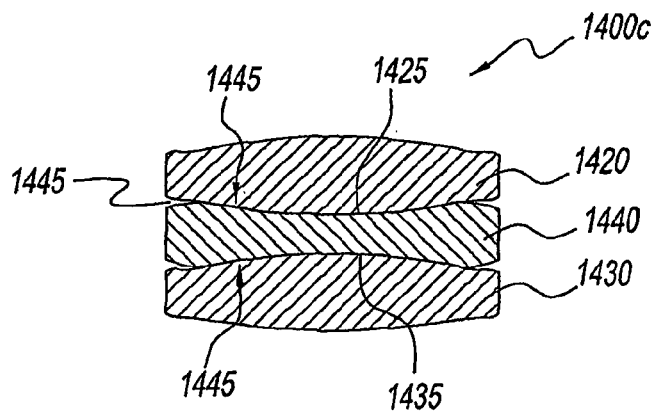
Fig. 61c

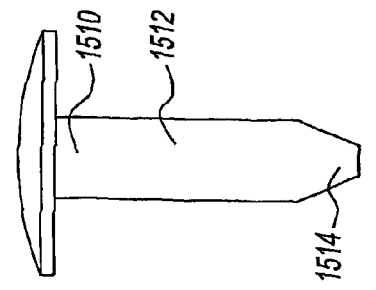
Fig. 62
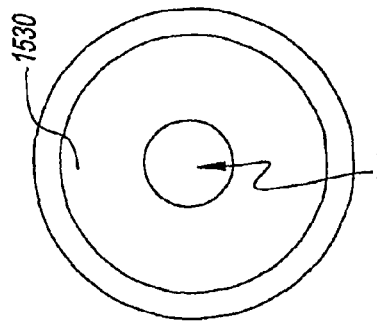
Fig. 63
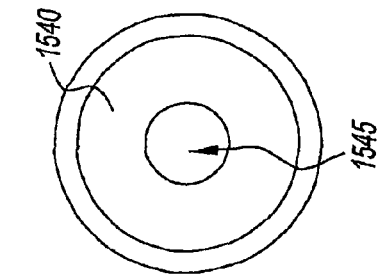
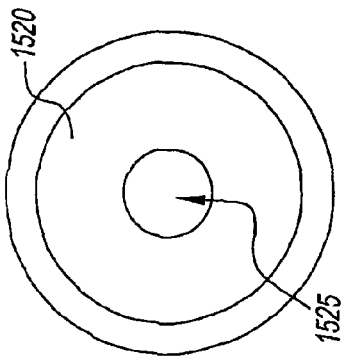
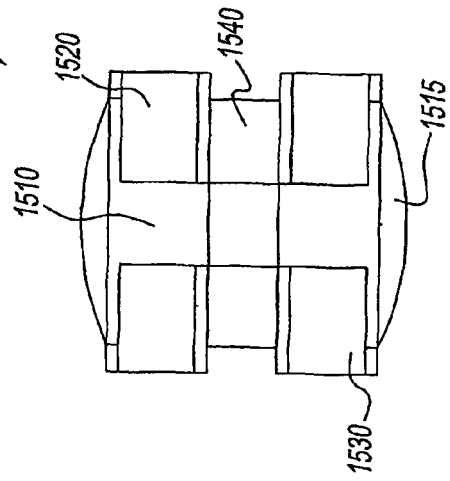
Fig. 65
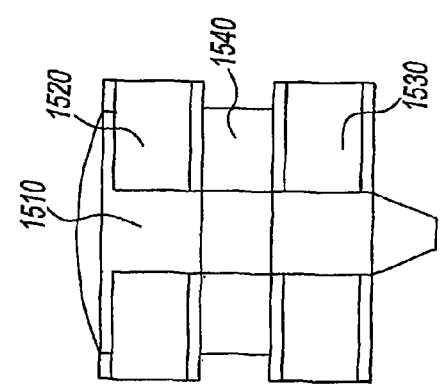
Fig. 64
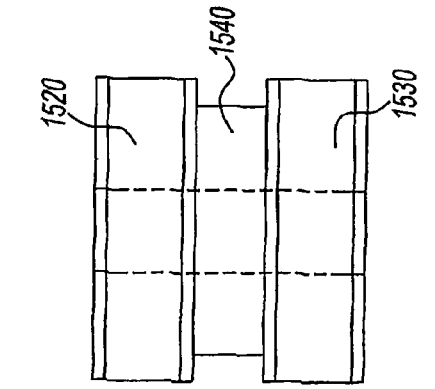

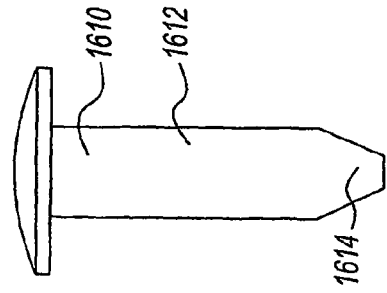
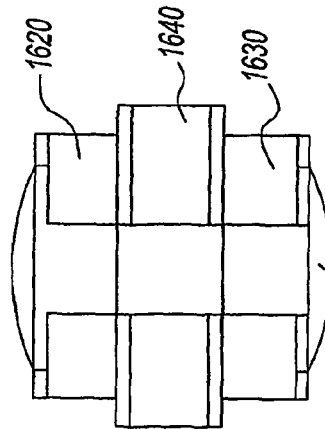
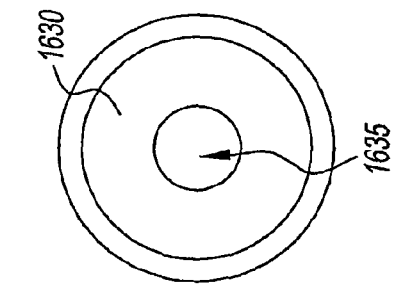
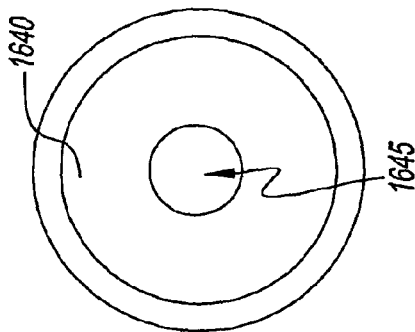
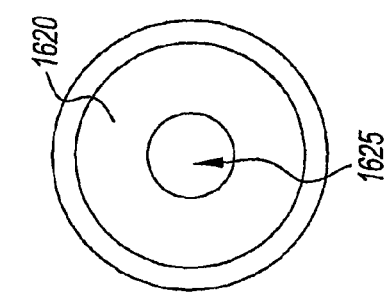

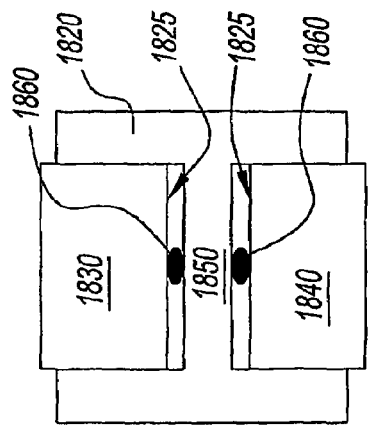
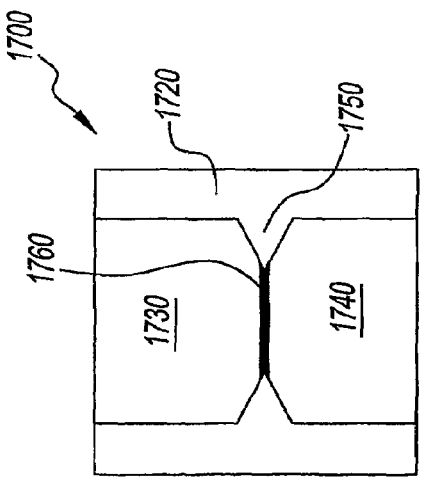
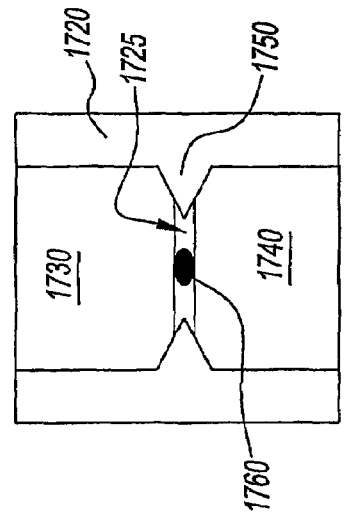
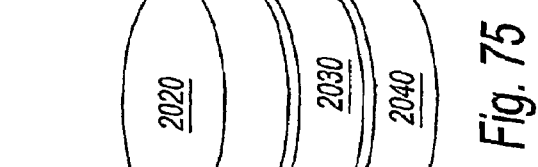
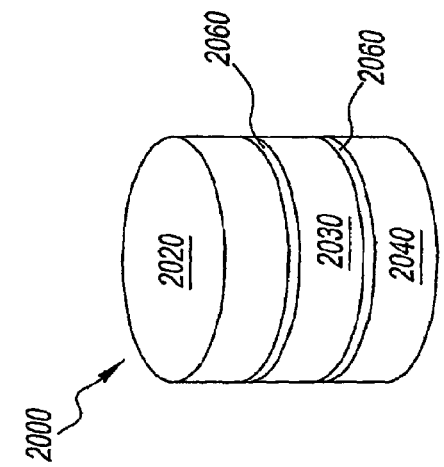
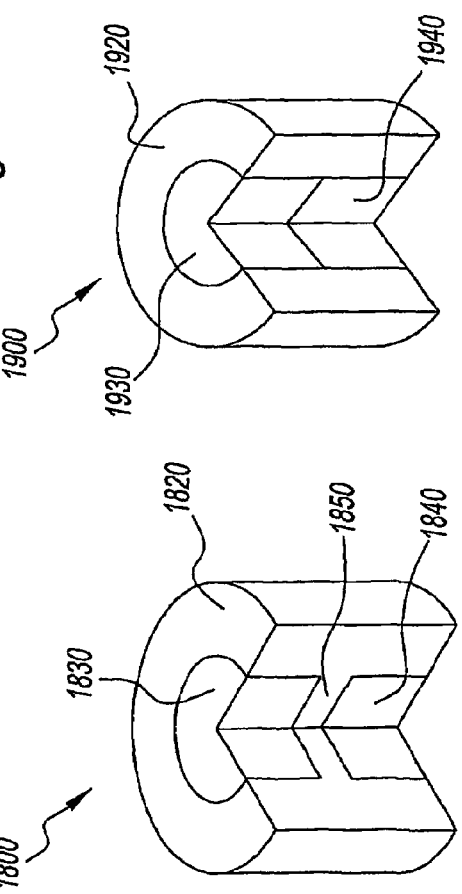

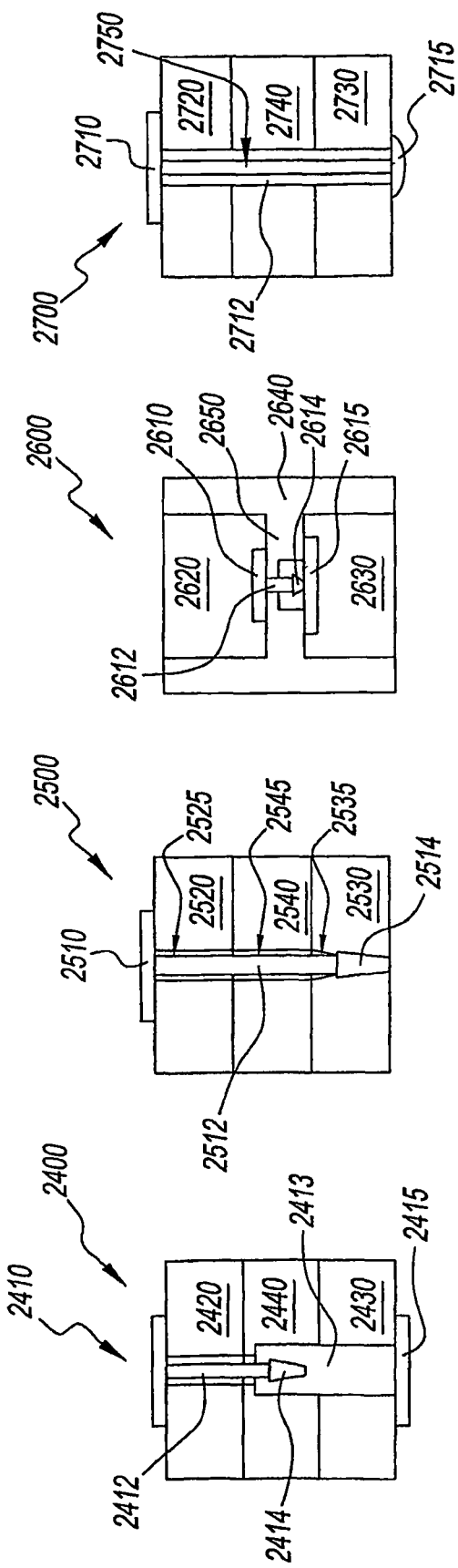

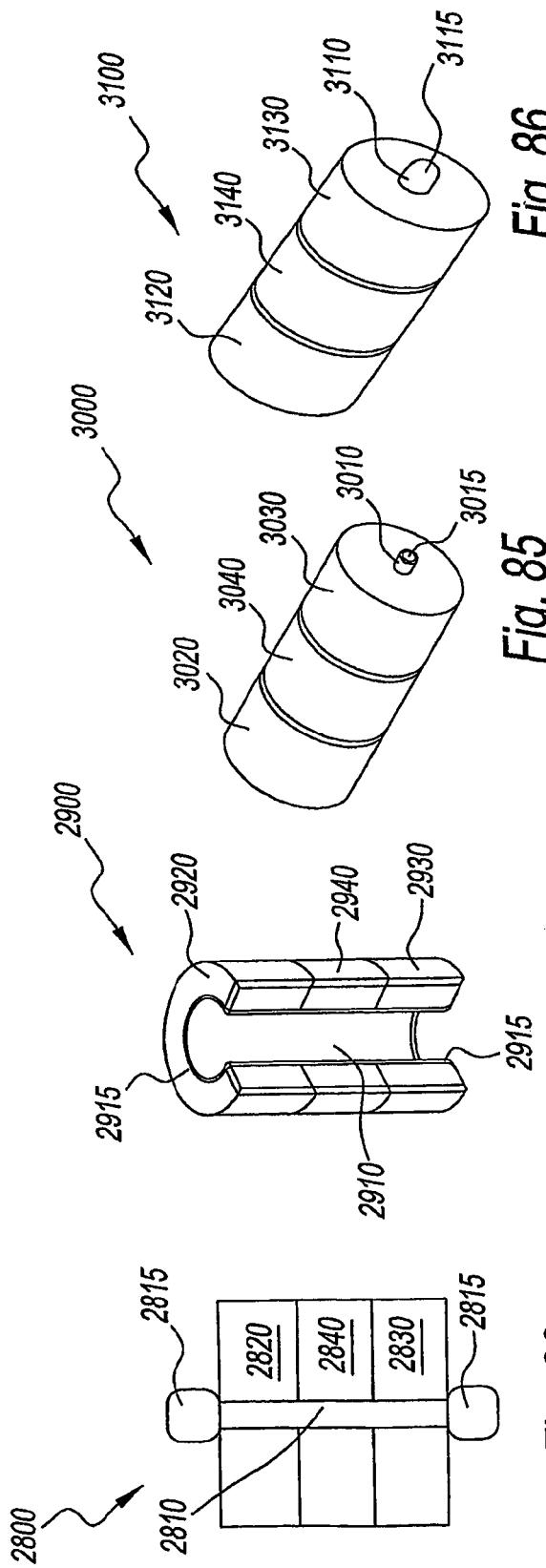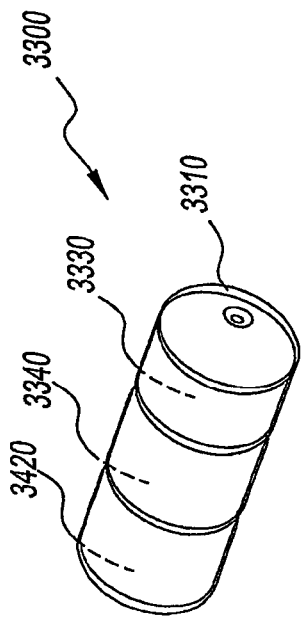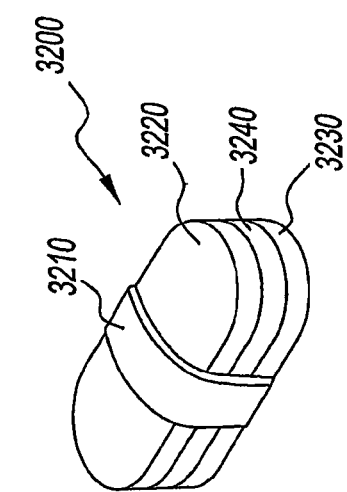

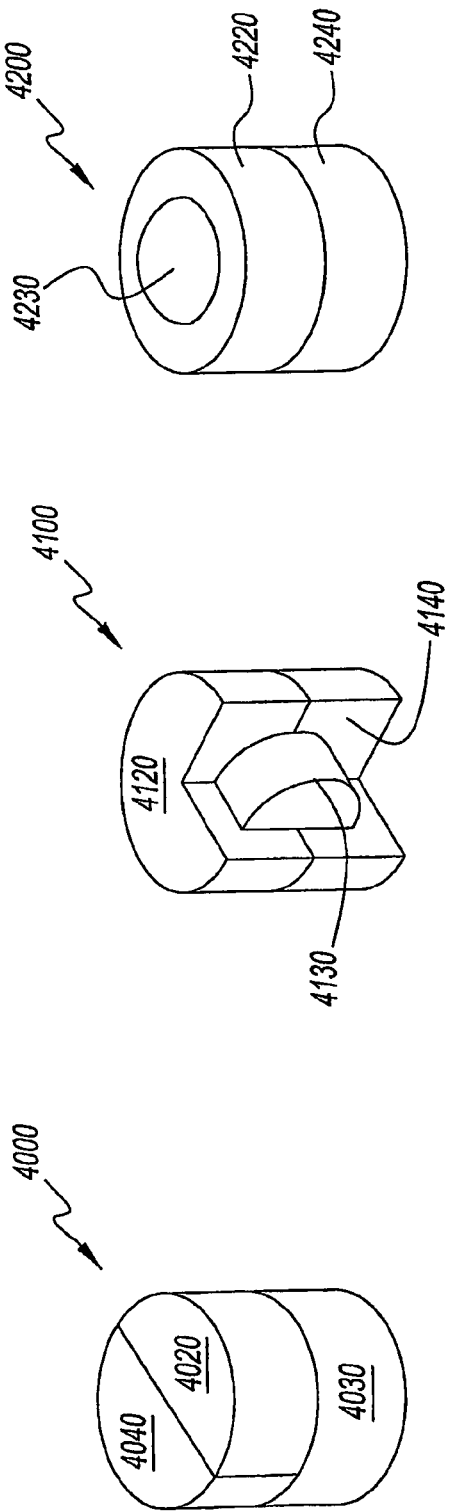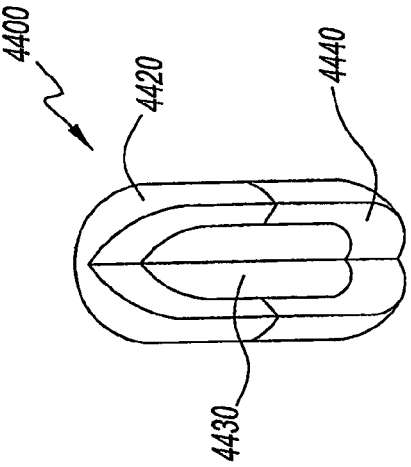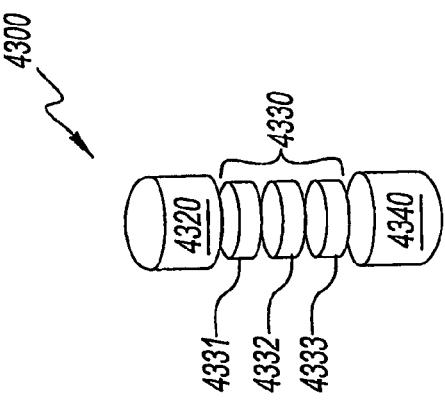

METHOD OF PRODUCING A PHARMACEUTICAL PRODUCT

RELATED APPLICATIONS

This application is related to, and claims priority in U.S. Provisional Application Ser. No. 60/661,552, filed Mar. 14, 2005, and U.S. Provisional Application Ser. No. 60/626,828, filed Nov. 19, 2004, the disclosures of which are incorporated herein by reference.

BACKGROUND OF THE INVENTION

1. Field of the Invention

The present invention relates to pharmaceutical and pharmaceutical-like products. More particularly, the present invention relates to the delivery of an active agent in a pharmaceutical and pharmaceutical-like product.

2. Description of Related Art

The delivery of active agents or medicines can be problematic because of the displeasure of swallowing or otherwise taking the medications. This is particularly true where a plurality of medications must be taken.

Contemporary methods of delivering active agents include tablets and capsules. Tablet manufacturing includes wet granulation or direct compression to add the active ingredient into the tablet ingredients. After mixing to achieve homogeneity, the tablets are formed in the desired shape.

Contemporary capsule manufacturing includes inserting an active agent, typically in powder or pellet form, into a capsule, e.g., a hard capsule made from gelatin or starch, which is then sealed, such as through application of a second capsule shell, an additional outer coating, and additionally contain a banding.

These contemporary delivery structures or vehicles suffer from the drawback of being limited to the use of compatible active agents. These vehicles are also limited to a selected release rate for the active agent or agents.

Accordingly, there is a need for a pharmaceutical product and a process for manufacturing a pharmaceutical product that eliminates these drawbacks of the contemporary pharmaceutical delivery structure or vehicle.

SUMMARY OF THE INVENTION

It is an object of the present invention to provide pharmaceutical and/or pharmaceutical-like products.

It is another object of the present invention to provide a process for making such pharmaceutical and/or pharmaceutical-like products.

It is a further object of the present invention to provide such products and their manufacturing process that allow for delivery of a plurality of active agents.

It is still a further object of the present invention to provide such products and their manufacturing process that allow for greater selectivity of release rates for multiple active agents.

These and other objects and advantages of the present invention are provided by a plurality of components that are interlocked into a single delivery entity or vehicle. Sealing coats can also be used with the different components to further provide for control of the release rates of each of the different components.

Other and further objects, advantages and features of the present invention will be understood by reference to the following:

BRIEF DESCRIPTION OF THE DRAWINGS

FIG. 8a is an exploded view of an alternative embodiment the pharmaceutical product of FIG. 1;

FIG. 8b is a cross-sectional view of the pharmaceutical product of FIG. 8a;

FIG. 15 is a plan view of a seventh embodiment of a pharmaceutical product of the present invention;

FIG. 16 is an exploded perspective view of the pharmaceutical product of FIG. 15;

FIG. 17 is a cross-sectional view of the pharmaceutical product of FIG. 15;

FIG. 31a is a plan view of an alternative embodiment of the pharmaceutical product of FIG. 28;

FIG. 31b is a first cross-sectional view of the pharmaceutical product of FIG. 31a;

FIG. 31c is a second cross-sectional view of the pharmaceutical product of FIG. 31a;

FIG. 39b is a cross-sectional view of the pharmaceutical product of FIG. 39a;

FIG. 54 is an exploded perspective view of a twentieth embodiment of a pharmaceutical product of the present invention;

FIG. 55 is a plan view of the pharmaceutical product of FIG. 54;

FIG. 56 is a first cross-sectional view of the pharmaceutical product of FIG. 54;

FIG. 57 is a second cross-sectional view of the pharmaceutical product of FIG. 54;

FIGS. 54' through 57' are exploded, plan, and cross-sectional views of another alternative embodiment of the pharmaceutical product of FIG. 54;

FIG. 57a' is a cross-sectional view of another alternative embodiment of the pharmaceutical product of FIG. 54;

FIG. 58 is an exploded perspective view of a twenty-first embodiment of a pharmaceutical product of the present invention;

FIG. 59 is a plan view of the pharmaceutical product of FIG. 58;

FIG. 60 is a first cross-sectional view of the pharmaceutical product of FIG. 58;

FIG. 61 is a second cross-sectional view of the pharmaceutical product of FIG. 58;

FIG. 61a is a cross-sectional view of an alternative embodiment of the pharmaceutical product of FIG. 58;

FIG. 61b is a cross-sectional view of another alternative embodiment of the pharmaceutical product of FIG. 58;

FIG. 61c is a cross-sectional view of another alternative embodiment of the pharmaceutical product of FIG. 58;

FIG. 62 is an exploded plan view of a twenty-second embodiment of a pharmaceutical product of the present invention;

FIG. 63 is a plan view of the pharmaceutical product of FIG. 62 without the rivet;

FIG. 64 is a cross-sectional view of the pharmaceutical product of FIG. 62 with a portion of the rivet;

FIG. 65 is a cross-sectional view of the pharmaceutical product of FIG. 62 with the rivet locked;

FIG. 66 is an exploded plan view of a twenty-third embodiment of a pharmaceutical product of the present invention;

FIG. 67 is a plan view of the pharmaceutical product of FIG. 66 without the rivet;

FIG. 68 is a cross-sectional view of the pharmaceutical product of FIG. 66 with a portion of the rivet;

FIG. 69 is a cross-sectional view of the pharmaceutical product of FIG. 66 with the rivet locked;

FIG. 70 is an exploded cross-sectional view of a twenty-fourth embodiment of a pharmaceutical product of the present invention;

FIG. 71 is a cross-sectional view of the pharmaceutical product of FIG. 70;

FIG. 72 is an exploded cross-sectional view of a twenty-fifth embodiment of a pharmaceutical product of the present invention;

FIG. 73 is a perspective cross-sectional view of the pharmaceutical product of FIG. 72;

FIG. 74 is a perspective cross-sectional view of a twenty-sixth embodiment of a pharmaceutical product of the present invention;

FIG. 75 is a perspective view of a twenty-seventh embodiment of a pharmaceutical product of the present invention;

FIG. 79 is a cross-sectional view of a thirty-first embodiment of a pharmaceutical product of the present invention;

FIG. 80 is a cross-sectional view of a thirty-second embodiment of a pharmaceutical product of the present invention;

FIG. 81 is a cross-sectional view of a thirty-third embodiment of a pharmaceutical product of the present invention;

FIG. 82 is a cross-sectional view of a thirty-fourth embodiment of a pharmaceutical product of the present invention;

FIG. 83 is a cross-sectional view of a thirty-fifth embodiment of a pharmaceutical product of the present invention;

FIG. 84 is a perspective cross-sectional view of a thirty-sixth embodiment of a pharmaceutical product of the present invention;

FIG. 85 is a perspective view of a thirty-seventh embodiment of a pharmaceutical product of the present invention;

FIG. 86 is a perspective view of a thirty-eighth embodiment of a pharmaceutical product of the present invention;

FIG. 87 is a perspective view of a thirty-ninth embodiment of a pharmaceutical product of the present invention;

FIG. 88 is a perspective view of a fortieth embodiment of a pharmaceutical product of the present invention;

FIG. 95 is a perspective view of a forty-seventh embodiment of a pharmaceutical product of the present invention;

FIG. 96 is a perspective cross-sectional view of a forty-eighth embodiment of a pharmaceutical product of the present invention;

FIG. 97 is a perspective view of a forty-ninth embodiment of a pharmaceutical product of the present invention;

FIG. 98 is an exploded perspective view of a fiftieth embodiment of a pharmaceutical product of the present invention; and FIG. 99 is a perspective cross-sectional view of a fifty-first embodiment of a pharmaceutical product of the present invention.

DETAILED DESCRIPTION OF THE INVENTION

Figure 1:
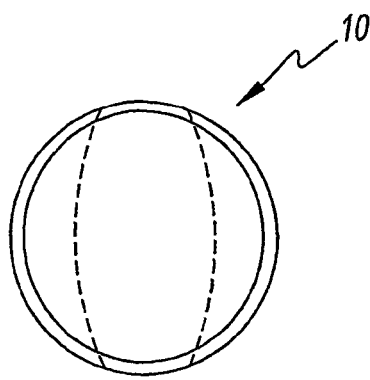
FIG. 1 is a plan view of a first embodiment of a pharmaceutical product of the present invention.
Figure 2:
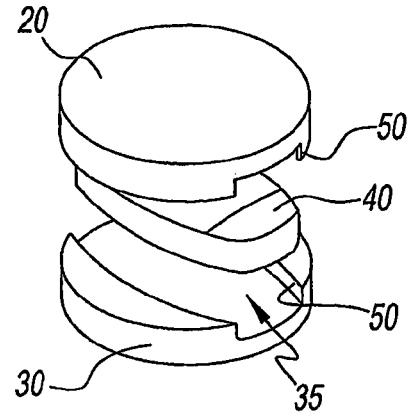
FIG. 2 is an exploded view of the pharmaceutical product of FIG. 1.
Figure 3:
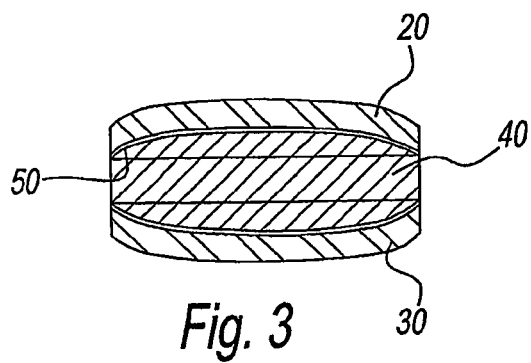
FIG. 3 is a cross-sectional view of the pharmaceutical product of FIG. 1.
Figure 4:
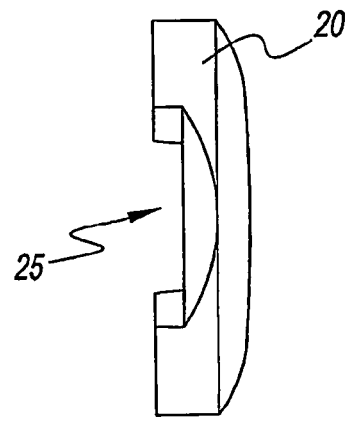
FIG. 4 is a side view of the upper portion of the pharmaceutical product of FIG. 1.
Figure 5:
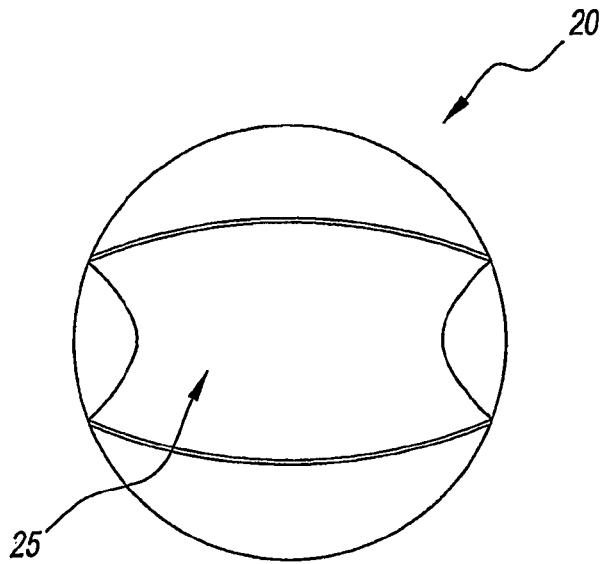
FIG. 5 is a plan view of the upper portion of the pharmaceutical product of FIG. 1.
Figure 6:
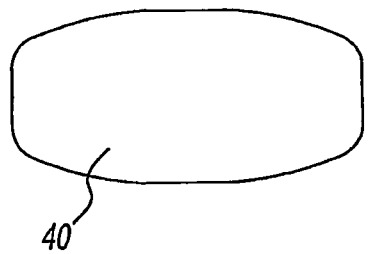
FIG. 6 is a plan view of the middle portion of the pharmaceutical product of FIG. 1.

Referring to the drawings, and in particular FIGS. 1 through 6, a preferred embodiment of the pharmaceutical product is shown and generally referred to by reference numeral 10. Product 10 has an upper portion 20, a lower portion 30 and a middle portion 40. Upper, lower and middle portions 20, 30 and 40 form three distinct components. These components can be formed by tablet compression, although the present invention contemplates the use of other methods and processes for forming the individual components.

The upper, lower and middle portions 20, 30 and 40 can include excipients, such as in the core matrix, to control the release rates for the three portions. One or more (or none) of the upper, lower and middle portions 20, 30 and 40 can also be coated, such as by using a conventional coating process, with distinct coating systems with various functionalities to further control the rate of release of each of the three portions.

The upper, lower and middle portions 20, 30 and 40 are provided with interlocking shapes. The interlocking shapes allow for release of the active agent from all three of the portions and strengthen the connection between the portions. The upper, lower and middle portions 20, 30 and 40 are preferably non-releasably or substantially non-releasably connected or secured together so as to deliver multiple active agents through the use of a single delivery device or vehicle.

The upper, lower and middle portions 20, 30 and 40 can be connected through various methods, such as, for example, use of glues or adhesives, polymers, waxes; mechanical methods, structures or means; application of energy, such as thermal welds, inductive welds and ultrasonic welds; and any combination of such methods.

The connection methods, and the components or materials used therein, can include, but are not limited to, polymers, such as polyethylene glycol (PEG) or hydroxypropylmethylcellulose (HPMC); gelatin, such as Pharmagel®; starch; the Methocel® series of coatings from Colorcon (methylcellulose and hypromellose, e.g. cellulosic polymeric backbones), and their line of Opradry® overcoatings containing such, the overcoating after being applied to the core upon adhesion is first wetted with water or alcohol, or a combination thereof (e.g., ethanol, methanol, or isopropanol (IPA)), gum, such as chicle, latex sap from the sapodilla tree and natural rubber; gum bases, such as natural resins, including sorva and jelutong; waxes, such as cheese wax (e.g., Paradip®), chewing gum wax (e.g., Paramelt®), butyl or polyisobutylene rubber, beeswax, carnauba wax and microcrystalline wax (e.g., Polywax®); food grade adhesives, such as sugar-based edible adhesive; envelope grade adhesives; printed inks (as binders), such as HPMC and shellac; hot melt food grade glues; epoxy; opadry dental adhesives; and quick dissolving or heat sensitive films.

The connection methods further include, but are not limited to, mechanical methods, such as, for example, a locking pin mechanism; a snap-fit; a screw-fit; a pressure sensitive compression; an injection molded locking pin; banding; shrink wrapping; and injection mold gluing. The connection methods further include, but are not limited to, application of energy, such as, for example, ultrasonic welding; lasers; microwaves; heat; and friction welding. The present invention also contemplates the use of other connection methods, structures or components that facilitate and/or strengthen the connection between the upper, lower and middle portions 20, 30 and 40.

Upper portion 20 has a recess 25 and lower portion 30 has a recess 35. The recesses 25 and 35 preferably extend to the periphery or outer edge of upper and lower portions 20 and 30. Recesses 25 and 35 conform to the shape of middle portion 40 so that a tight fit can be achieved between the upper, lower and middle portions 20, and 40 when product 10 is assembled. In the preferred embodiment, middle portion 40 has an oval or round shape, although the present invention contemplates the use of other shapes, such as, rectangular, which can facilitate and strengthen the connection between the components. The tight fit between the upper, lower and middle portions 20, 30 and 40 strengthens the connection between the components, as well as provides a more aesthetically pleasing, unified product 10.

Middle portion 40 is narrower than upper and lower portions 20 and 30 so that an interlocking interface or boundary 50 is formed between the three portions when they are connected. The interlocking interface 50 is preferably non-linear in order to provide structural support by way of a mechanical lock being formed between the upper, lower and middle portions 20, 30 and 40. The interlocking interface 50 also increases the surface contact area between the upper, lower and middle portions 20, and 40 so that there is more area for connection and a greater bond formed.

The interlocking interface 50 allows middle portion 40 to be exposed so that the middle portion is also able to release its active agent at the desired release rate. However, the present invention contemplates recesses 25 and 35 being positioned (e.g., centrally) along upper portion 20 and lower portion 30 such that when all three portions are connected, the middle portion 40 is not exposed. In such an alternative embodiment, the release of the active agent in middle portion 40 would be dependent on the deterioration of either or both of upper and lower portions 20 and 30 so that the middle portion eventually becomes exposed.

Product 10 is preferably formed through use of a rotary press to compress three distinct matrix cores in the desired shapes of the upper, lower and middle portions 20, 30 and 40. A coating pan, or other coating method or means, can coat any number of the upper, lower and middle portions 20, 30 and 40. The upper, lower and middle portions 20, 30 and 40 can be positioned together in an interlocked fashion and using a binding process, such as one of the connection methods described above, the portions can be connected into one entity or delivery vehicle.

The upper, middle and lower portions 20, 30, and 40 may be independently formulated to achieve a different desired rate of release, e.g., as a controlled rate of release, such as a slow-rate, or a medium-rate of release, or an immediate-rate of release. As such, product 10 can, if desired, deliver three separate active agents at three different rates of release, or one active at three different rates of release. Alternatively, product 10 could deliver one medicament at two different release rates, and a second medicament at one release rate, etc. This allows product 10 to target specific areas of the gastro intestinal tract for delivery of the various active agents. In product 10, the upper portion 20 has a medium release rate, the lower portion 30 has a slow release rate and the middle portion 40 has an immediate release rate. However, the present invention contemplates the use of other release rates for one or more the components of product 10 or any of the other embodiments that are described herein.

Product 10 provides for multiple active agents that are independent of each other in a single entity to achieve a combination therapy product. The coating on one or more (or none) of the upper, lower and middle portions 20, 30 and 40 further provides for control of the release rates of the active agents. The use of three distinct components for upper, lower and middle portions 20, 30 and 40, optionally in combination with the coating of each of the components, allows product 10 to provide for up to six different modes of release at the various stages of the GI tract. Additionally, incompatible active agents can still be delivered through use of a single vehicle, i.e., product 10.

Figures 7, 8:
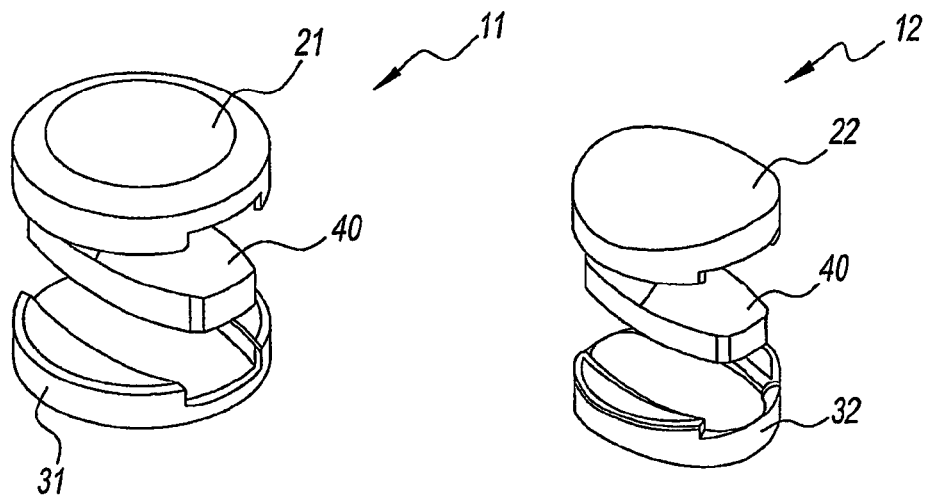
FIG. 7 is an exploded view of a second embodiment of a pharmaceutical product of the present invention.
FIG. 8 is an exploded view of a third embodiment of a pharmaceutical product of the present invention.

Referring to FIGS. 7 and 8, second and third embodiments of the pharmaceutical product are shown and generally represented by reference numerals 11 and 12, respectively. Products 11 and 12 have features similar to product 10 except that the shape of the upper portions 21 and 22 and the shape of the lower portions 31 and 32 are different from product 10. Upper and lower portions 21 and 31 of product 11 have a chamfered circumferential edge, which can facilitate swallowing, handling, and provide overall aesthetic appeal to the product.

Upper and lower portions 22 and 32 of product 12 have a rounded, convex or partially convex shape, which can also facilitate swallowing, handling, and provide overall aesthetic appeal to the product.

Figures 8A, 8B:
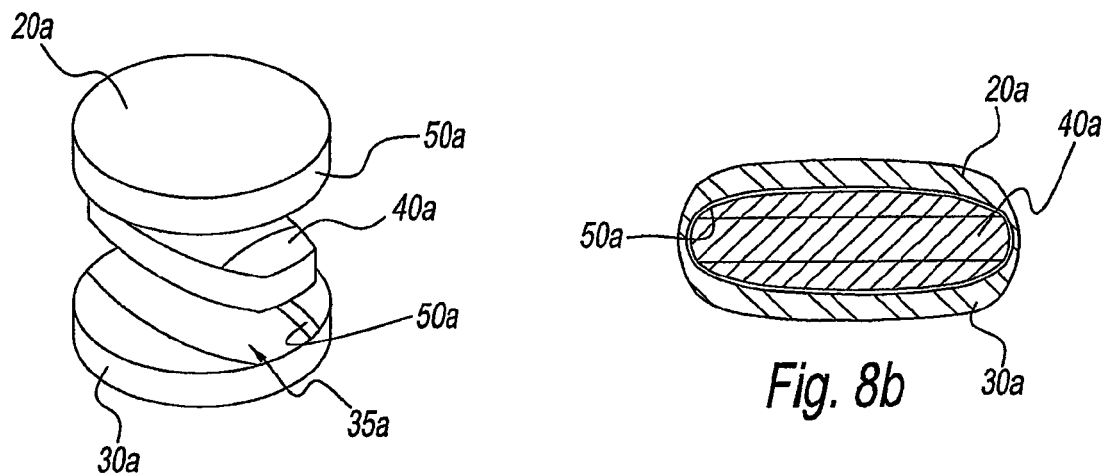

Referring to FIGS. 8a and 8b, an alternative embodiment of the pharmaceutical product 10 is shown and generally represented by reference numeral 10a. Product 10a has features similar to product 10 except that the middle portion 40a is not exposed. By enclosing middle portion 40a, product 10a provides for delayed release of the active agent in the middle portion, which is based upon deterioration of the upper portion 20a and/or the lower portion 30a.

Figure 9:
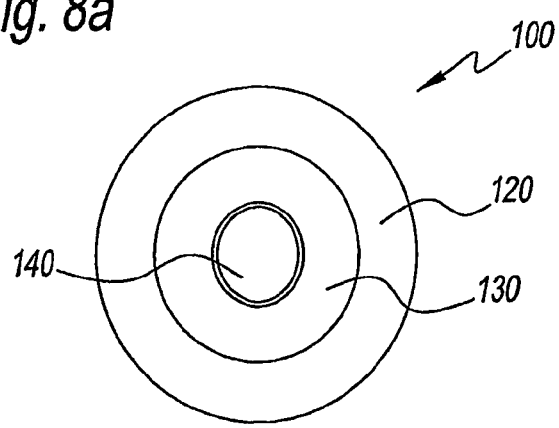
FIG. 9 is a plan view of a fourth embodiment of a pharmaceutical product of the present invention.
Figure 10:
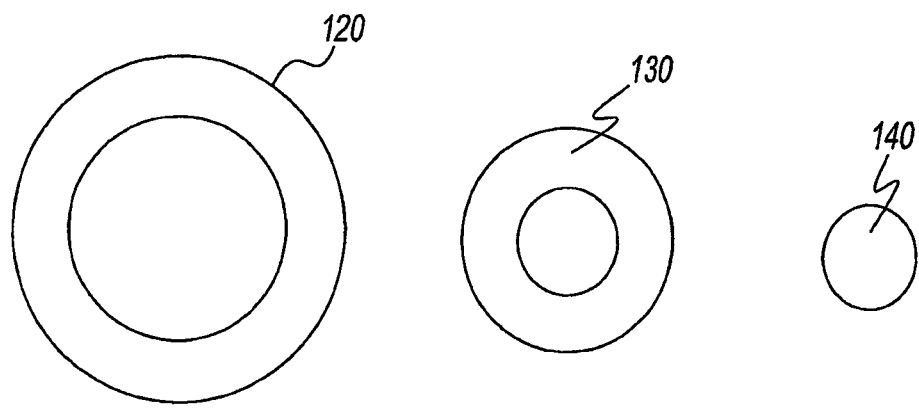
FIG. 10 is an exploded plan view of the pharmaceutical product of FIG. 9.

Referring to FIGS. 9 and 10, a fourth embodiment of the pharmaceutical product is shown and generally referred to by reference numeral 100. Product 100 has an outer portion 120, an intermediate portion 130 and an inner portion 140 that form three distinct components, which can be formed by tablet compression.

Similar to product 10, the outer, intermediate and inner portions 120, 130 and 140 of product 100 can include excipients to control the individual release rates and can also be coated to further control the release rates. The outer, intermediate and inner portions 120, 130 and 140 are concentrically aligned when connected or assembled, with the tops and bottoms of the intermediate and inner portions remaining exposed, which allows for release of the active agent for all three of the portions. The concentric alignment of the outer, intermediate and inner portions 120, 130 and 140 increases surface area therebetween, which strengthens their connection.

The outer, intermediate and inner portions 120, 130 and 140 can be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The outer, intermediate and inner portions 120, 130 and 140 are independently formulated to achieve a desired rate of release, e.g., a medium rate, a slow rate and an immediate rate, and are each compressed to make the desired ring or donut-like shape for the outer and intermediate portions and the cylindrical shape for the inner portion. The outer, intermediate and inner portions 120, 130 and 140 can be coated with a functional coating system to further vary, or control, the rate of release and the three components are interlocked together in a concentric alignment. In product 100, the inner portion 140 has an immediate release rate, the intermediate portion 130 has a medium release rate and the outer portion 140 has a slow release rate. Although, the present invention contemplates the use of other release rates.

Figure 11:
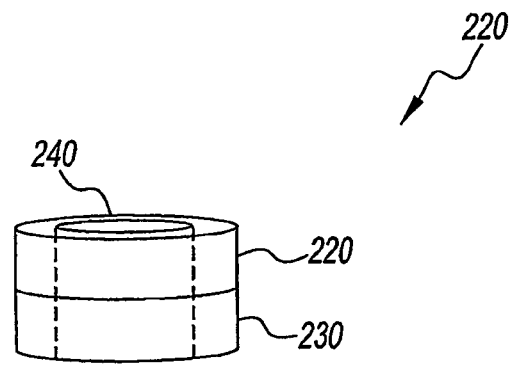
FIG. 11 is a perspective view of a fifth embodiment of a pharmaceutical product of the present invention.
Figure 12:
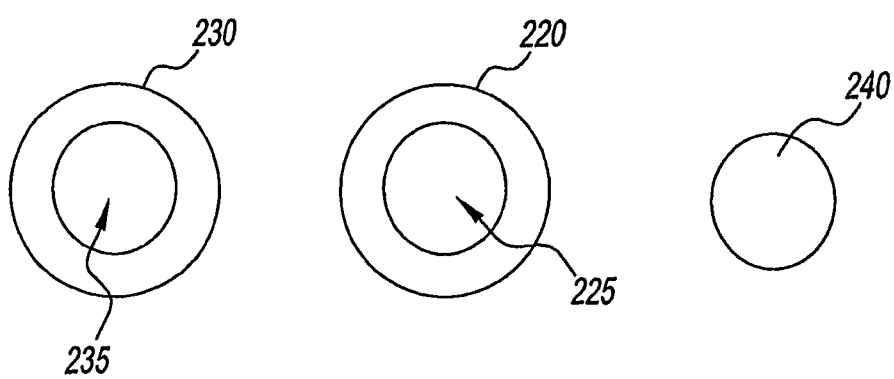
FIG. 12 is an exploded plan view of the pharmaceutical product of FIG. 11.

Referring to FIGS. 11 and 12, a fifth embodiment of the pharmaceutical product is shown and generally referred to by reference numeral 200. Product 200 has an upper portion 220, a lower portion 230 and an inner portion 240 that form three distinct components, which can be formed by tablet compression.

Similar to products 10 and 100, the upper, lower and inner portions 220, 230 and 240 can include excipients to control the release rates and can also be coated to further control the release rates. The upper portion 220 is seated upon the lower portion 230, while the inner portion 240 is positioned in the central holes 225 and 235 of the upper and lower portions. The upper, lower and inner portions 220, 230 and 240 all remain exposed, which allows for release of the active agent for all three of the portions.

The upper, lower and inner portions 220, 230 and 240 can be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The upper, lower and inner portions 220, 230 and 240 are independently formulated to achieve a desired rate of release, e.g., a medium rate, a slow rate and an immediate rate. Each of the upper, lower and inner portions 220, 230 and 240 are compressed to make the desired ring or donut-like shapes for the upper and lower portions and the cylindrical shape of the inner portion, which allows for the alignment of the three portions. The upper, lower and inner portions 220, 230 and 240 can be coated with a functional coating system to further control the rate of release and the three components are interlocked together. In product 200, the inner portion 240 has an immediate release rate, the lower portion 230 has a medium release rate and the upper portion 240 has a slow release rate. However, the present invention contemplates the use of other release rates for the different components.

Figure 13:
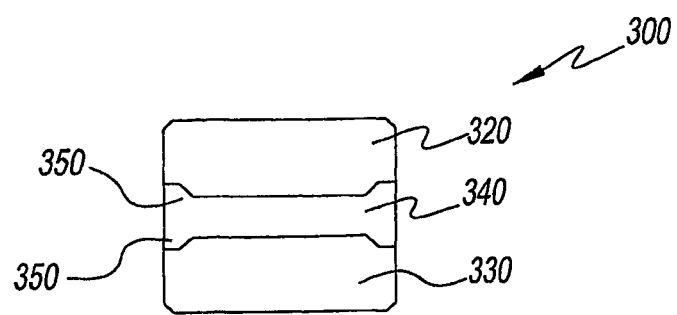
FIG. 13 is a plan view of a sixth embodiment of a pharmaceutical product of the present invention.
Figure 14:
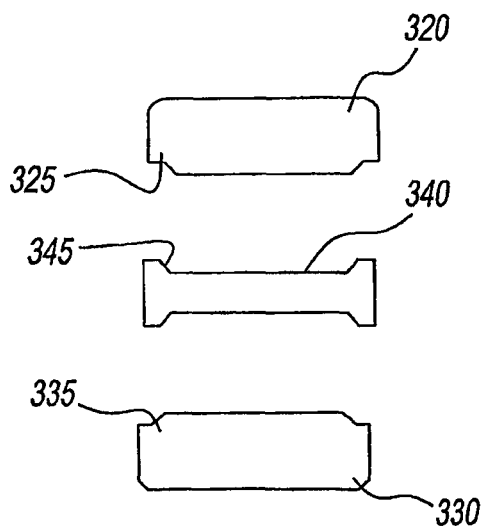
FIG. 14 is an exploded plan view of the pharmaceutical product of FIG. 13.

Referring to FIGS. 13 and 14, a sixth embodiment of the pharmaceutical product is shown and generally referred to by reference numeral 300. Product 300 has an upper portion 320, a lower portion 330 and a middle portion 340 that form three distinct components, which can be formed by tablet compression.

Similar to products 10, 100 and 200, the upper, lower and middle portions 320, 330 and 340 can include excipients and can also be coated to control the release rates of their respective active agents. The upper portion 320 is seated upon the middle portion 340, which is seated upon the lower portion 330. These components can be connected together via snap-fit or other mechanical connection. The upper, lower and middle portions 320, 330 and 340 all remain exposed, which allows for release of the active agent for all three of the portions.

The upper, lower and middle portions 320, 330 and 340 can also be connected through various methods, such as, for example, glues or adhesives; polymers; waxes; mechanical methods, structures or means; by application of energy; and any combination of such methods, including the methods described above with respect to product 10 and/or other methods, structures or binding ingredients that facilitate or strengthen the connection between the portions.

The upper, lower and middle portions 320, 330 and 340 are independently formulated to achieve a desired rate of release, e.g., a medium rate, a slow rate and an immediate rate, and are each compressed to make the desired interlocking shapes that provide for alignment of the three portions. Middle portion 340 has male mating structures or ridges 345 along its edges while upper and lower portions 320 and 330 have female mating structures or ridges 325 and 335 along their edges. The male and female mating structures 325, 335 and 345 form an interlocking interface or boundary 350 when the upper, lower and middle portions 320, 330 and 340 are stacked upon each other and connected.

The interlocking interface 350 is preferably non-linear in order to provide structural support by way of a mechanical lock being formed between the upper, lower and middle portions 320, 330 and 340. The interlocking interface 350 also increases the surface contact area between the upper, lower and middle portions 320, 330 and 340 so that there is more area for connection and a greater bond formed. The male and female mating structures 325, 335 and 345 also provide for self-centering of the upper, lower and middle portions 320, 330 and 340 which further facilitates the manufacturing of product 300.

During the manufacturing process, the upper, lower and middle portions 320, 330 and 340 can be coated with a functional coating system to further control the rate of release and the three components are interlocked together. In product 300, the middle portion 340 has an immediate release rate, the lower portion 330 has a slow release rate and the upper portion 320 has a medium release rate. However, the present invention contemplates the use of other release rates for one or more of the components of product 300.

Referring to FIGS. 15 through 17, a seventh embodiment of the pharmaceutical product is shown and generally referred to by reference numeral 400. Product 400 has an upper portion 420, a lower portion 430 and a middle portion 440 that form three distinct components, which can be formed by tablet compression.

Similar to the components of the embodiments described above, the upper, lower and middle portions 420, 430 and 440 are independently formulated to achieve a desired rate of release, e.g., a medium rate, a slow rate and an immediate rate. The upper, lower and middle portions 420, 430 and 440, can include excipients to control the release rates, and can also be coated to further control the release rates. The upper, lower and middle portions 420, 430 and 440 all remain exposed, which allows for release of the active agent for all three of the portions.

Product 400 provides for interlocking of the middle portion 440 with the upper and lower portions 420 and 430. Preferably, the interlock is a mechanical interlock. The product 400 can also use additional connection methods, such as one of the bonding techniques described above, as well as other connection methods.

The mechanical interlock of product 400 is preferably a detent engagement of the upper and lower portions 420 and 430 onto the middle portion 440. The middle portion 440 has a pair of grooves, channels or recesses 441 disposed along opposing sides of the middle portion. The grooves 441 are adjacent to, and partially define, outwardly extending edges or detents 442, which are located on the corners of the middle portion 440. The grooves 441 and the detents 442 provide the middle portion 440 with an hour-glass-like shape, as seen in the view of FIG. 15.

The upper and lower portions 420 and 430 have recesses 425 and 435. The recesses 425 and 435 have grooves 421 and 431, respectively, and detents 422 and 432, respectively along the sidewalls of the grooves. The detents 422 and 432 of the upper and lower portions 420 and 430 can be slid along grooves 441 of the middle portion 440, while the detents 442 of the middle portion can be slid along grooves 421 and 431 of the upper and lower portions, as shown by arrows 410. This allows the middle portion 440 to be slid into place between the upper and lower portions 420 and 440. The detents 422, 432 and 442 provide the mechanical connection or lock between the components.

The grooves 421, 431 and 441 and the detents 422, 432 and 442 are chamfered or smoothly formed to reduce friction and/or facilitate the movement of the upper, lower and middle portions 420, 430 and 440 with respect to each other. However, the present invention contemplates sharper grooves and detents where stronger engagements and/or less play is desired. The present invention also contemplates the depth and angle of the grooves 421, 431 and 441 and the extent and angle of the detents 422, 432 and 442 being such as to achieve a desired strength of connection and/or friction against sliding with respect to each other, while also facilitating the initial connection of these components. The detents 421 and 431 are separated from each other to define gaps 411 on opposing sides of the product 400. Gaps 411 can be of various size and provide for additional exposure of middle portion 440, in addition to the exposure provided along the top and bottom portions as shown clearly in FIG. 15.

While product 400 uses a detent engagement of the upper and lower portions 420 and 430 onto middle portion 440, the present invention contemplates other types of mechanical connections between the separate components, such as, for example, a snap-fit or a friction fit. The mechanical connection of these components can also be used in conjunction with other connection methods such as, for example, glues or adhesives, polymers, waxes, application of energy and any combination of such methods. For example, but not limited to, adhesive or the like can be applied between middle portion 440 and the upper and lower portions 420 and 430 to prevent the middle portion from sliding out from therebetween.

Figure 18:
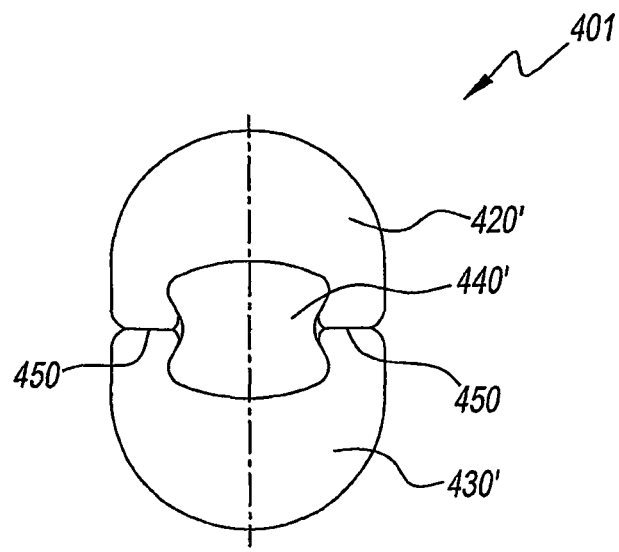
FIG. 18 is a plan view of an eighth embodiment of a pharmaceutical product of the present invention.
Figure 19:
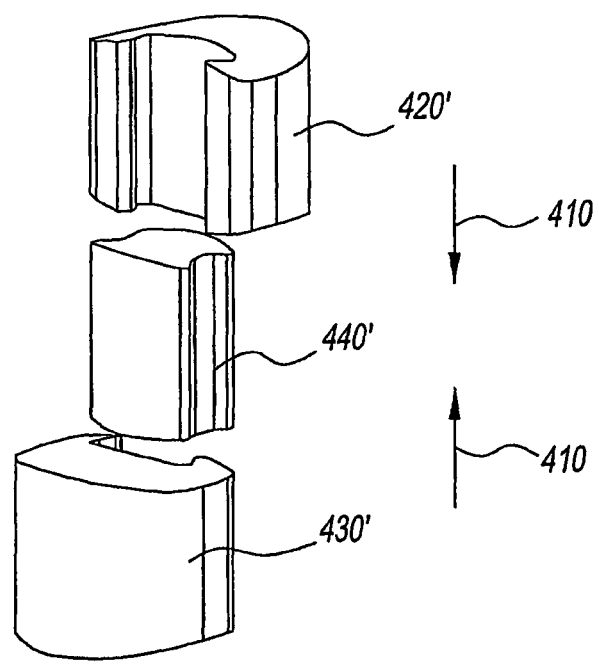
FIG. 19 is an exploded perspective view of the pharmaceutical product of FIG. 18.

Referring to FIGS. 18 and 19, an eighth embodiment of the pharmaceutical product is shown and generally referred to by reference numeral 401. Product 401 has features similar to product 400 and also uses a detent engagement of the three components that are slidingly engaged with one another. However, the shapes and angles of the corresponding detent-groove connections are more closely aligned. As seen in FIG. 18, the middle portion 440' is tightly sandwiched in between the upper and lower portions 420' and 430', which also abut against each other along boundaries 450. This provides for a more secure product 401 and reduces any shifting of the components when assembled. The tight alignment between the upper, lower and middle portions 420', 430' and 440', as well as the addition of a friction bearing surface (boundaries 450) directly between the upper and lower portions, can assist in preventing the components from sliding out of position when assembled. Additionally, the tight fit provides more surface area for connection and improves the strength of the product 401.

The connection of upper, lower and middle portions 420', 430' and 440' can also be enhanced through use of other connection methods such as, for example, glues or adhesives, polymers, waxes and/or application of energy. These additional connection methods can be applied or performed along the boundaries 450 or elsewhere on the product 401, which is facilitated by abutment of the upper and lower portions 420, 430 along the boundaries 450, as compared to the gaps 411 of product 400.

Figure 20:
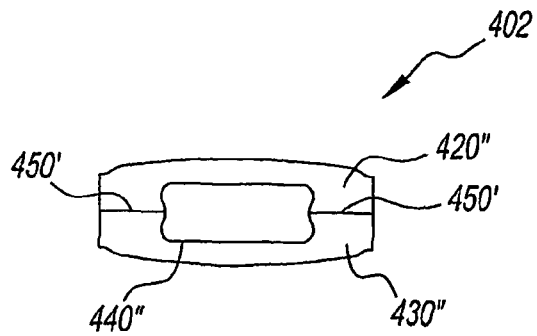
FIG. 20 is a plan view of a ninth embodiment of a pharmaceutical product of the present invention without the band.
Figure 21:
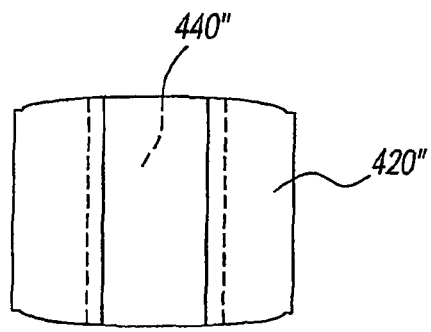
FIG. 21 is a top view of the pharmaceutical product of FIG. 20.
Figure 22:
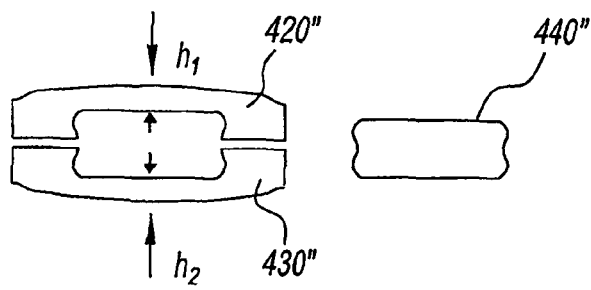
FIG. 22 is an exploded plan view of the pharmaceutical product of FIG. 20.
Figure 23:
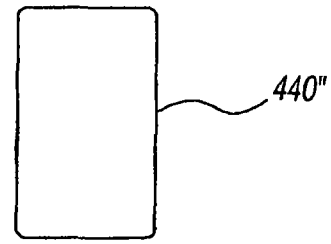
FIG. 23 is a top view of the middle portion of the pharmaceutical product of FIG. 20.

Referring to FIGS. 20 through 24, a ninth embodiment of the pharmaceutical product is shown and generally referred to by reference numeral 402. Product 402 has features similar to product 400, and can also use a detent engagement of the three components that are slidingly engaged with one another. However, the shapes and angles of the corresponding detent-groove connections are more closely aligned. As seen in FIG. 20, the middle portion 440" is tightly sandwiched in between the upper and lower portions 420" and 430", which also abut against each other along boundaries 450'. This provides for a more secure product 402 and reduces or eliminates any shifting of the components when assembled.

Similar to product 401, the tight alignment between the upper, lower and middle portions 420", 430" and 440" of product 402, as well as the addition of a friction bearing surface (boundaries 450') directly between the upper and lower portions, can assist in preventing the components from sliding out of position when assembled. The connection of upper, lower and middle portions 420", 430" and 440" can also be enhanced through use of other connection methods such as, for example, glues or adhesives, polymers, waxes and/or application of energy. These additional connection methods can be applied or performed along the boundaries 450' or elsewhere on the product 402.

The upper and lower portions 420" and 430" have a reduced height or thickness $h_1$ and $h_2$, respectively, along their center portions. These reduced thicknesses $h_1$ and $h_2$ provide a product 402 with a reduced profile that can facilitate swallowing and/or manipulating. The reduced thicknesses h1 and h2 can also be used to provide the upper and lower portions 420" and 430" with resiliency so that rather than sliding the separate components together along middle portion 440", they can be engaged via a snap-fit. Product 402 can also include additional detents (not shown) such as, for example, a ratchet-type mechanism, which prevent the upper, lower and middle portions 420", 430" and 440" from sliding out from each other. These additional detents can be used where the components are engaged via a snap-fit or can be used with the sliding engagement described above.

Product 402 has a band or holding member 460 that prevents the middle portion 440" from sliding out of its position between upper and lower portions 420" and 430". The band 460 can be applied in a secondary manufacturing step after the components have been slidingly (or snap-fitted) together. Due to the detent engagement of the upper and lower portions 420" and 430" with the middle portion 440", the band 460 only needs to be strong enough to prevent sliding of the three components.

Figure 24:
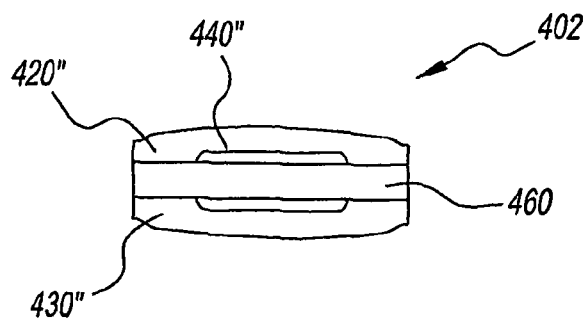
FIG. 24 is a plan view of the pharmaceutical product of FIG. 20 with the band.
Figure 24A:
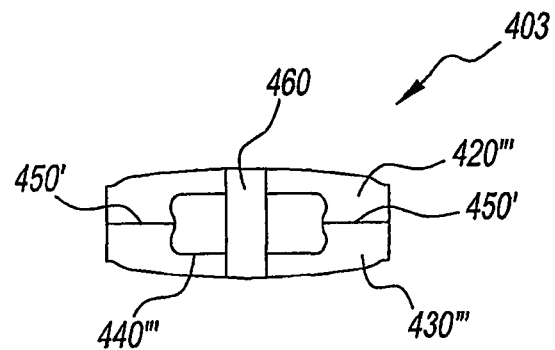
FIG. 24a is a plan view of a tenth embodiment of a pharmaceutical product of the present invention, which is similar to the embodiment of FIGS. 20-24 but with the band in a vertical direction.

Referring to FIG. 24a, a tenth embodiment of the pharmaceutical product is shown and generally referred to by reference numeral 403. Product 403 has features similar to product 402, and also uses a detent engagement of the three components that are slidingly engaged with one another. Product 403 further has a band or holding member 460a that prevents the middle portion 440''' from sliding out of its position between upper and lower portions 420''' and 430'''. The band 460a can be applied in a secondary manufacturing step after the components have been slidingly (or snap-fitted) together. Due to the detent engagement of the upper and lower portions 420''' and 430''' with the middle portion 440''', the band 460a only needs to be strong enough to prevent sliding of the three components. The band 460a is disposed along a vertical direction, as opposed to band 460 of FIG. 24, which is disposed along a horizontal direction. Band 460a provides for more exposure of middle portion 440'''. Boundaries 450' can be provided with an adhesive or other bonding agent to further enhance the connection and strength of product 403.

Figure 25:
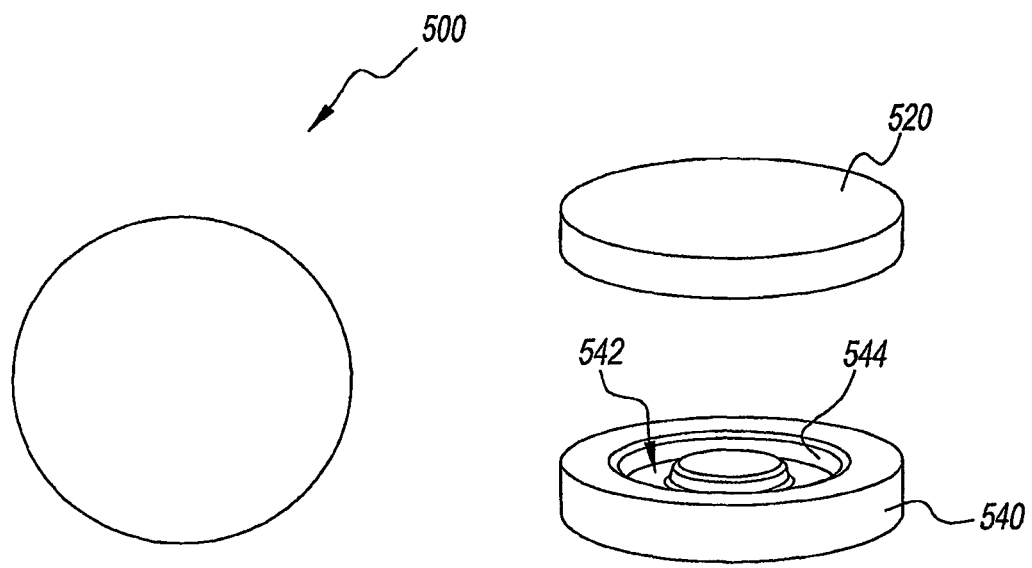
FIG. 25 is a top plan view of an eleventh embodiment of a pharmaceutical product of the present invention.
Figure 26:
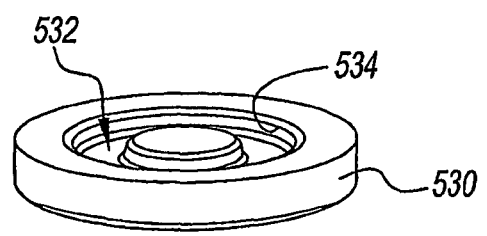
FIG. 26 is an exploded perspective view of the pharmaceutical product of FIG. 25.
Figure 27:
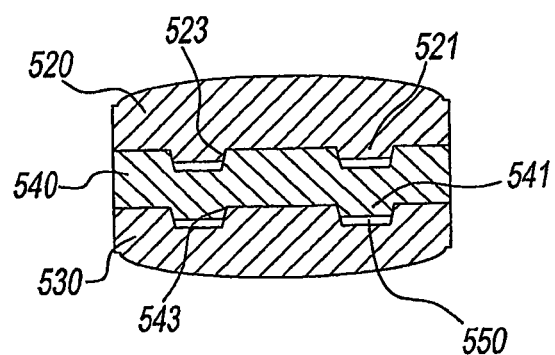
FIG. 27 is a cross-sectional view of the pharmaceutical product of FIG. 25.

Referring to FIGS. 25 through 27, an eleventh embodiment of the pharmaceutical product is shown and generally referred to by reference numeral 500. Product 500 has an upper portion 520, a lower portion 530 and a middle portion 540 that form three distinct components, which can be formed by tablet compression.

Similar to the components of the embodiments described above, the upper, lower and middle portions 520, 530 and 540 are independently formulated to achieve a desired rate of release, e.g., a medium rate, a slow rate and an immediate rate, can include excipients to control the release rates, and can also be coated to further control the release rates. The upper, lower and middle portions 520, 530 and 540 all remain exposed, which allows for release of the active agent for all three of the portions.

Product 500 provides for mechanical interlocking of the middle portion 540 with the upper and lower portions 520 and 530 through a snap-fit engagement. To enhance the connection, additional connection methods, such as one of the bonding techniques described above, can also be used.

The snap-fit engagement occurs between locking rings or annular projections 521 and 541 on upper and middle portions 520 and 540 and annular recesses 542 and 532 on middle and lower portions 540 and 530, respectively. The locking rings 521 and 541 and annular recesses 542 and 532 can also be connected based upon a friction fit, and adhesive or other bonding agents can be used along the ring and/or recesses to further improve the connection.

The locking rings 521 and 541 and annular recesses 542 and 532 have chamfered or angled edges to facilitate the engagement between the upper, lower and middle portions 520, 530 and 540. The present invention also contemplates the extent and angle of the locking rings 521 and 541 and the depth and angle of the annular recesses 542 and 532 being such as to achieve a desired strength of connection and/or friction against releasing from one another, while also facilitating the initial connection of these components.

The sidewalls 523 and 543 of the locking rings 521 and 541 can be angled or tapered inwardly (the distal end being wider) while the sidewalls 544 and 534 of the annular recesses 542 and 532 can be angled or tapered outwardly (the distal ends being narrower) so as to substantially prevent the upper, lower and middle portions 520, 530 and 540 from coming apart once they are initially engaged via snap-fit similar to a ratchet-like holding mechanism. The locking rings 521 and 541 can have grooves or the like around their sidewalls 523 and 543 and the annular recesses 542 and 532 can have corresponding detents or the like around their sidewalls 544 and 534 which enhance the connection between the upper, lower and middle portions 520, 530 and 540. Gaps 550 can be provided between the locking rings 521 and 541 to ensure that the middle portion 540 is able to more easily snap-fit with the upper and lower portions 520 and 530.

Figure 27A:
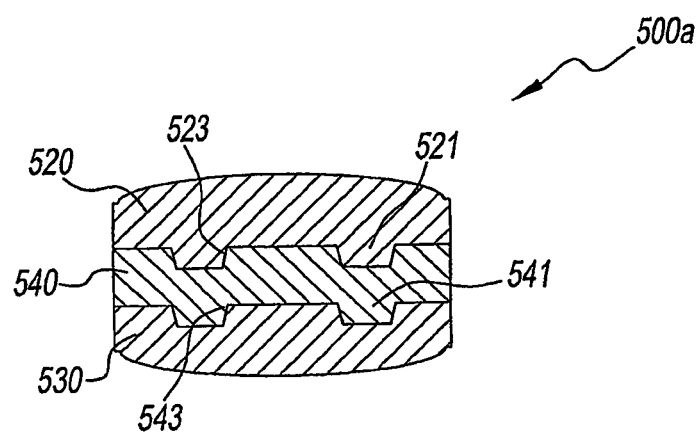
FIG. 27a is a cross-sectional view of an alternative embodiment of the pharmaceutical product of FIG. 25.
Figure 28:
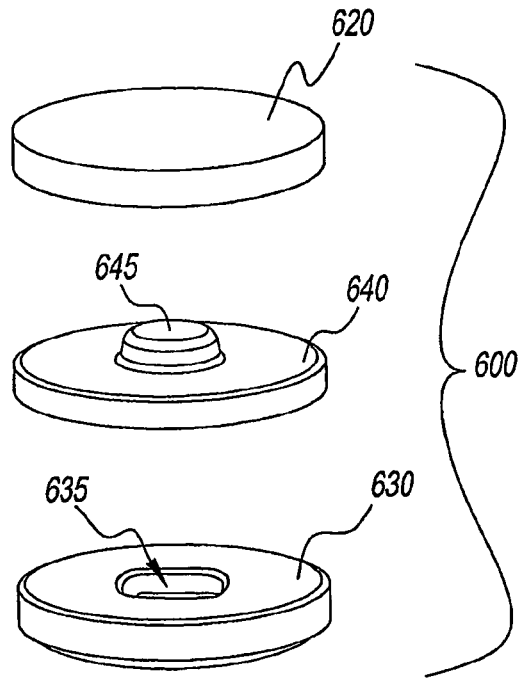
FIG. 28 is an exploded perspective view of a twelfth embodiment of a pharmaceutical product of the present invention.
Figure 29:
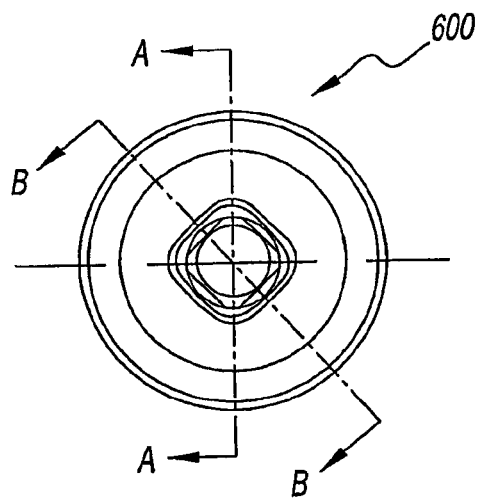
FIG. 29 is a plan view of the pharmaceutical product of FIG. 28.
Figure 30:
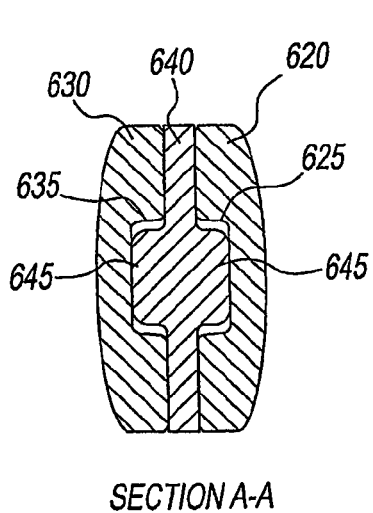
FIG. 30 is a first cross-sectional view of the pharmaceutical product of FIG. 28.
Figure 31:
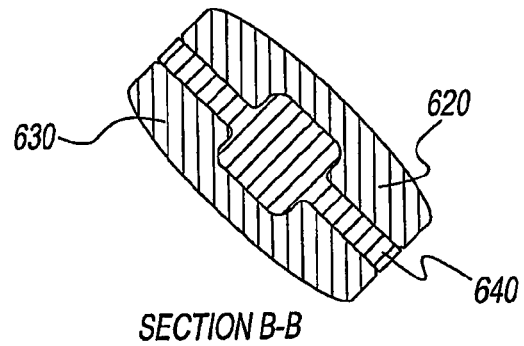
FIG. 31 is a second cross-sectional view of the pharmaceutical product of FIG. 28.

Referring to FIG. 27a, the gaps between the locking rings 521a and 541a can be eliminated to provide a tighter fit for product 500a than with product 500.

Referring to FIGS. 28 through 31, a twelfth embodiment of the pharmaceutical product is shown and generally referred to by reference numeral 600. Product 600 has an upper portion 620, a lower portion 630 and a middle portion 640 that form three distinct components, which can be formed by tablet compression.

Similar to the components of the embodiments described above, the upper, lower and middle portions 620, 630 and 640 are independently formulated to achieve a desired rate of release, e.g., a medium rate, a slow rate and an immediate rate, can include excipients to control the release rates, and can also be coated to further control the release rates. The upper, lower and middle portions 620, 630 and 640 all remain exposed, which allows for release of the active agent for all three of the portions.

Product 600 provides for mechanical interlocking of the middle portion 640 with the upper and lower portions 620 and 630 through a snap-fit engagement. To enhance the connection, additional connection methods, such as one of the bonding techniques described above, can also be used.

The snap-fit engagement occurs between center hubs or projections 645 on opposing sides of middle portion 640 and center recesses 625 and 635 on upper and lower portions 620 and 630. The center hub 645 has a substantially circular shape while the center recesses 625 and 635 have substantially square shapes. As a result, the sidewalls of the center hub 645 do not completely abut the sidewalls of each of the center holes 625 and 635, as is evident in the cross-sectional views of FIGS. 30 and 31. This facilitates the initial engagement of the middle portion 640 with the upper and lower portions 620 and 630. The center hub 645 and the center holes 625 and 635 can also be connected based upon a friction fit, and/or adhesive or other bonding agents can be used to further improve the connection. The extent and angle of the center hub 645 and the depth and angle of the center recesses 625 and 635 provide for a desired strength of connection and/or friction against releasing from one another, while also facilitating the initial connection of these components.

Referring to FIGS. 31a through 31c, an alternative embodiment of product 600 is shown which eliminates any gap between the mechanical interlocking portions. Product 600a provides for mechanical interlocking of the middle portion 640a with the upper and lower portions 620a and 630a through a snap-fit engagement using corresponding circular center hubs 645a and center recesses 625a and 635a. The center hubs 645a and center recesses 625a and 635a have similar diameters to allow for the snap-fit engagement and eliminate any gaps therein.

Figure 32:
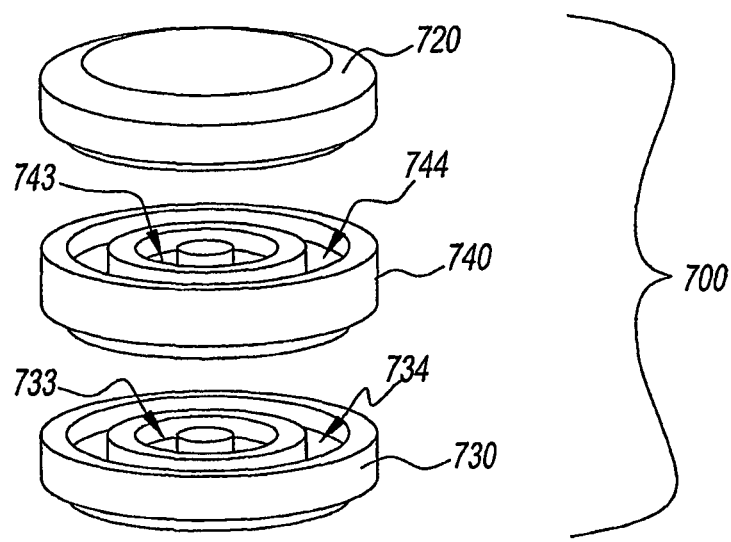
FIG. 32 is an exploded perspective view of a thirteenth embodiment of a pharmaceutical product of the present invention.
Figure 33:
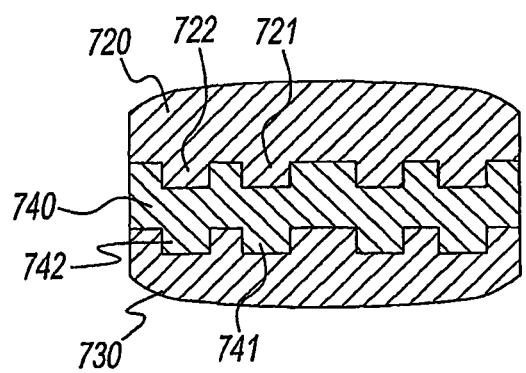
FIG. 33 is a cross-sectional view of the pharmaceutical product of FIG. 32.

Referring to FIGS. 32 and 33, a thirteenth embodiment of the pharmaceutical product is shown and generally referred to by reference numeral 700. Product 700 has features similar to product 500 and utilises a snap-fit engagement of the three distinct components. Product 700 has first locking rings 721 and 741 and second locking rings 722 and 742 on upper and middle portions 720 and 740, respectively. The first locking rings 721 and 741 and the second locking rings 722 and 742 are concentrically aligned.

The middle and lower portions 740 and 730 have corresponding first annular recesses 743 and 733 and second annular recesses 744 and 734, respectively. The first annular recesses 743 and 733 and the second annular recesses 744 and 734 are concentrically aligned. These components can also be assembled via friction fit, and adhesive or other bonding agents can be used along the ring and/or recesses to further improve the connection.

The shapes and angles of the corresponding snap-fit connections of the upper, lower and middle portions 720, 730 and 740 are closely aligned. As seen in FIG. 33, the middle portion 740 is tightly sandwiched in between the upper and lower portions 720 and 730. This provides for a more secure product 700 and reduces any shifting of the components when assembled.

Figure 34:
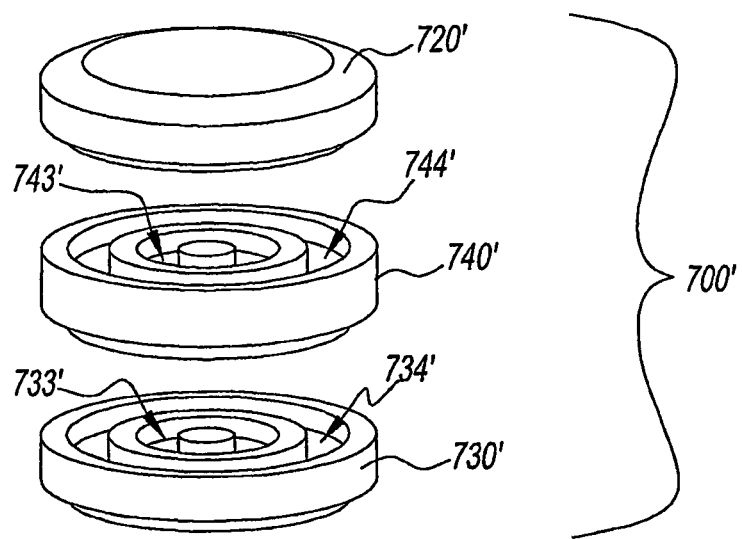
FIG. 34 is an exploded perspective view of a fourteenth embodiment of a pharmaceutical product of the present invention.
Figure 35:
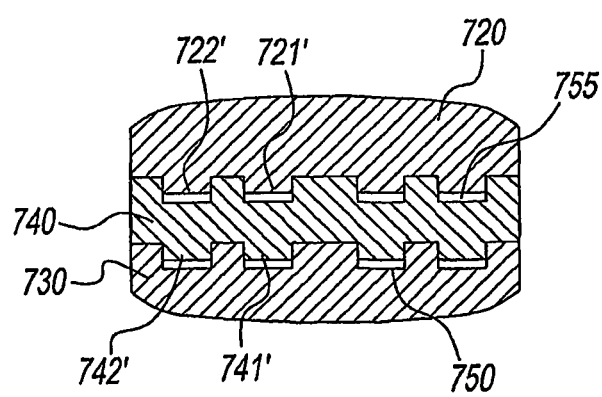
FIG. 35 is a cross-sectional view of the pharmaceutical product of FIG. 34.
Figure 37:
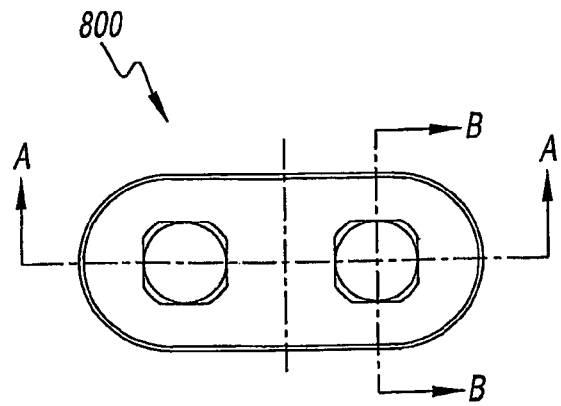
FIG. 37 is a plan view of the pharmaceutical product of FIG. 36.
Figure 36:
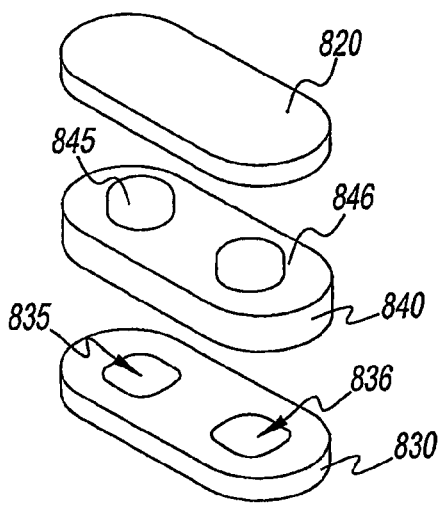
FIG. 36 is an exploded perspective view of a fifteenth embodiment of a pharmaceutical product of the present invention.
Figure 38:
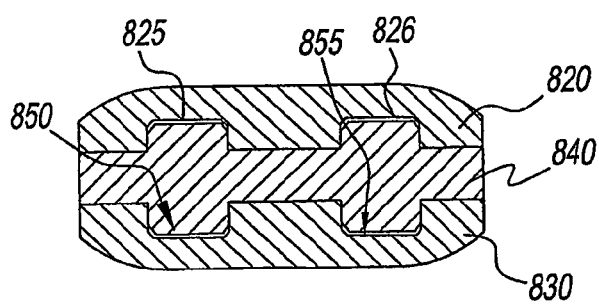
FIG. 38 is a first cross-sectional view of the pharmaceutical product of FIG. 36.

Referring to FIGS. 34 and 35, a fourteenth embodiment of the pharmaceutical product is shown and generally referred to by reference numeral 700'. Product 700' has features similar to product 700 and utilizes a snap-fit engagement of the upper, lower and middle portions 720', 730' and 740' based upon a plurality of concentrically aligned annular rings and grooves. The extent of the first and second locking rings 721', 741', 722' and 742' and/or the depth of the first and second annular recesses 743', 733', 744' and 734' is reduced as compared to product 700 so that annular gaps 750 and 755 exist between the components. These annular gaps 750 and 755 ensure that the first and second locking rings 721', 741', 722' and 742 are able to completely engage.

Referring to FIGS. 36 through 39, a fifteenth embodiment of the pharmaceutical product is shown and generally referred to by reference numeral 800. Product 800 has an upper portion 820, a lower portion 830 and a middle portion 840 that form three distinct components, which can be formed by tablet compression.

Product 800 has features similar to that of product 600 and provides for mechanical interlocking of the middle portion 840 with the upper and lower portions 820 and 830 through a snap-fit engagement. To enhance the connection, additional connection methods, such as one of the bonding techniques described above, can also be used.

Product 800 has first and second hubs or projections 845 and 846 on opposing sides of middle portion 840 and corresponding first and second recesses 825, 826 and 835, 836 on upper and lower portions 820 and 830, respectively. The present invention also contemplates the use of other numbers of hubs and recesses for the engagement of the separate components of product 800. The first and second hubs 845 and 846 have a substantially circular shape while the first and second recesses 825, 826, 835, 836 have substantially square shapes, so that the sidewalls of the hubs do not completely abut the sidewalls of the recesses, as is evident in FIG. 37.

The hubs 845 and 846 and the recesses 825, 826, 835, 836 can also be connected based upon a friction fit, and/or adhesive or other bonding agents can be used to further improve the connection. The extent of the hubs 845 and 846 and the depth of the recesses 825, 826, 835, 836 are reduced as compared to product 600 so that gaps 850 and 855 exist between the components.

Figure 39:
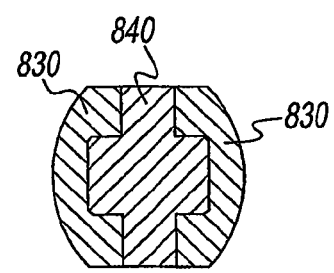
FIG. 39 is a second cross-sectional view of the pharmaceutical product of FIG. 36.
Figure 39A:
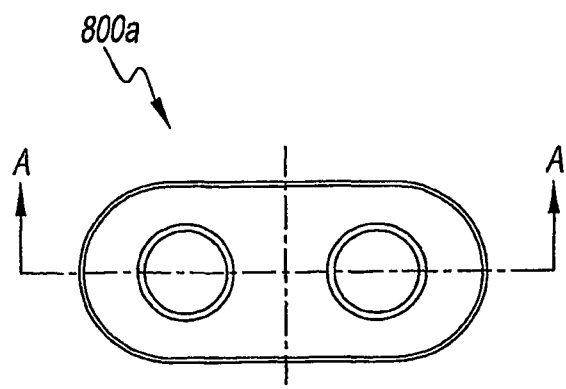
FIG. 39a is a plan view of an alternative embodiment of the pharmaceutical product of FIG. 36.
Figure 39B:
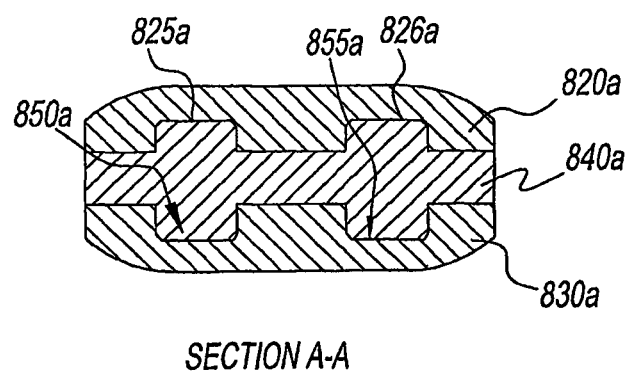

Referring to FIGS. 39a and 39b, an alternative embodiment of product 800 is shown and generally referred to by reference numeral 800a, which eliminates any gap between the mechanical interlocking portions. The hubs 845a and 846a and the recesses 825a, 826a, 835a, 836a have corresponding shapes, e.g., circular, with similar sizes, e.g., diameters, to allow for the snap-fit engagement and eliminate any gaps therein.

Figure 40:
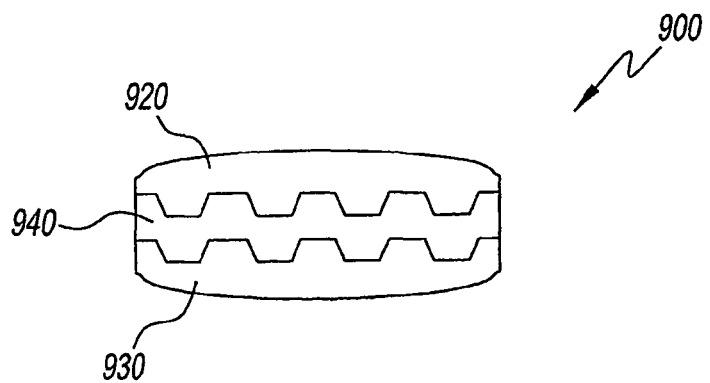
FIG. 40 is a plan view of a sixteenth embodiment of a pharmaceutical product of the present invention.
Figure 41:
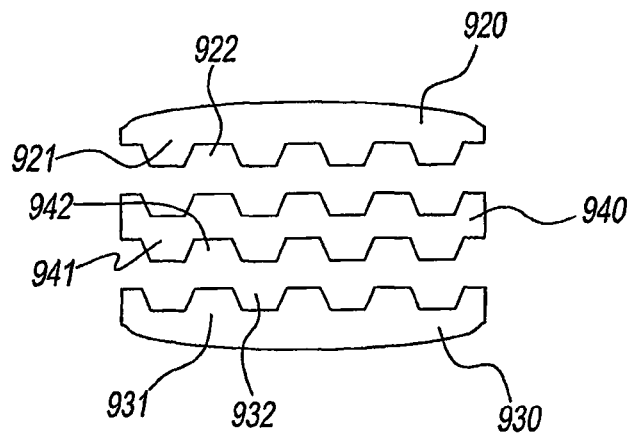
FIG. 41 is an exploded plan view of the pharmaceutical product of FIG. 40.
Figure 41A:
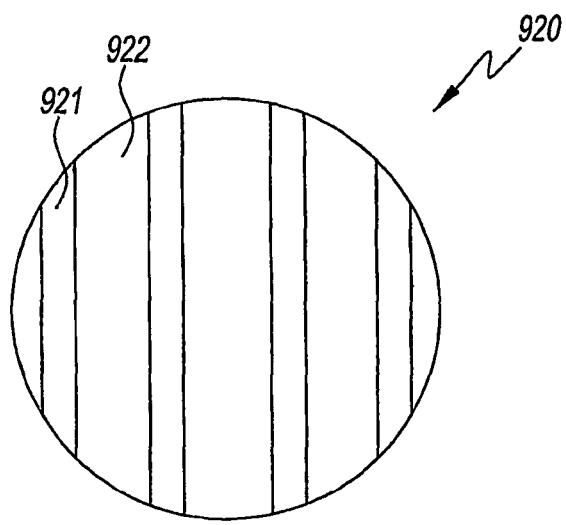
FIG. 41a is a plan view of the upper portion of the pharmaceutical product of FIG. 40.
Figure 42:
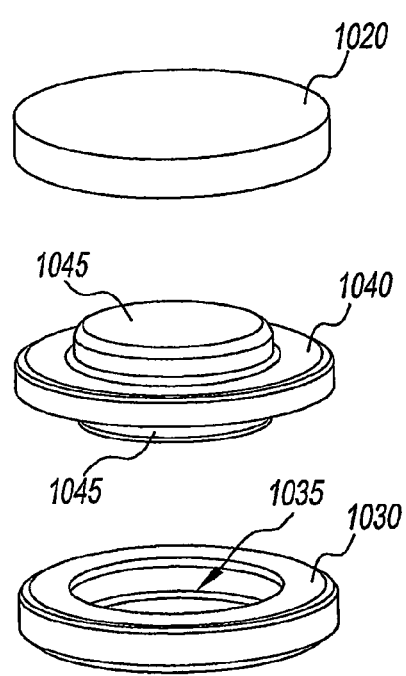
FIG. 42 is an exploded perspective view of a seventeenth embodiment of a pharmaceutical product of the present invention.
Figure 43:
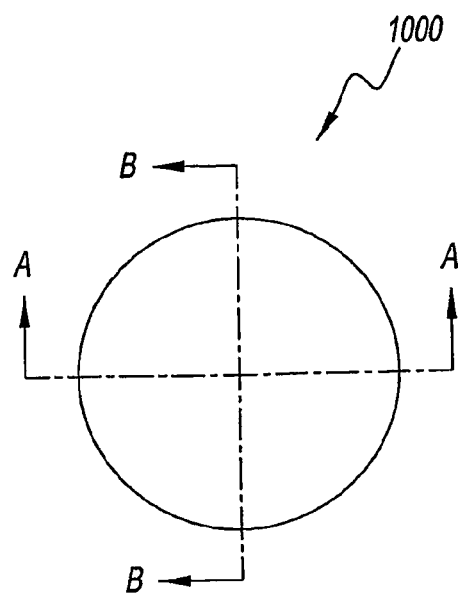
FIG. 43 is a plan view of the pharmaceutical product of FIG. 42.
Figure 44:
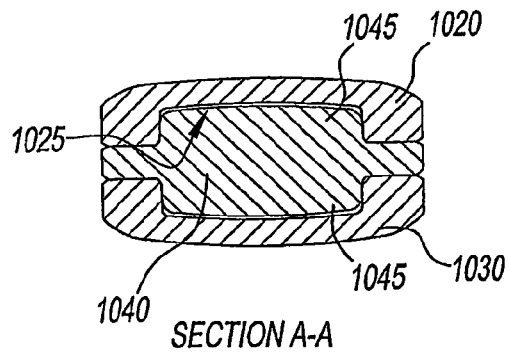
FIG. 44 is a first cross-sectional view of the pharmaceutical product of FIG. 42.
Figure 45:
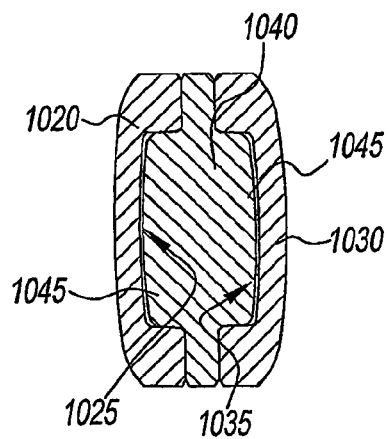
FIG. 45 is a second cross-sectional view of the pharmaceutical product of FIG. 42.
Figure 46:
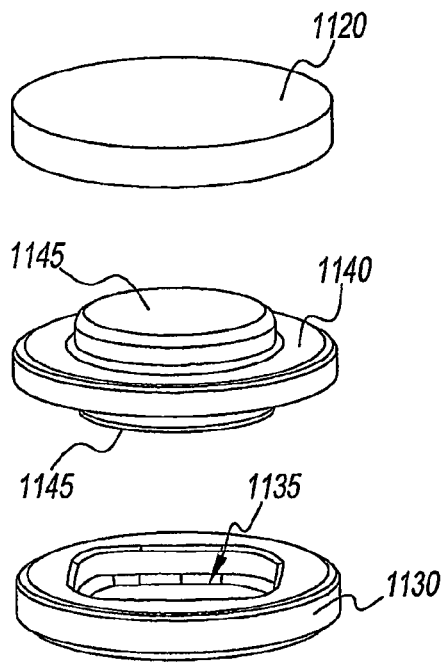
FIG. 46 is an exploded perspective view of an eighteenth embodiment of a pharmaceutical product of the present invention.
Figure 47:
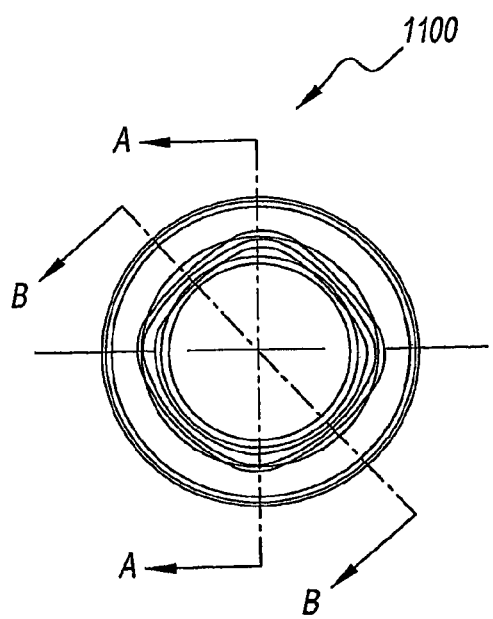
FIG. 47 is a plan view of the pharmaceutical product of FIG. 46.
Figure 48:
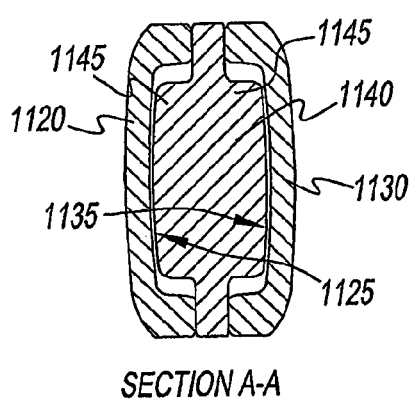
FIG. 48 is a first cross-sectional view of the pharmaceutical product of FIG. 46.
Figure 49:
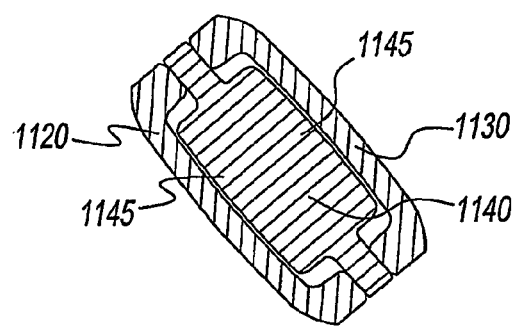
FIG. 49 is a second cross-sectional view of the pharmaceutical product of FIG. 46.
Figure 50:
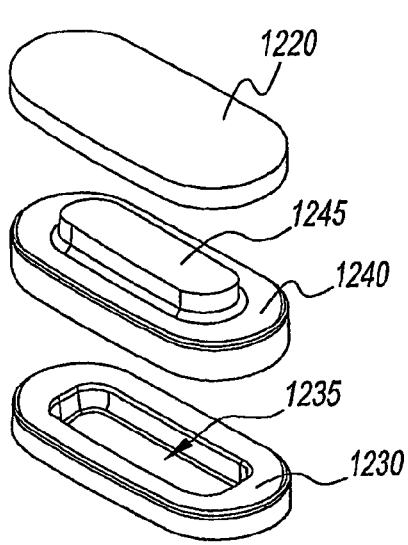
FIG. 50 is an exploded perspective view of a nineteenth embodiment of a pharmaceutical product of the present invention.
Figure 51:
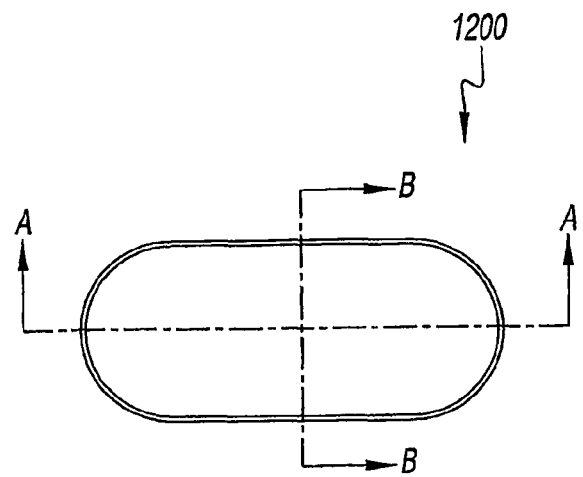
FIG. 51 is a plan view of the pharmaceutical product of FIG. 50.
Figure 52:
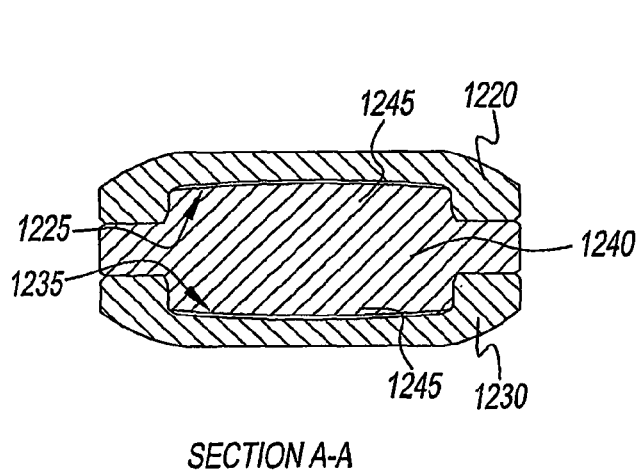
FIG. 52 is a first cross-sectional view of the pharmaceutical product of FIG. 50.
Figure 53:
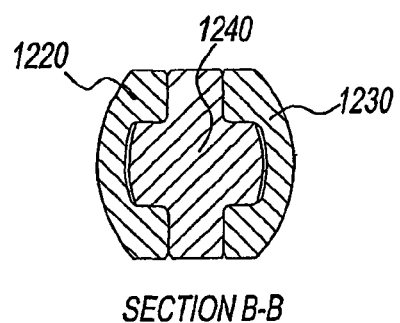
FIG. 53 is a second cross-sectional view of the pharmaceutical product of FIG. 50.

Referring to FIGS. 40 through 41a, a sixteenth embodiment of the pharmaceutical product is shown and generally referred to by reference numeral 900. Product 900 has an upper portion 920, a lower portion 930 and a middle portion 940 that form three distinct components, which can be formed by tablet compression.

Similar to the components of the embodiments described above, the upper, lower and middle portions 920, 930 and 940 are independently formulated to achieve a desired rate of release, e.g., a medium rate, a slow rate and an immediate rate, can include excipients to control the release rates, and can also be coated to further control the release rates. The upper, lower and middle portions 920, 930 and 940 all remain exposed, which allows for release of the active agent for all three of the portions.

Product 900 provides for mechanical interlocking of the middle portion 940 with the upper and lower portions 920 and 930 through a series of alternating rows of ridges and channels. Upper portion 920 has alternating ridges and channels 921 and 922 and lower portion 930 has alternating ridges and channels 931 and 932 that mate with corresponding alternating ridges 941 and 942 on opposing sides of middle portion 940.

To enhance the connection, additional connection methods, such as one of the bonding techniques described above, can also be used. The alternating ridges and channels 921, 922, 931, 932, 941 and 942 can traverse the upper, lower and middle portions 920, 930 and 940, respectively, or can be discretely disposed along the three portions so as to form a pattern of dimples and holes that are engageable. The alternating ridges and channels 921, 922, 931, 932, 941 and 942 are tapered to facilitate engagement between the upper, lower and middle portions 920, 930 and 940.

Referring to FIGS. 42 through 45, a seventeenth embodiment of the pharmaceutical product is shown and generally referred to by reference numeral 1000. Product 1000 has an upper portion 1020, a lower portion 1030 and a middle portion 1040 that form three distinct components, which can be formed by tablet compression.

Similar to the components of the embodiments described above, the upper, lower and middle portions 1020, 1030 and 1040 are independently formulated to achieve a desired rate of release, e.g., a medium rate, a slow rate and an immediate rate, and can include excipients to control the release rates, or could instead or optionally include and additional coated to further vary or control the release rates of the active agents. The upper, lower and middle portions 1020, 1030 and 1040 all remain exposed, which allows for release of the active agent for all three of the portions.

Product 1000 provides for mechanical interlocking of the middle portion 1040 with the upper and lower portions 1020 and 1030 through center hubs or projections 1045 on opposing sides of middle portion 1040 and corresponding center recesses 1025 and 1035 on upper and lower portions 1020 and 1030, respectively. The center hubs 1045 have a substantially circular shape that correspond to the circular shape of the center recesses 1025 and 1035. The edges of the center hubs 1045 are also preferably chamfered to facilitate assembly.

The center hubs 1045 and the center recesses 1025 and 1035 can also be connected based upon a friction fit, and/or adhesive or other bonding agents can be used to further improve the connection.

Referring to FIGS. 46 through 49, an eighteenth embodiment of the pharmaceutical product is shown and generally referred to by reference numeral 1100. Product 1100 has an upper portion 1120, a lower portion 1130 and a middle portion 1140 that form three distinct components, which can be formed by tablet compression.

Similar to the components of the embodiments described above, the upper, lower and middle portions 1120, 1130 and 1140 are independently formulated to achieve a desired rate of release, e.g., a medium rate, a slow rate and an immediate rate, can include excipients to control the release rates, and can also be coated to further control the release rates. The upper, lower and middle portions 1120, 1130 and 1140 all remain exposed, which allows for release of the active agent for all three of the portions.

Product 1100 provides for mechanical interlocking of the middle portion 1140 with the upper and lower portions 1120 and 1130 through center hubs or projections 1145 on opposing sides of middle portion 1140 and corresponding center recesses 1125 and 1135 on upper and lower portions 1120 and 1130, respectively. The center hubs 1145 have a substantially circular shape, while the center recesses 1125 and 1135 have a substantially square shape, so that the sidewalls of the hubs do not completely abut the sidewalls of the recesses, as is evident in FIG. 48. The edges of the center hubs 1145 can be chamfered to facilitate assembly.

The center hubs 1145 and the center recesses 1125 and 1135 can also be connected based upon a friction fit, and/or adhesive or other bonding agents can be used to further improve the connection.

Referring to FIGS. 50 through 53, a nineteenth embodiment of the pharmaceutical product is shown and generally referred to by reference numeral 1200. Product 1200 has an upper portion 1220, a lower portion 1230 and a middle portion 1240 that form three distinct components, which can be formed by tablet compression.

Similar to the components of the embodiments described above, the upper, lower and middle portions 1220, 1230 and 1240 are independently formulated to achieve a desired rate of release, e.g., a medium rate, a slow rate and an immediate rate, can include excipients to control the release rates, and can also be coated to further control the release rates. The upper, lower and middle portions 1220, 1230 and 1240 all remain exposed, which allows for release of the active agent for all three of the portions.

Product 1200 provides for mechanical interlocking of the middle portion 1240 with the upper and lower portions 1220 and 1230 through center hubs or projections 1245 on opposing sides of middle portion 1240 and corresponding center recesses 1225 and 1235 on upper and lower portions 1220 and 1230, respectively. The center hubs 1245 have a substantially circular shape that correspond to the circular shape of the center recesses 1225 and 1235. The edges of the center hubs 1245 are also preferably chamfered to facilitate assembly via a snap fit.

The center hubs 1245 and the center recesses 1225 and 1235 can also be connected based upon a friction fit, and/or adhesive or other bonding agents can be used to further improve the connection.

Referring to FIGS. 54 through 57, a twentieth embodiment and a first preferred embodiment of the pharmaceutical product is shown and generally referred to by reference numeral 1300. Product 1300 has an upper portion 1320, a lower portion 1330 and a middle portion 1340 that form three distinct components, which can be formed by tablet compression.

Similar to the components of the embodiments described above, the upper, lower and middle portions 1320, 1330 and 1340 are independently formulated to achieve a desired rate of release, e.g., a medium rate, a slow rate and an immediate rate, can include excipients to control the release rates, and can also be coated to further control the release rates. The upper, lower and middle portions 1320, 1330 and 1340 all remain exposed, which allows for release of the active agent for all three of the portions.

The upper, lower and middle portions 1320, 1330 and 1340 can be connected through various methods, such as, for example, glues or adhesives; polymers; waxes; mechanical methods, structures or means; by application of energy; and any combination of such methods, including the methods described above with respect to the other embodiments and/or other methods, structures or binding ingredients that facilitate or strengthen the connection between the portions.

To facilitate the connection method used and strengthen the bond therebetween, upper and lower portions 1320 and 1330 have center projections 1325 and 1335, respectively that fit with corresponding (size and shape) center recesses 1345 on opposing sides of middle portion 1340. The hour-glass like shapes of each of the portions improve strength along the lateral direction of the product 1300. Of course, the male-female arrangement between the individual components can be reversed and still provide for improved strength. Gaps 1360 are formed along the periphery of the product 1300 between the middle portion 1340 and the upper and lower portions 1320, 1330. Gaps 1360 ensure that center projections 1325 and 1335 are completely inserted into, and in contact with, center recesses 1345.

Figure 57A:
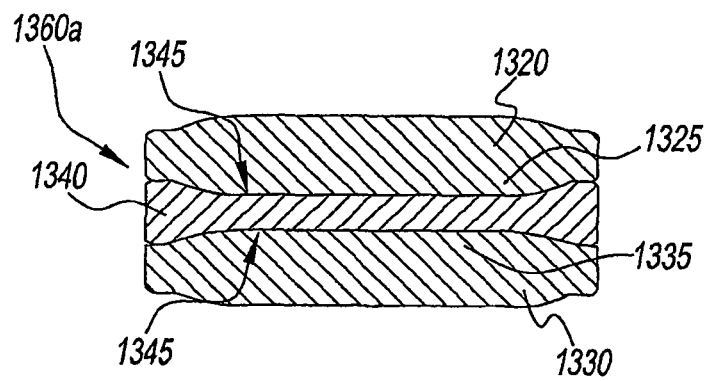
FIG. 57a is a cross-sectional view of an alternative embodiment of the pharmaceutical product of FIG. 54.
Figure 57A:
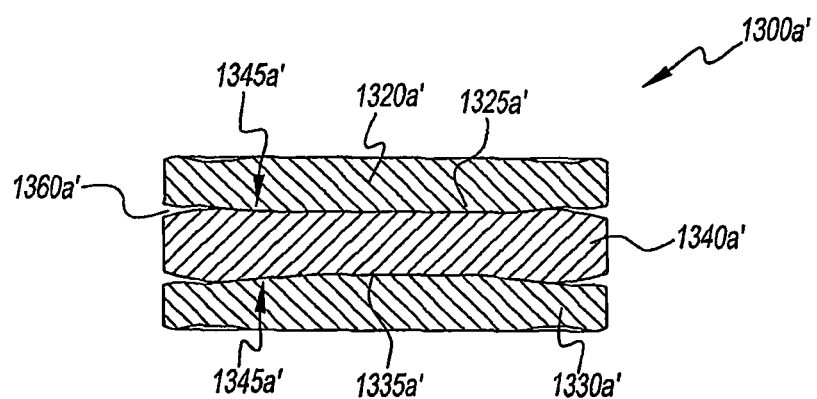

Referring to FIG. 57*a*, an alternative embodiment of the product of FIGS. 54 through 57 is shown in cross-section and generally referred to by reference numeral 1300*a*. Product 1300*a* is similar to product 1300 but the gaps 1360 are eliminated to form a flush abutment of the middle portion 1340 with the upper and lower portions 1320, 1330 along lands 1360*a*.

Referring to FIGS. 54' through 57', a second preferred embodiment of the pharmaceutical product is shown and generally referred to by reference numeral 1300'. Product 1300' has an upper portion 1320', a lower portion 1330' and a middle portion 1340' that form three distinct components, which can be formed by tablet compression.

Similar to the components of the embodiments described above, the upper, lower and middle portions 1320', 1330' and 1340' are independently formulated to achieve a desired rate of release, e.g., a medium rate, a slow rate and an immediate rate, can include excipients to control the release rates, and can also be coated to further control the release rates. The upper, lower and middle portions 1320', 1330' and 1340' all remain exposed, which allows for release of the active agent for all three of the portions, and have an ellipsoidal-like shape.

The upper, lower and middle portions 1320', 1330' and 1340' can be connected through various methods, such as, for example, glues or adhesives; polymers; waxes; mechanical methods, structures or means; by application of energy; and any combination of such methods, including the methods described above with respect to the other embodiments and/or other methods, structures or binding ingredients that facilitate or strengthen the connection between the portions.

To facilitate the connection method used and strengthen the bond therebetween, upper and lower portions 1320' and 1330' have center projections 1325' and 1335', respectively that fit with corresponding (size and shape) center recesses 1345' on opposing sides of middle portion 1340'. The hour-glass like shapes of each of the portions improve strength along the lateral direction of the product 1300. Of course, the male-female arrangement between the individual components can be reversed and still provide for improved strength. Angled lands 1360' are formed along the periphery of the product 1300' between the middle portion 1340' and the upper and lower portions 1320', 1330'. Lands 1360' facilitate assembly by providing a resistance against sliding for the upper, lower and middle portions 1320', 1330' and 1340'. The angle of the lands 1360' can be chosen to facilitate the assembly and to select the amount of resistance to sliding.

Referring to FIG. 57*a*', an alternative embodiment of the product of FIGS. 54' through 57' is shown in cross-section and generally referred to by reference numeral 1300*a*'. Product 1300*a*' is similar to product 1300' but the angled lands 1360' are eliminated to form gaps 1360*a*' along the periphery of the product 1300*a*' between the middle portion 1340*a*' and the upper and lower portions 1320*a*', 1330*a*'. Gaps 1360*a*' ensure that center projections 1325*a*' and 1335*a*' are completely inserted into, and in contact with, center recesses 1345*a'*.

Referring to FIGS. 58 through 61, a twenty-first embodiment and third preferred embodiment of the pharmaceutical product is shown and generally referred to by reference numeral 1400. Product 1400 has an upper portion 1420, a lower portion 1430 and a middle portion 1440 that form three distinct components, which can be formed by tablet compression.

Similar to the components of the embodiments described above, the upper, lower and middle portions 1420, 1430 and 1440 are independently formulated to achieve a desired rate of release, e.g., a medium rate, a slow rate and an immediate rate, can include excipients to control the release rates, and can also be coated to further control the release rates. The upper, lower and middle portions 1420, 1430 and 1440 all remain exposed, which allows for release of the active agent for all three of the portions, and have a circular shape.

The upper, lower and middle portions 1420, 1430 and 1440 can be connected through various methods, such as, for example, glues or adhesives; polymers; waxes; mechanical methods, structures or means; by application of energy; and any combination of such methods, including the methods described above with respect to the other embodiments and/or other methods, structures or binding ingredients that facilitate or strengthen the connection between the portions.

To facilitate the connection method used and strengthen the bond therebetween, upper and lower portions 1420 and 1430 have center projections 1425 and 1435, respectively that fit with corresponding (size and shape) center recesses 1445 on opposing sides of middle portion 1440. The hour-glass like shapes of each of the portions improve strength along the lateral direction of the product 1400. Of course, the male-female arrangement between the individual components can be reversed and still provide for improved strength. Lands 1460 are formed along the periphery of the product 1400 between the middle portion 1440 and the upper and lower portions 1420, 1430. Lands 1460 facilitate assembly by providing a seat to reduce sliding of the upper, lower and middle portions 1420, 1430 and 1440. The lands 1460 are substantially planar along a horizontal direction.

Referring to FIG. 61*a*, an alternative embodiment of the product of FIGS. 58 through 61 is shown in cross-section and generally referred to by reference numeral 1400*a*. Product 1400*a* is similar to product 1400 but the lands 1460*a* are set at an angle from the horizontal. The lands 1460*a* provide resistance to sliding between the upper, lower and middle portions 1420, 1430 and 1440.

Referring to FIG. 61*b*, an alternative embodiment of the product of FIGS. 58 through 61 is shown in cross-section and generally referred to by reference numeral 1400*b*. Product 1400*b* is similar to product 1400 but the lands are eliminated so that the concave faces of middle portion 1440 fit closely against the convex faces of upper and lower portions 1420 and 1430.

Referring to FIG. 61*c*, an alternative embodiment of the product of FIGS. 58 through 61 is shown in cross-section and generally referred to by reference numeral 1400*c*. Product 1400*c* is similar to product 1400 but the angled lands are eliminated to form gaps 1460*c* along the periphery of the product 1400 between the middle portion 1440 and the upper and lower portions 1420, 1430. Gaps 1460*c* ensure that center projections 1425 and 1435 are completely inserted into and in contact with center recesses 1445.

Figure 61D:
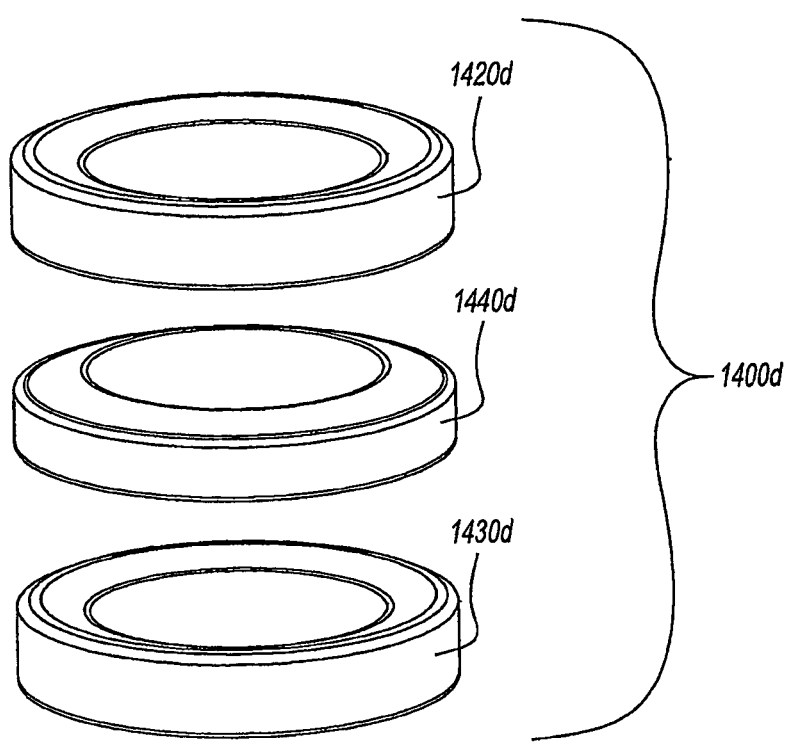
FIG. 61d is an exploded view of another alternative embodiment of the pharmaceutical product of FIG. 58.

Referring to FIG. 61*d*, an alternative embodiment of the product of FIGS. 58 through 61 is shown in an exploded view and generally referred to by reference numeral 1400*d*. Product 1400*d* is similar to product 1400 but the concavity and convexity of the upper, lower and middle portions 1420*d*, 1430*d* and 1440*d* is reversed.

Referring to FIGS. 62 through 65, a twenty-second embodiment of the pharmaceutical product is shown and generally referred to by reference numeral 1500. Product 1500 has a connection structure 1510, an upper portion 1520, a lower portion 1530, and a middle portion 1540 that form four distinct components, which can be formed by tablet compression.

Similar to the components of the embodiments described above, the connection structure 1510 and upper, lower and middle portions 1520, 1530 and 1540 are independently formulated to achieve a desired rate of release, e.g., a medium rate, a slow rate and an immediate rate, can include excipients to control the release rates, and can also be coated to further control the release rates. The upper, lower and middle portions 1520, 1530 and 1540 all remain exposed, which allows for release of the active agent for all three of the portions.

Product 1500 provides for a mechanical interlocking of the middle portion 1540 with the upper and lower portions 1520 and 1530 through the connection structure or rivet 1510. The upper, lower and middle portions 1520, 1530 and 1540 each have center holes 1525, 1535 and 1545, respectively, that are sized to receive the shaft 1512 of rivet 1510. Preferably, the rivet shaft 1512 has a tapered distal end 1514 to facilitate assembly of the rivet with the upper, lower and middle portions 1520, 1530 and 1540. The rivet 1510 can have a rivet head 1515 or other locking structure for locking the components of the product 1500 together, such as, for example, by heat melt. Mechanical connections can also be used such as, for example, a ratchet lock. Adhesive or other bonding agents can also further be used to improve the connection. The rivet 1510 provides for connection of the components but can also have an active agent, which would provide for a fourth active component. The upper and lower portions 1520 and 1530 can have different diameters from the middle portion 1540 to further expose the different components.

Referring to FIGS. 66 through 69, a twenty-third embodiment of the pharmaceutical product is shown and generally referred to by reference numeral 1600. Product 1600 has a connection structure 1610, an upper portion 1620, a lower portion 1630, and a middle portion 1640 that form four distinct components, which can be formed by tablet compression.

Similar to the components of the embodiments described above, the connection structure 1610 and upper, lower and middle portions 1620, 1630 and 1640 are independently formulated to achieve a desired rate of release, e.g., a medium rate, a slow rate and an immediate rate, can include excipients to control the release rates, and can also be coated to further control the release rates. The upper, lower and middle portions 1620, 1630 and 1640 all remain exposed, which allows for release of the active agent for all three of the portions.

Product 1600 provides for a mechanical interlocking of the middle portion 1640 with the upper and lower portions 1620 and 1630 through the connection structure or rivet 1610. The upper, lower and middle portions 1620, 1630 and 1640 each have center holes 1625, 1635 and 1645, respectively, that are sized to receive the shaft 1612 of rivet 1610. Preferably, the rivet shaft 1612 has a tapered distal end 1614 to facilitate assembly of the rivet with the upper, lower and middle portions 1620, 1630 and 1640. The rivet 1610 can have a rivet head 1615 or other locking structure for locking the components of the product 1600 together, such as, for example, by hot melt or by a mechanical connection, such as, for example, threads. Adhesive or other bonding agents can also be used to further improve the connection. The rivet 1610 provides for connection of the components but can also have an active agent, which would provide for a fourth active component. The upper and lower portions 1620 and 1630 can have different diameters from the middle portion 1640 to further expose the different components.

Referring to FIGS. 70 and 71, a twenty-fourth embodiment of the pharmaceutical product is shown and generally referred to by reference numeral 1700. Product 1700 has an outer portion 1720, an upper portion 1730 and a lower portion 1740 that form three distinct components, which can be formed by tablet compression.

Similar to the components of the embodiments described above, the outer, upper and lower portions 1720, 1730 and 1740 are independently formulated to achieve a desired rate of release, e.g., a medium rate, a slow rate and an immediate rate, can include excipients to control the release rates, and can also be coated to further control the release rates. The outer, upper and lower portions 1720, 1730 and 1740 all remain exposed, which allows for release of the active agent for all three of the portions.

Product 1700 provides for an adhesive bond of the upper and lower portions 1730 and 1740. To enhance the connection, additional connection methods, such as one of the bonding techniques described above, can also be used.

The outer portion 1720 is connected to the upper and lower portions 1730 and 1740 with an inwardly depending flange 1750. The flange 1750 provides a mechanical connection or lock to the upper and lower portions 1730 and 1740 and prevents them from sliding through the outer portion 1720.

The flange 1750 may circumscribe the entire inner opening 1725 of the outer portion 1720 or may be one or more projections that extend into the inner opening. The size and shape of flange 1750, e.g., a tapered flange, can be chosen to facilitate assembly, as well as provide increased strength. The upper and lower portions 1730 and 1740 can have corresponding shapes, e.g., tapers to facilitate assembly. Assembly of product 1700 is by positioning of lower portion 1740 in inner opening 1725 of outer portion 1720 followed by application of the adhesive or other bonding agent 1760 and then pressing or moving the upper portion 1730 into position.

Referring to FIGS. 72 and 73, a twenty-fifth embodiment of the pharmaceutical product is shown and generally referred to by reference numeral 1800. Product 1800 has an outer portion 1820, an upper portion 1830 and a lower portion 1840 that form three distinct components, which can be formed by tablet compression.

Similar to the components of the embodiments described above, the outer, upper and lower portions 1820, 1830 and 1840 are independently formulated to achieve a desired rate of release, e.g., a medium rate, a slow rate and an immediate rate, can include excipients to control the release rates, and can also be coated to further control the release rates. The outer, upper and lower portions 1820, 1830 and 1840 all remain exposed, which allows for release of the active agent for all three of the portions.

Product 1800 provides for an adhesive bond of the upper and lower portions 1830 and 1840 with the center rib 1850 of the outer portion 1820. To enhance the connection, additional connection methods, such as one of the bonding techniques described above, can also be used.

The center rib 1850 may cover the entire inner opening 1825 of the outer portion 1820 or may be one or more cross-ribs that extend across the inner opening. The size and shape of center rib 1850, e.g., a rough surface to enhance bonding, can be chosen to facilitate assembly, as well as provide increased strength. Assembly of product 1800 is by application of the adhesive or other bonding agent 1860 into the two inner openings 1825 which are defined by center rib 1850 and then pressing or moving the upper and lower portions 1830 and 1840 into position. Where center rib 1850 covers the entire opening 1825, this has the added advantage of isolating the upper portion 1830 from the lower portion 1840, such as, for example, where incompatible active agents and/or ingredients need to be isolated from each other.

Referring to FIG. 74, a twenty-sixth embodiment of the pharmaceutical product is shown and generally referred to by reference numeral 1900. Product 1900 has an outer portion 1920, an upper portion 1930 and a lower portion 1940 that form three distinct components, which can be formed by tablet compression.

Similar to the components of the embodiments described above, the outer, upper and lower portions 1920, 1930 and 1940 are independently formulated to achieve a desired rate of release, e.g., a medium rate, a slow rate and an immediate rate, can include excipients to control the release rates, and can also be coated to further control the release rates. The outer, upper and lower portions 1920, 1930 and 1940 all remain exposed, which allows for release of the active agent for all three of the portions.

Product 1900 provides for an adhesive bond of the upper and lower portions 1930 and 1940 with each other and with the walls that define the inner opening of the outer portion 1920. To enhance the connection, additional connection methods, such as one of the bonding techniques described above, can also be used.

Assembly of product 1900 is by application of the adhesive or other bonding agent into the inner opening and then pressing or moving the upper and lower portions 1930 and 1940 into position.

Referring to FIG. 75, a twenty-seventh embodiment of the pharmaceutical product is shown and generally referred to by reference numeral 2000. Product 2000 has an upper portion 2020, a middle portion 2030 and a lower portion 2040 that form three distinct components, which can be formed by tablet compression.

Similar to the components of the embodiments described above, the upper, middle and lower portions 2020, 2030 and 2040 are independently formulated to achieve a desired rate of release, e.g., a medium rate, a slow rate and an immediate rate, can include excipients to control the release rates, and can also be coated to further control the release rates. The upper, middle and lower portions 2020, 2030 and 2040 all remain exposed, which allows for release of the active agent for all three of the portions.

Product 2000 provides for an adhesive bond 2060 between the upper and lower portions 2020 and 2040 and the middle portion 2030, the thickness of which can vary. To enhance the connection, additional connection methods, such as one of the bonding techniques described above, can also be used.

Figure 76A:
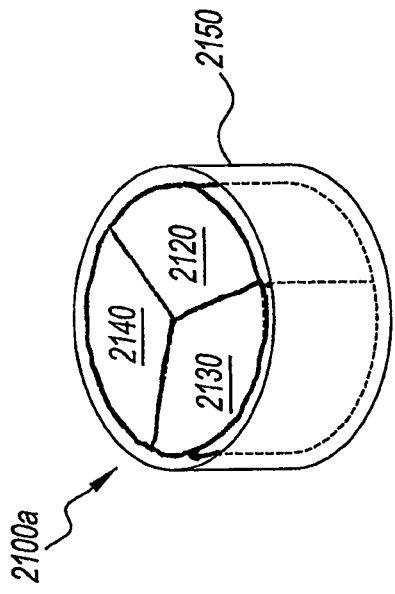
FIG. 76a is a perspective view of an alternative embodiment of the pharmaceutical product of FIG. 76.
Figure 76:
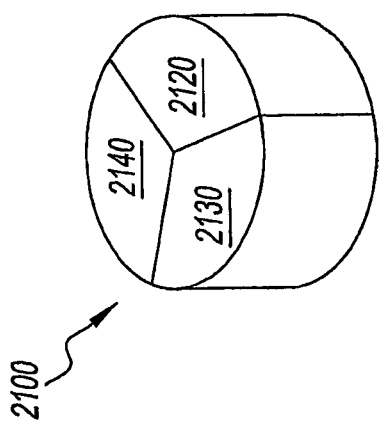
FIG. 76 is a perspective view of a twenty-eighth embodiment of a pharmaceutical product of the present invention.

Referring to FIG. 76, a twenty-eighth embodiment of the pharmaceutical product is shown and generally referred to by reference numeral 2100. Product 2100 has a first portion 2120, a second portion 2130 and a third portion 2140 that form three distinct components, which can be formed by tablet compression. The present disclosure also contemplates different numbers of portions from the embodiment of FIG. 76.

Similar to the components of the embodiments described above, the first, second and third portions 2120, 2130 and 2140 are independently formulated to achieve a desired rate of release, e.g., a medium rate, a slow rate and an immediate rate, can include excipients to control the release rates, and can also be coated to further control the release rates. The first, second and third portions 2120, 2130 and 2140 all remain exposed, which allows for release of the active agent for all three of the portions.

Product 2100 provides for an adhesive bond between the first, second and third portions 2120, 2130 and 2140 along inner walls of each portion. To enhance the connection, additional connection methods, such as one of the bonding techniques described above, can also be used.

Referring to FIG. 76*a*, an alternative embodiment of product 2100 is shown and generally referred to by reference numeral 2100*a*. Product 2100*a* has first portion 2120, second portion 2130 and third portion 2140 housed in a cup-like housing 2150. The cup-like housing 2150 can also isolate one or more of the first, second and third portions 2120, 2130 and 2140 through use of isolating walls (not shown) traversing the inner volume of the housing. The number of portions that are used with the cup-like housing 2150 can be varied. Additionally, placebos can be used to fill open slots within the cup-like housing 2150 such as, for example, if only the active agents of first portion 2120 and second portion 2130 are to be delivered.

Figure 77:
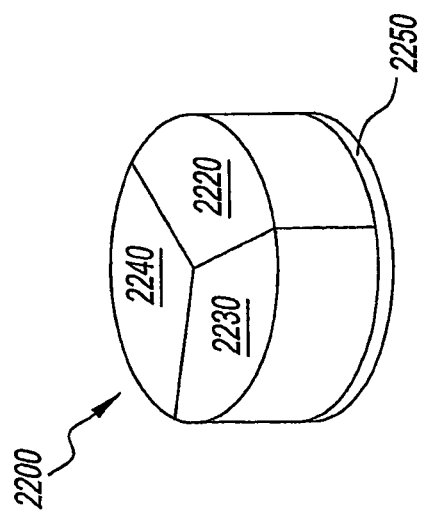
FIG. 77 is a perspective view of a twenty-ninth embodiment of a pharmaceutical product of the present invention.

Referring to FIG. 77, a twenty-ninth embodiment of the pharmaceutical product is shown and generally referred to by reference numeral 2200. Product 2200 has a first portion 2220, a second portion 2230 and a third portion 2240 that form three distinct components, which can be formed by tablet compression.

Similar to the components of the embodiments described above, the first, second and third portions 2220, 2230 and 2240 are independently formulated to achieve a desired rate of release, e.g., a medium rate, a slow rate and an immediate rate, can include excipients to control the release rates, and can also be coated to further control the release rates. The first, second and third portions 2220, 2230 and 2240 all remain exposed, which allows for release of the active agent for all three of the portions.

Product 2200 provides for an adhesive bond between the first, second and third portions 2220, 2230 and 2240 and a base 2250. Additionally, the first, second and third portions 2220, 2230 and 2240 can be bonded to each other along inner walls of each portion. To enhance the connection, additional connection methods, such as one of the bonding techniques described above, can also be used. Also, mechanical connection structures can also be provided between the base 2250 and the first, second and third portions 2220, 2230 and 2240 to increase the connection strength, such as, for example, tongue and grooves.

Figure 78:
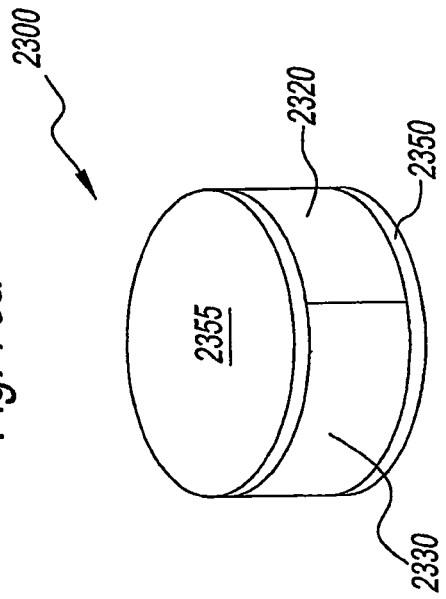
FIG. 78 is a perspective view of a thirtieth embodiment of a pharmaceutical product of the present invention.

Referring to FIG. 78, a thirtieth embodiment of the pharmaceutical product is shown and generally referred to by reference numeral 2300. Product 2300 has a first portion 2320, a second portion 2330 and a third portion (not shown) that form three distinct components, which can be formed by tablet compression.

Similar to the components of the embodiments described above, the first, second and third portions 2320 and 2330 are independently formulated to achieve a desired rate of release, e.g., a medium rate, a slow rate and an immediate rate, can include excipients to control the release rates, and can also be coated to further control the release rates. The first, second and third portions 2320 and 2330 all remain exposed, which allows for release of the active agent for all three of the portions.

Product 2300 provides for an adhesive bond between the first, second and third portions 2320 and 2330 and a base 2350 and a top 2355. Additionally, the first, second and third portions 2320 and 2330 can be bonded to each other along inner walls of each portion. To enhance the connection, additional connection methods, such as one of the bonding techniques described above, can also be used. Also, mechanical connection structures can also be provided between the base 2350 and/or top 2355 and the first, second and third portions 2320 and 2330 to increase the connection strength, such as, for example, tongue and grooves.

Referring to FIG. 79, a thirty-first embodiment of the pharmaceutical product is shown and generally referred to by reference numeral 2400. Product 2400 has a connection structure 2410, an upper portion 2420, a lower portion 2430, and a middle portion 2440 that form four distinct components, which can be formed by tablet compression.

Similar to the components of the embodiments described above, the connection structure 2410 and upper, lower and middle portions 2420, 2430 and 2440 are independently formulated to achieve a desired rate of release, e.g., a medium rate, a slow rate and an immediate rate, can include excipients to control the release rates, and can also be coated to further control the release rates. The upper, lower and middle portions 2420, 2430 and 2440 all remain exposed, which allows for release of the active agent for all three of the portions.

Product 2400 provides for a mechanical interlocking of the middle portion 2440 with the upper and lower portions 2420 and 2430 through the connection structure or rivet 2410. The upper, lower and middle portions 2420, 2430 and 2440 each have center holes that are sized to receive the upper shaft 2412 of the rivet 2410 and the lower shaft 2413 of the rivet lock 2415. Preferably, the rivet shaft 2412 has a tapered distal end 2414 to facilitate assembly of the rivet with the upper, lower and middle portions 2420, 2430 and 2440. The rivet 2410 has a rivet lock 2415 or other locking structure for locking the components of the product 2400 together, such as, for example, a ratchet lock or a fir-tree. Adhesive or other bonding agents can also be used to further improve the connection. The rivet 2410 provides for connection of the components but can also have an active agent, which would provide for a fourth active component. The upper and lower portions 2420 and 2430 can have different diameters from the middle portion 2440 to further expose the different components.

Referring to FIG. 80, a thirty-second embodiment of the pharmaceutical product is shown and generally referred to by reference numeral 2500. Product 2500 has a connection structure 2510, an upper portion 2520, a lower portion 2530, and a middle portion 2540 that form four distinct components, which can be formed by tablet compression.

Similar to the components of the embodiments described above, the connection structure 2510 and upper, lower and middle portions 2520, 2530 and 2540 are independently formulated to achieve a desired rate of release, e.g., a medium rate, a slow rate and an immediate rate, can include excipients to control the release rates, and can also be coated to further control the release rates. The upper, lower and middle portions 2520, 2530 and 2540 all remain exposed, which allows for release of the active agent for all three of the portions.

Product 2500 provides for a mechanical interlocking of the middle portion 2540 with the upper and lower portions 2520 and 2530 through the connection structure or rivet 2510. The upper, lower and middle portions 2520, 2530 and 2540 each have center holes 2525, 2535 and 2545, respectively, that are sized to receive the shaft 2512 of the rivet 2510. The rivet shaft 2512 has a tapered distal end 2514 to facilitate assembly of the rivet with the upper, lower and middle portions 2520, 2530 and 2540, and which can also be a fir-tree for connection. The center hole 2535 of the lower portion 2530 has a reduced diameter to provide a mechanical connection with the rivet 2510. Adhesive or other bonding agents can also be used to further improve the connection. The rivet 2510 provides for connection of the components but can also have an active agent, which would provide for a fourth active component.

Referring to FIG. 81, a thirty-third embodiment of the pharmaceutical product is shown and generally referred to by reference numeral 2600. Product 2600 has a connection structure 2610, an upper portion 2620, a lower portion 2630, and an outer portion 2640 that form four distinct components, which can be formed by tablet compression.

Similar to the components of the embodiments described above, the connection structure 2610 and upper, lower and outer portions 2620, 2630 and 2640 are independently formulated to achieve a desired rate of release, e.g., a medium rate, a slow rate and an immediate rate, can include excipients to control the release rates, and can also be coated to further control the release rates. The upper, lower and outer portions 2620, 2630 and 2640 all remain exposed, which allows for release of the active agent for all three of the portions.

Product 2600 provides for a mechanical interlocking of the outer portion 2640 with the upper and lower portions 2620 and 2630 through the connection structure or rivet 2610. The upper, lower and outer portions 2620, 2630 and 2640 each have center openings, grooves or orifices that are sized to receive the rivet 2510 and the rivet lock 2615. The rivet shaft 2612 has a tapered distal end 2614 to facilitate assembly of the rivet 2610 through the center opening of the outer portion 2640. The center opening of the outer portion 2640 can be defined by an inwardly depending flange 2650. The rivet 2610 has a rivet lock 2615 or other locking structure for locking the components of the product 2600 together, such as, for example, a ratchet lock or a fir-tree. Adhesive or other bonding agents can also be used to further improve the connection.

The rivet 2610 and the rivet lock 2615 can be connected to the upper and lower portions 2620 and 2630 via adhesive or other connection methods or structures as described herein. While the exemplary embodiment of FIG. 81 describes the rivet 2610 and the rivet lock 2615 embedded in the upper and lower portions 2620 and 2630, alternatively, they can be connected to the surface of these portions. The rivet 2610 provides for connection of the components but can also have an active agent, which would provide for a fourth active component. The upper and lower portions 2620 and 2630 can have different diameters from the middle portion 2640 to further expose the different components.

Referring to FIG. 82, a thirty-fourth embodiment of the pharmaceutical product is shown and generally referred to by reference numeral 2700. Product 2700 has a connection structure 2710, an upper portion 2720, a lower portion 2730, and a middle portion 2740 that form four distinct components, which can be formed by tablet compression.

Similar to the components of the embodiments described above, the connection structure 2710 and upper, lower and middle portions 2720, 2730 and 2740 are independently formulated to achieve a desired rate of release, e.g., a medium rate, a slow rate and an immediate rate, can include excipients to control the release rates, and can also be coated to further control the release rates. The upper, lower and middle portions 2720, 2730 and 2740 all remain exposed, which allows for release of the active agent for all three of the portions.

Product 2700 provides for a mechanical interlocking of the middle portion 2740 with the upper and lower portions 2720 and 2730 through the connection structure or rivet 2710. The upper, lower and middle portions 2720, 2730 and 2740 each have center openings that are sized to receive the rivet 2710. The rivet 2710 can be a hollow structure or have a channel 2750 formed therein. The rivet lock or head 2715 is connected to the rivet 2710 via hot melt. Adhesive or other bonding agents can also be used to further improve the connection.

The rivet 2710 provides for connection of the components but can also have an active agent, which would provide for a fourth active component. The upper and lower portions 2720 and 2730 can have different diameters from the middle portion 2740 to further expose the different components.

Referring to FIG. 83, a thirty-fifth embodiment of the pharmaceutical product is shown and generally referred to by reference numeral 2800. Product 2800 has a connection structure 2810, an upper portion 2820, a lower portion 2830, and a middle portion 2840 that form four distinct components, which can be formed by tablet compression.

Similar to the components of the embodiments described above, the connection structure 2810 and upper, lower and middle portions 2820, 2830 and 2840 are independently formulated to achieve a desired rate of release, e.g., a medium rate, a slow rate and an immediate rate, can include excipients to control the release rates, and can also be coated to further control the release rates. The upper, lower and middle portions 2820, 2830 and 2840 all remain exposed, which allows for release of the active agent for all three of the portions.

Product 2800 provides for a mechanical interlocking of the middle portion 2840 with the upper and lower portions 2820 and 2830 through the connection structure or flexible cord 2810. The upper, lower and middle portions 2820, 2830 and 2840 each have center openings that are sized to receive the flexible cord 2810. The flexible cord 2810 has cord heads 2815 at opposing ends and facilitates assembly due to its resiliency or flexibility. Adhesive or other bonding agents can also be used to further improve the connection. The flexible cord 2810 can be stretched during assembly to allow the upper, lower and middle portions 2820, 2830 and 2840 to be placed over the cord heads 2815. The flexible cord 2810 can also be injection molded into place in the center openings and the cord can alternatively be non-flexible.

The flexible cord 2810 provides for connection of the components but can also have an active agent, which would provide for a fourth active component. The upper and lower portions 2820 and 2830 can have different diameters from the middle portion 2840 to further expose the different components.

Referring to FIG. 84, a thirty-sixth embodiment of the pharmaceutical product is shown and generally referred to by reference numeral 2900. Product 2900 has a connection structure 2910, an upper portion 2920, a lower portion 2930, and a middle portion 2940 that form four distinct components, which can be formed by tablet compression.

Similar to the components of the embodiments described above, the connection structure 2910 and upper, lower and middle portions 2920, 2930 and 2940 are independently formulated to achieve a desired rate of release, e.g., a medium rate, a slow rate and an immediate rate, can include excipients to control the release rates, and can also be coated to further control the release rates. The upper, lower and middle portions 2920, 2930 and 2940 all remain exposed, which allows for release of the active agent for all three of the portions.

Product 2900 provides for a mechanical interlocking of the middle portion 2940 with the upper and lower portions 2920 and 2930 through the connection structure or rivet 2910. The upper, lower and middle portions 2920, 2930 and 2940 each have center openings that are sized to receive the rivet 2910. The rivet 2910 is a hollow structure or has a channel 2950 formed therein and can hold the upper, lower and middle portions 2920, 2930 and 2940 by friction fit or other mechanical connection methods or structures. Rivet heads 2915 can be formed on opposing ends of the rivet 2910 to further strengthen the connection. Adhesive or other bonding agents can also be used to further improve the connection. The rivet 2910 provides for connection of the components but can also have an active agent, which would provide for a fourth active component.

Referring to FIG. 85, a thirty-seventh embodiment and fourth preferred embodiment of the pharmaceutical product is shown and generally referred to by reference numeral 3000. Product 3000 has a connection structure 3010, as well as an upper portion 3020, a lower portion 3030, and a middle portion 3040 that form distinct components, which can be formed by tablet compression.

Similar to the components of the embodiments described above, the upper, lower and middle portions 3020, 3030 and 3040 are independently formulated to achieve a desired rate of release, e.g., a medium rate, a slow rate and an immediate rate, can include excipients to control the release rates, and can also be coated to further control the release rates. The upper, lower and middle portions 3020, 3030 and 3040 all remain exposed, which allows for release of the active agent for all three of the portions.

Product 3000 provides for a mechanical interlocking of the middle portion 3040 with the upper and lower portions 3020 and 3030 through the connection structure 3010. The connection structure 3010 is an open-ended capsule-like rigid or semi-rigid structure having a rounded closed end 3015. The upper, lower and middle portions 3020, 3030 and 3040 each have center openings that are sized to receive the connection structure 3010. The open end of the connection structure 3010 is hollow to allow for a pusher rod or other structure to slide the connection structure through the center openings of the upper, lower and middle portions 3020, 3030 and 3040. Although, the present invention contemplates the use of other connection structures and methods of positioning the connection structure 3010. Adhesive or other bonding agents can also be used to further improve the connection.

Alternatively, the connection structure 3010 can be an inflated membrane that facilitates assembly. The upper, lower and middle portions 3020, 3030 and 3040 each have center openings that are sized to receive the membrane. The membrane is a hollow structure or has a channel formed therein, which is inflatable and can hold the upper, lower and middle portions 3020, 3030 and 3040 by friction fit or other mechanical connection methods or structures. Membrane heads can be formed on opposing ends of the membrane to further strengthen the connection. Adhesive or other bonding agents can also be used to further improve the connection. The membrane provides for connection of the components but can also have an active agent, which would provide for a fourth active component.

Referring to FIG. 86, a thirty-eighth embodiment of the pharmaceutical product is shown and generally referred to by reference numeral 3160. Product 3100 has a connection structure 3110, as well as an upper portion 3120, a lower portion 3130, and a middle portion 3140 that form distinct components, which can be formed by tablet compression.

Similar to the components of the embodiments described above, the upper, lower and middle portions 3120, 3130 and 3140 are independently formulated to achieve a desired rate of release, e.g., a medium rate, a slow rate and an immediate rate, can include excipients to control the release rates, and can also be coated to further control the release rates. The upper, lower and middle portions 3120, 3130 and 3140 all remain exposed, which allows for release of the active agent for all three of the portions.

Product 3100 provides for a mechanical interlocking of the middle portion 3140 with the upper and lower portions 3120 and 3130 through the connection structure 3110. The connection structure 3110 is an expanding internal tube or stent that facilitates assembly. The upper, lower and middle portions 3120, 3130 and 3140 each have center openings that are sized to receive the stent 3110. The stent 3110 can hold the upper, lower and middle portions 3120, 3130 and 3140 by friction fit or other mechanical connection methods or structures. Stent heads 3115 can be formed on opposing ends of the stent 3110 to further strengthen the connection. Adhesive or other bonding agents can also be used to further improve the connection. The stent 3110 provides for connection of the components but can also have an active agent, which would provide for a fourth active component.

Referring to FIG. 87, a thirty-ninth embodiment of the pharmaceutical product is shown and generally referred to by reference numeral 3200. Product 3200 has a connection structure 3210, as well as an upper portion 3220, a lower portion 3230, and a middle portion 3240 that form distinct components, which can be formed by tablet compression.

Similar to the components of the embodiments described above, the upper, lower and middle portions 3220, 3230 and 3240 are independently formulated to achieve a desired rate of release, e.g., a medium rate, a slow rate and an immediate rate, can include excipients to control the release rates, and can also be coated to further control the release rates. The upper, lower and middle portions 3220, 3230 and 3240 all remain exposed, which allows for release of the active agent for all three of the portions.

Product 3200 provides for a mechanical interlocking of the middle portion 3240 with the upper and lower portions 3220 and 3230 through the connection structure 3210. The connection structure 3210 is a band that provides for assembly of upper, lower and middle portions 3220, 3230 and 3240. The band 3210 is large enough to fit over the assembled upper, lower and middle portions 3220, 3230 and 3240 and can then be secured in place, such as, for example, via heat-shrink or other contraction methods or structures. Adhesive or other bonding agents can also be used to further improve the connection. The band 3210 provides for connection of the components but can also have an active agent, which would provide for a fourth active component.

Referring to FIG. 88, a fortieth embodiment of the pharmaceutical product is shown and generally referred to by reference numeral 3300. Product 3300 has a connection structure 3310, as well as an upper portion 3320, a lower portion 3330, and a middle portion 3340 that form distinct components, which can be formed by tablet compression.

Similar to the components of the embodiments described above, the upper, lower and middle portions 3320, 3330 and 3340 are independently formulated to achieve a desired rate of release, e.g., a medium rate, a slow rate and an immediate rate, can include excipients to control the release rates, and can also be coated to further control the release rates. The upper, lower and middle portions 3320, 3330 and 3340 can all be exposed upon disintegration of the sleeve 3310 which allows for release of the active agent for all three of the portions or portions of the sleeve can have openings, e.g., at opposing ends of the sleeve for timed release.

Product 3300 provides for a mechanical interlocking of the middle portion 3340 with the upper and lower portions 3320 and 3330 through the connection structure 3310. The connection structure 3210 is a sleeve that provides for assembly of upper, lower and middle portions 3320, 3330 and 3340. The sleeve 3310 is large enough to fit over the assembled upper, lower and middle portions 3320, 3330 and 3340 and can then be secured in place, such as, for example, by being elastic, via heat-shrink or other contraction methods or structures. Adhesive or other bonding agents can also be used to further improve the connection. The sleeve 3310 provides for connection of the components but can also have an active agent, which would provide for a fourth active component.

Figure 89:
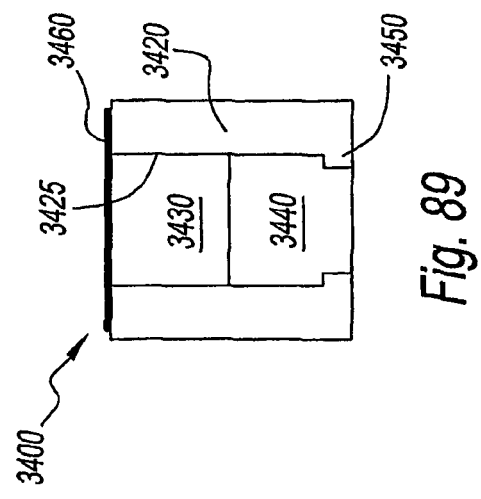
FIG. 89 is a cross-sectional view of a forty-first embodiment of a pharmaceutical product of the present invention.

Referring to FIG. 89, a forty-first embodiment of the pharmaceutical product is shown and generally referred to by reference numeral 3400. Product 3400 has an outer portion 3420, an upper portion 3430 and a lower portion 3440 that form three distinct components, which can be formed by tablet compression.

Similar to the components of the embodiments described above, the outer, upper and lower portions 3420, 3430 and 3440 are independently formulated to achieve a desired rate of release, e.g., a medium rate, a slow rate and an immediate rate, can include excipients to control the release rates, and can also be coated to further control the release rates. The outer and lower portions 3420 and 3440 remain exposed, which allows for timed release of the active agents.

The outer portion 3420 retains the upper and lower portions 3430 and 3440 as a result of inwardly depending flange 3450. The flange 3450 provides a mechanical connection or lock to the upper and lower portions 3430 and 3440 and prevents them from sliding through the outer portion. The flange 3450 may circumscribe the entire inner opening 3425 of the outer portion 3420 or may be one or more projections that extend into the inner opening. The size and shape of flange 3450 can be chosen to facilitate assembly, as well as provide increased strength and regulate release. Assembly of product 3400 is facilitated by initial positioning of lower portion 3440 in inner opening 3425 of outer portion 3420, followed by moving the upper portion 3430 into position and then application of the adhesive or other bonding agent cap or label 3460 over, and sealing, the opening 3425. Alternatively, the label 3460 can partially cover or partially seal the opening 3425 to allow for release of the active agent in upper portion 3430. The label 3460 can be a layer of adhesive, bonding agent or the like that is positioned along the top of outer portion 3420 and upper portion 3430.

Figure 90:
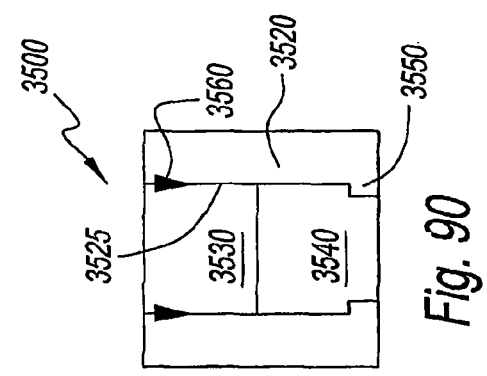
FIG. 90 is a cross-sectional view of a forty-second embodiment of a pharmaceutical product of the present invention.

Referring to FIG. 90, a forty-second embodiment of the pharmaceutical product is shown and generally referred to by reference numeral 3500. Product 3500 has an outer portion 3520, an upper portion 3530 and a lower portion 3540 that form three distinct components, which can be formed by tablet compression.

Similar to the components of the embodiments described above, the outer, upper and lower portions 3520, 3530 and 3540 are independently formulated to achieve a desired rate of release, e.g., a medium rate, a slow rate and an immediate rate, can include excipients to control the release rates, and can also be coated to further control the release rates. The upper and lower portions 3530 and 3540 remain exposed, which allows for timed release of all of the active agents.

The outer portion 3520 retains the upper and lower portions 3530 and 3540 as a result of inwardly depending flange 3550. The flange 3550 provides a mechanical connection or lock to the upper and lower portions 3530 and 3540 and prevents them from sliding through the outer portion. The flange 3550 may circumscribe the entire inner opening 3525 of the outer portion 3520 or may be one or more projections that extend into the inner opening. The size and shape of flange 3550 can be chosen to facilitate assembly, as well as provide increased strength and regulate release. Assembly of product 3500 is facilitated by initial positioning of lower portion 3540 in inner opening 3525 of outer portion 3520, followed by moving the upper portion 3530 into position. A locking ring 3560 is then actuated or sprung to hold the upper portion 3530 within the outer portion 3520. The means for actuation, springing or expansion can be via temperature change, chemical or other methods during the assembly process. The locking ring 3560 can be a single structure that circumscribes the entire inner opening 3525 or one or more smaller locking members.

Figure 91:
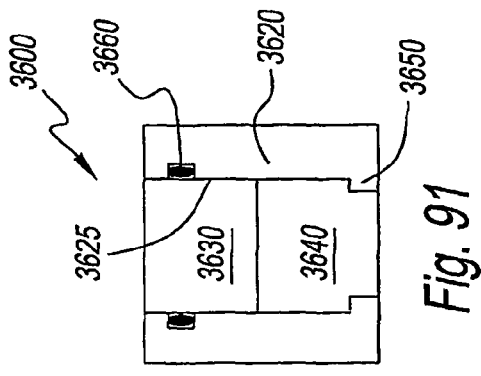
FIG. 91 is a cross-sectional view of a forty-third embodiment of a pharmaceutical product of the present invention.

Referring to FIG. 91, a forty-third embodiment of the pharmaceutical product is shown and generally referred to by reference numeral 3600. Product 3600 has an outer portion 3620, an upper portion 3630 and a lower portion 3640 that form three distinct components, which can be formed by tablet compression.

Similar to the components of the embodiments described above, the outer, upper and lower portions 3620, 3630 and 3640 are independently formulated to achieve a desired rate of release, e.g., a medium rate, a slow rate and an immediate rate, can include excipients to control the release rates, and can also be coated to further control the release rates. The upper and lower portions 3630 and 3640 remain exposed, which allows for timed release of all of the active agents.

The outer portion 3620 retains the upper and lower portions 3630 and 3640 as a result of inwardly depending flange 3650. The flange 3650 provides a mechanical connection or lock to the upper and lower portions 3630 and 3640 and prevents them from sliding through the outer portion. The flange 3650 may circumscribe the entire inner opening 3625 of the outer portion 3620 or may be one or more projections that extend into the inner opening. The size and shape of flange 3650 can be chosen to facilitate assembly, as well as provide increased strength and regulate release. Assembly of product 3600 is facilitated by initial positioning of lower portion 3640 in inner opening 3625 of outer portion 3620, followed by moving the upper portion 3630 into position. A friction ring 3660 is positioned along the inner surface of the outer portion 3620, which holds the upper portion 3630 within the outer portion via friction. The friction ring 3660 can be a single structure that circumscribes the entire inner opening 3625 or one or more smaller friction members.

Figure 92:
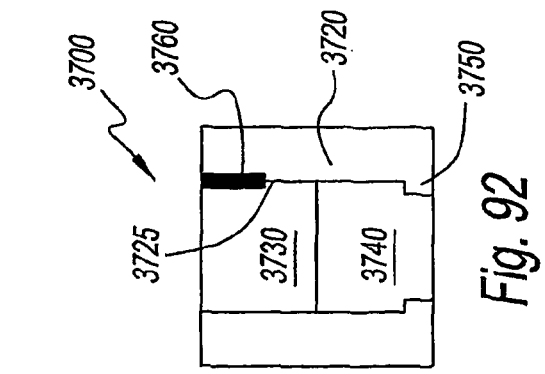
FIG. 92 is a cross-sectional view of a forty-fourth embodiment of a pharmaceutical product of the present invention.

Referring to FIG. 92, a forty-fourth embodiment of the pharmaceutical product is shown and generally referred to by reference numeral 3700. Product 3700 has an outer portion 3720, an upper portion 3730 and a lower portion 3740 that form three distinct components, which can be formed by tablet compression.

Similar to the components of the embodiments described above, the outer, upper and lower portions 3720, 3730 and 3740 are independently formulated to achieve a desired rate of release, e.g., a medium rate, a slow rate and an immediate rate, can include excipients to control the release rates, and can also be coated to further control the release rates. The upper and lower portions 3730 and 3740 remain exposed, which allows for timed release of all of the active agents.

The outer portion 3720 retains the upper and lower portions 3730 and 3740 as a result of inwardly depending flange 3750. The flange 3750 provides a mechanical connection or lock to the upper and lower portions 3730 and 3740 and prevents them from sliding through the outer portion. The flange 3750 may circumscribe the entire inner opening 3725 of the outer portion 3720 or may be one or more projections that extend into the inner opening. The size and shape of flange 3750 can be chosen to facilitate assembly, as well as provide increased strength and regulate release. Assembly of product 3700 is facilitated by initial positioning of lower portion 3740 in inner opening 3625 of outer portion 3720, followed by moving the upper portion 3630 into position. A locking stake 3760 is positioned along the inner surface of the outer portion 3720, which holds the upper portion 3730 within the outer portion.

Figure 93:
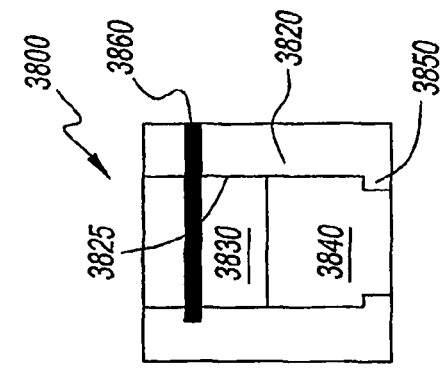
FIG. 93 is a cross-sectional view of a forty-fifth embodiment of a pharmaceutical product of the present invention.

Referring to FIG. 93, a forty-fifth embodiment of the pharmaceutical product is shown and generally referred to by reference numeral 3800. Product 3800 has an outer portion 3820, an upper portion 3830 and a lower portion 3840 that form three distinct components, which can be formed by tablet compression.

Similar to the components of the embodiments described above, the outer, upper and lower portions 3820, 3830 and 3840 are independently formulated to achieve a desired rate of release, e.g., a medium rate, a slow rate and an immediate rate, can include excipients to control the release rates, and can also be coated to further control the release rates. The upper and lower portions 3830 and 3840 remain exposed, which allows for timed release of all of the active agents.

The outer portion 3820 retains the upper and lower portions 3830 and 3840 as a result of inwardly depending flange 3850. The flange 3850 provides a mechanical connection or lock to the upper and lower portions 3830 and 3840 and prevents them from sliding through the outer portion. The flange 3850 may circumscribe the entire inner opening 3825 of the outer portion 3820 or may be one or more projections that extend into the inner opening. The size and shape of flange 3850 can be chosen to facilitate assembly, as well as provide increased strength and regulate release. Assembly of product 3800 is facilitated by initial positioning of lower portion 3840 in inner opening 3825 of outer portion 3820, followed by moving the upper portion 3830 into position. A roll-pin is inserted through the outer portion 3820 and through the upper portion 3830, which locks the upper portion in place.

Figure 94:
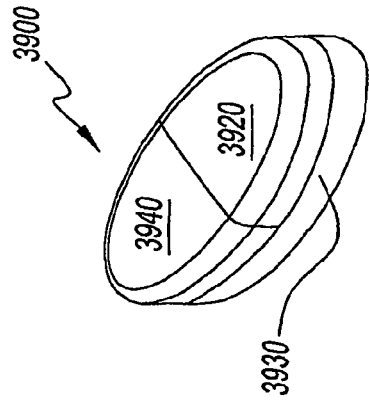
FIG. 94 is a perspective view of a forty-sixth embodiment of a pharmaceutical product of the present invention.

Referring to FIG. 94, a forty-sixth embodiment of the pharmaceutical product is shown and generally referred to by reference numeral 3900. Product 3900 has a first portion 3920, a second portion 3930 and a third portion 3940 that form three distinct components, which can be formed by tablet compression to have an ellipsoidal-like shape for ease of delivery.

Similar to the components of the embodiments described above, the first, second and third portions 3920, 3930 and 3940 are independently formulated to achieve a desired rate of release, e.g., a medium rate, a slow rate and an immediate rate, can include excipients to control the release rates, and can also be coated to further control the release rates. The first, second and third portions 3920, 3930 and 3940 all remain exposed, which allows for release of the active agent for all three of the portions.

Product 3900 provides for an adhesive bond between the first, second and third portions 3920, 3930 and 3940 along inner walls of each portion. To enhance the connection, additional connection methods, such as one of the bonding techniques described above, can also be used.

Referring to FIG. 95, a forty-seventh embodiment of the pharmaceutical product is shown and generally referred to by reference numeral 4000. Product 4000 has a first portion 4020, a second portion 4030 and a third portion 4040 that form three distinct components, which can be formed by tablet compression to have a cylindrical-like shape for ease of delivery.

Similar to the components of the embodiments described above, the first, second and third portions 4020, 4030 and 4040 are independently formulated to achieve a desired rate of release, e.g., a medium rate, a slow rate and an immediate rate, can include excipients to control the release rates, and can also be coated to further control the release rates. The first, second and third portions 4020, 4030 and 4040 all remain exposed, which allows for release of the active agent for all three of the portions.

Product 4000 provides for an adhesive bond between the first, second and third portions 4020, 4030 and 4040 along inner walls of each portion. To enhance the connection, additional connection methods, such as one of the bonding techniques described above, can also be used.

Referring to FIG. 96, a forty-eighth embodiment of the pharmaceutical product is shown and generally referred to by reference numeral 4100. Product 4100 has an upper portion 4120, a middle portion 4130 and a lower portion 4140 that form three distinct components, which can be formed by tablet compression.

Similar to the components of the embodiments described above, the upper, middle and lower portions 4120, 4130 and 4140 are independently formulated to achieve a desired rate of release, e.g., a medium rate, a slow rate and an immediate rate, can include excipients to control the release rates, and can also be coated to further control the release rates. The upper and lower portions 4120 and 4140 remain exposed, which allows for timed release of the active agents.

Product 4100 provides for an adhesive bond between the upper and lower portions 4120 and 4140 and the middle portion 4130. To enhance the strength of the connection, middle portion 4130 is formed as a biscuit that is inserted within corresponding openings in the upper and lower portions 4120 and 4140. To further enhance the connection, additional connection methods, such as one of the bonding techniques described above, can also be used.

Referring to FIG. 97, a forty-ninth embodiment of the pharmaceutical product is shown and generally referred to by reference numeral 4200. Product 4200 has an upper portion 4220, a middle portion 4230 and a lower portion 4240 that form three distinct components, which can be formed by tablet compression.

Similar to the components of the embodiments described above, the upper, middle and lower portions 4220, 4230 and 4240 are independently formulated to achieve a desired rate of release, e.g., a medium rate, a slow rate and an immediate rate, can include excipients to control the release rates, and can also be coated to further control the release rates. The upper, middle and lower portions 4220, 4230 and 4240 all remain exposed, which allows for release of the active agent for all three of the portions.

Product 4200 provides for an adhesive bond between the upper and lower portions 4220 and 4240 and the middle portion 4230. Middle portion 4230 is a capsule that is disposed within an inner opening 4225 of the upper and lower portions 4220 and 4240. To enhance the connection, additional connection methods, such as one of the bonding techniques described above, can also be used.

Referring to FIG. 98, a fiftieth embodiment of the pharmaceutical product is shown and generally referred to by reference numeral 4300. Product 4300 has an upper portion 4320, a middle portion 4330 and a lower portion 4340 that form distinct components, which can be formed by tablet compression.

Similar to the components of the embodiments described above, the middle portion 4330 is composed of distinct portions 4331, 4332 and 4333 that are independently formulated to achieve a desired rate of release, e.g., a medium rate, a slow rate and an immediate rate, can include excipients to control the release rates, and can also be coated to further control the release rates. The middle portion remains exposed, which allows for release of the active agent for all three of the portions.

Product 4300 provides for an adhesive bond between the upper and lower portions 4320 and 4340 and the middle portions 4331, 4332 and 4333. To enhance the connection, additional connection methods, such as one of the bonding techniques described above, can also be used. The middle portions can have diameters smaller than the diameters of upper and lower portions 4320 and 4340 to form a dumbbell-like shape or can have the same diameters to have a uniform diameter along the product 4300. The number of middle portions can also be varied.

Referring to FIG. 99, a fifty-first embodiment of the pharmaceutical product is shown and generally referred to by reference numeral 4400. Product 4400 has an upper portion 4420, a middle portion 4430 and a lower portion 4440 that form three distinct components, which can be formed by tablet compression.

Similar to the components of the embodiments described above, the upper, middle and lower portions 4420, 4430 and 4440 are independently formulated to achieve a desired rate of release, e.g., a medium rate, a slow rate and an immediate rate, can include excipients to control the release rates, and can also be coated to further control the release rates. The upper and lower portions 4420 and 4440 remain exposed, which allows for timed release of the active agents.

Product 4400 provides for an adhesive bond between the upper and lower portions 4420 and 4440 thereby encapsulating the middle portion 4430. To facilitate delivery the assembled product 4400 has a capsule-like shape. To enhance the connection, additional connection methods, such as one of the bonding techniques described above, can also be used.

The present invention contemplates a variety of binding approaches to be used with the applicable embodiments described above or alternatives thereof. In one embodiment the present invention contemplates use of micro-encapsulated water, micro-encapsulated adhesives, pressure sensitive adhesives, pressure sensitive films, rivets, capsule rivets, heat welding, ultrasonic welding, spin welding and/or infrared welding, alone or in combination with one another. In one embodiment the use of coating agents on the individual components, upon application of a solvent, such as water or water: alcohol may themselves act as an adhesive.

The embodiments described above, in particular those utilizing mechanical interlocking or a connection structure or a combination of bonding with a mechanical interlock or a connection structure, have the advantage of being assembled by various devices that are adapted for efficient assembly of the products. Such assembly devices can be remotely located, such as, for example, at a pharmacy or any establishment outside the original manufacturing facility of the individual components. Additionally, such devices can provide for efficient assembly of multiple products through various designs based upon the particular method or structure for connecting the multiple components of the product, such as, for example, a riveting assembly device.

The present disclosure contemplates the assembly of the embodiments described herein at least occurring by way of a large-scale production and assembly, a third-party assembly, a pharmacy assembly, such as, for example, through the use of cartridges, and by patient assembly, such as, for example, by hand. Exemplary embodiments that can be used for assembly of the products described herein and, in particular, for assembly of the preferred embodiments described herein are described in the following related application which has been filed contemporaneously herewith, and the disclosure of which is hereby incorporated by reference in its entirety: "METHOD AND MACHINE FOR PHARMACEUTICAL PRODUCT ASSEMBLY", U.S. patent application Ser. No. 11/601,023. Additionally, this application is related to the following co-pending applications, the disclosures of which are hereby incorporated by reference in their entirety: U.S. Provisional Application No. 60/629,876, filed Nov. 19, 2004 and U.S. Provisional Application No. 60/631,923, filed Nov. 30, 2004.

While most of the pharmaceutical products provide for three separate components, the present invention contemplates the use of any number of separate components that are interlocked to provide for a single delivery vehicle for a plurality of active agents, or one active agent in multiple release modes, or combinations thereof. It should be understood that the present invention is not limited by the type or form of active agent or the type or form of pharmaceutical or pharmaceutical-like product.

The pharmaceutical products of the present invention have particular interlocking shapes, which facilitate the assembly of the resulting single delivery entity or vehicle. However, the present invention contemplates the use of other interlocking shapes for the plurality of components, as well as other shapes of the resulting product, which allow for the delivery of a plurality of components in a single delivery vehicle, such as, for example, a screw structure. While the embodiments described herein show particular numbers of engaging structures or engaging members such as a single annular ring or two concentrically aligned annular rings, it should be understood that the present invention contemplates the use of other numbers of engaging structures or members.

The present invention also contemplates a delivery vehicle or entity having a plurality of components that are selectively connectable to each other, such as, for example, by releasable snap-fit or some other releasable connection. The present invention further contemplates a delivery vehicle or entity having a plurality of components that are selectively connected through use of a non-releasable connection, such as, for example, a non-releasable snap-fit.

The pharmaceutical products of the present invention can be assembled and connected by an automated interlocking process. However, the present invention contemplates the use of other methods of assembly, including manually. The binding or connection process, including the speed of the process, allows for the manufacture of the final dosage form at commercial processing rates. The compression process used in the formation of the pharmaceutical products, as well as the shapes generated, interlock in such a way that they preferably appear as one entity or delivery vehicle.

Functional coating for the pharmaceutical products herein may be provided for by use of various polymeric coatings which can loosely be divided into three categories: (1) water soluble polymers useful for rapid dissolve and immediate release of active agents, (2) water insoluble polymers useful for controlled release of the active agents; and (3) pH sensitive polymers for pulsatile or targeted release of active agents. It is recognized that combinations of all of these carriers may be used herein. It is also recognized that several of the commercially available poly(meth)acrylate polymers are pH dependent for the solubility and may fall into both categories. Most of these pharmaceutically acceptable polymers, as well as a number of other well known pharmaceutically acceptable coating agents, both for immediate release and controlled release are described in detail in the Handbook of Pharmaceutical excipients, published jointly by the American Pharmaceutical association and the Pharmaceutical society of Britain. Functional coatings may include sealing coatings, or top coatings, in addition to controlled release rate coatings.

Water soluble polymers generally include but are not limited to, poly(ethylene oxide), polyvinyl alcohol, polyvinyl pyrrolidone, hyaluronic acid, alginate, carragenen, cellulose derivatives such as carboxymethyl cellulose sodium, hydroxyethyl cellulose, hydroxypropylcellulose, hydroxypropylmethyl cellulose, hydroxypropylmethyl cellulose phthalate, cellulose acetate, cellulose acetate propionate, cellulose acetate phthalate, starch and its derivatives such as hydroxyethyl starch, sodium starch glycolate, dextrin, chitosan and its derivatives, albumen, zein, gelatin, and collagen.

Water insoluble polymers generally include but are not limited to, polyvinyl acetate, the celluloses and their derivatives, such as methyl cellulose, ethylcellulose, and cellulose acetate propionate, polyethylenes, and polyvinyl alcohol, noncrystalline cellulose, polyacrylate and its derivatives as well as the methacrylates and their derivatives, all included in the Eudragit family of polymers available from Rohm Pharma (Germany), poly(alpha-hydroxy acid) and its copolymers such as poly(α-caprolactone), poly(lactide-co-glycolide), poly(alpha-aminoacid) and its copolymers, poly (orthoester), polyphosphazenes, poly(phosphoester), and polyanhydride.

Additionally the functional coatings, which may be a film coat, and which may be applied by compression or spray drying, may act as a semi permeable barrier thereby allowing diffusion control of drug release by the water insoluble polymer, or a partially water-soluble polymer (acting as a release retarding coating). Alternatively the film coating may control the dissolution rate. Such film coating may, for example, be composed of polymers which are either substantially or completely impermeable to water or aqueous media (as noted above), or are slowly erodable in water or aqueous media or biological liquids and/or which swell in contact with water or aqueous media or biological liquids. Suitably the film coat should be such that it retains these characteristics at least until complete or substantially complete transfer of the active material content to the surrounding medium. Such film coated tablets are referred to as functional film coated tablets.

Film coats comprising polymers which swell in contact with water or aqueous media may swell to such an extent that the swollen layer forms a relatively large swollen mass, the size of which delays its immediate discharge from the stomach into the intestine. Film coats may typically have an individual thickness of 2 microns to 10 microns.

Suitable polymers for film coats which are relatively impermeable to water include hydroxypropyl methylcellulose polymers for example the Methocel® series of polymers mentioned above, for example Methocel K100M, Methocel K15M; the Eudragit® series of polymers, Aquacoat® and used singly or combined, or optionally combined with an Ethocel® polymer. Another polymer suitable for coating is SURELEASE® which is an aqueous ethylcellulose dispersion. This can be obtained from COLORCON a division of Berwind Pharmaceuticals Services, Inc. Additionally, a mixture of SURELEASE polymer or other suitable partially permeable polymer, and a pore forming material for example OPADRY (trade mark) clear (YS-2-7013), again obtainable from COLORCON, can be used. One suitable range of application is from about 3 to about 5% by weight of coating on a tablet.

The coating, if present, can optionally contain additional pharmaceutically acceptable excipients such as plasticizers, dyes, etc. One suitable plasticizer is hydrogenated castor oil may be combined with the coating polymer. The film coating may also include conventional binders, fillers, lubricants, colorants such as iron oxides or organic dyes and compression aids etc such as Polyvidon K30®, magnesium stearate, and silicon dioxide, e.g. Syloid 244®.

As noted herein the pharmaceutical products of the present invention may be prepared by compressing suitable ingredients (e.g. the pharmaceutical composition) to form a compacted mass, which comprises the core of the dosage form (also referred to herein as "tablet core" or "matrix"). This may be prepared using conventional tablet excipients and formulation compression methods. Thus, the core typically comprises the active agent or agents along with excipients that impart satisfactory processing and compression characteristics such as one or more diluents, binders, and/or lubricants. Additional excipients that may form part of the core of the device include one or more disintegrants, flavourants, sweeting agents, glidants, colorants, release modifying agents and/or solubilising agents such as surfactants, pH modifiers, and complexation vehicles, absorption enhancers, plasticizers, dissolution modifying agents, and processing aids. It is recognized that some of these excipients are suitably used for matrices which result from injection molding the components, or extrusion of the active agent, e.g. with a polymer or polymeric blend.

Typically the active agent and excipients are thoroughly mixed prior to compression into a solid core. The core of the device may be formed by standard, well known wet granulation or dry granulation methods, and then compressed, or alternatively by direct compression from the composition mixture.

The core may be produced according to any desired preselected shape such as bi-convex, biconcave, concave-convex, hemispherical, near hemi-spherical, round, oval, generally ellipsoidal, oblong, generally cylindrical or polyhedral, e.g. a triangular prism shape, and all of those as also described herein The core may be coated with a functional coating, and overcoating as described herein by any pharmaceutically acceptable coating method. Examples of such methods include coating methods such as disclosed in U.S. Pat. No. 5,004,614, film coating, sugar coating, spray coating, dip coating, compression coating, and electrostatic coating. Typical methods include spraying the coating onto the tablet core in a rotating pan coater or in a fluidised bed coater until the desired coating thickness is achieved.

As noted above, the pharmaceutical products are suitably manufactured through use of compression to form the individual components. However, the present invention contemplates formation of the different components by other methods as well, such as, for example, injection molding. Additionally, the components of a product can be formed by a combination of processes such as, for example, compression molding one component and injection molding another component.

By forming this multi-component tablet (e.g., two, three or more distinct components that form one multi-functional product), the final dosage form can have up to 4, or 6 or even more possible modes of release (and variations thereof where more components are being used) at the various stages of the gastrointestinal (GI) track. The pharmaceutical products are consumed as one entity and travel through the GI tract, with each component releasing the active agent at a desired point either through use of the core matrices alone, optionally in combination with a controlled release coating or a functional coating; the core composition in combination with excipients to produce a controlled release, modified release, or delayed release core, optionally in combination with functional coatings or controlled release coating agents, as deemed necessary or desirable. This allows for targeting of each of the desired sites of bio-availability, and controlling the rate of release of the different active agents.

For additional exemplification of the invention, a plurality of sub units, e.g. the individual solid sub-units may comprise the same or a different drug substance. Each sub-unit may contain the same drug substance but release the contents into the gastro-intestinal tract of the patient at a different rate, at different times after administration to the patient or at different places in the patient's gastro-intestinal system. Alternatively each sub-unit may contain a different drug substance, each of which may be released at the same or a different rate or time after administration or place in the patient's gastrointestinal system.

For example two or more sub-units may each contain different drug substances, and/or different drug substance formulations, and/or the same drug in different formulations, so that a combination of two or more drug substances or formulations may be administered to a patient. The dosage form of this invention enables the assembly together of these sub-units or individual components, which differ in their drug content and/or drug content release characteristics to provide a dosage form tailored to specific administration requirements.

The dimensions and shape of each of the sub-units and hence of the overall assembled dosage form may be determined by the nature and quantity of the material to be contained therein and the intended mode of administration and intended recipients. For example a dosage form intended for oral administration may be of a shape and size similar to that of known capsules intended for oral administration. The dosage form is particularly suitable for presentation as an oral dosage form containing one or more drug substances suitable for oral administration, and appears to be suitable for all types of such drug substance.

The sub-units may differ from each other in their drug content release characteristics, and this may be achieved in various ways as has been described herein. For example one or more solid sub-units may be substantially immediate release, i.e. releasing their drug contents substantially immediately upon ingestion or on reaching the stomach.

For example one or more solid sub-units may be sustained-release sub-units. For example one or more solid sub-units and/or capsule compartments may be pulsed-release sub-units for example releasing their drug content at a specific predetermined point in a patient's gastro-intestinal system. This may be achieved by the use of polymer materials which dissolve or disperse only at defined pH environments, such as the above mentioned polymers, or certain Eudragit® polymers, for instance Eudragit E100 which is acid labile.

It should be understood that features of one of the exemplary embodiments may be used with features of another exemplary embodiment. Also, the plurality of components are preferably solid so as to facilitate the interlocking connection and strength of the product.

In the alternative to compression of the desired tablet shapes, microcellular foam technology for the production of pharmaceutical tablets having the desired shapes, such as those described in WO 03/057197, published Jul. 17, 2003, whose disclosure is incorporated herein by reference may be used.

It should be noted that the terms "first", "second", "upper", "lower", "middle" and the like, are used herein to modify various elements. These modifiers do not necessarily imply a spatial, sequential, or hierarchical order to the modified elements unless specifically stated. It should be further understood that the embodiments described herein contain various features that the present invention contemplates can be interchangeable between the embodiments.

"Pharmaceutically acceptable agents", or "medicaments", or "actives" includes, but is not limited to, drugs, proteins, peptides, nucleic acids, nutritional agents, as described herein. This term includes therapeutic active agents, bioactive agents, active agents, therapeutic agents, therapeutic proteins, diagnostic agents, or drug(s) as defined herein, and follows the guidelines from the European Union Guide to Good Manufacturing Practice. Such substances are intended to furnish pharmacological activity or other direct effect in the diagnosis, cure, mitigation, treatment, or prevention of a disease or to affect the structure and function of the body. The substance may also include a diagnostic agent, such as an imaging agent and/or a radioactive labeled compound. Their use may be in a mammal, or may be in a human. The pharmacological activity may be prophylactic, or for treatment of a disease state. The agents herein include both small molecule therapeutics, as well as peptides and proteins. The pharmaceutical compositions described herein may optionally comprise one or more pharmaceutically acceptable active agent, bioactive agent, active agent, therapeutic agent, therapeutic protein, diagnostic agent, or drug(s) or ingredients distributed within. The person skilled in the art will appreciate that a therapeutically effective amount of the active agent will depend on the patient's age, size, severity of disease and other medication.

As used herein the term's "pharmaceutically acceptable active agent", "pharmaceutically active agent", "active agent", drug moiety" or "drug" are used interchangeably.

Water solubility of an active agent is defined by the United States Pharmacoepia. Therefore, active agents which meet the criteria of very soluble, freely soluble, soluble and sparingly soluble as defined therein are encompassed this invention.

Many active pharmaceutical agents, including drugs and prodrugs, have been formulated as orally deliverable dosage forms providing sustained release (SR) (otherwise known as slow release, extended release or modified release (MR)) of such agents over a period of time effective to permit once daily administration. A well-known system for formulating such dosage forms involves a matrix comprising a hydrophilic polymer wherein the agent is dispersed; the agent is released over a period of time in the gastrointestinal tract upon dissolution, or erosion of the matrix. Sustained-release dosage forms comprising such a matrix system are conveniently prepared as compressed tablets, also described herein as "matrix tablets".

As used herein, the term "sustained release" or "modified release" refers to the gradual but continuous release over any extended period of an active agent after oral ingestion, in contrast to a release which is pulsed or delayed to deliver at different points in time, or within the GI tract at particular discrete points. For SR or MR release, the release starts when the formulation reaches the stomach and starts to disintegrate/swell/dissolve/erode. The release will continue over a period of time and may continue throughout the small intestine and after the formulation reaches the large intestine. A delayed release will typically provide a point in the GI tract other than the stomach where the active agent is released. In a pulse system, more than one discrete pulse or release of the active agent is seen, such as formulations produced by Advances or Flamel. These delayed or pulse system typically occur when the pH changes, such as from the stomach to the small intestines allowing the coating agents to be removed and release the active agent, alternatively over a period of time the functional or release coating will degrade to release the active agent. Other art recognized techniques to produce delayed or pulsed release of active agents are known and encompassed within the scope of this invention.

It is recognized that the Figures use the term "as a controlled rate of release, such as a slow-rate, or a medium-rate of release, or an immediate-rate of release." The immediate-rate of release is a standard, immediate (IR) dissolution/disintegration and release of the active agent from the core matrix. The terms slow-rate or medium rate of release are merely illustrative of the controlled release, modified release or delayed release dissolution and disintegration of the core matrix as compared to an immediate release of the same active from an IR core tablet the use of slow or medium rate are meant to designate differing rates of release of an active or multiple actives from a multi-component dosage form and are not meant as a limitation on the figure embodiments. As noted herein, all of the individual components contained within a solid multicomponent dosage form herein may all be IR release, all controlled release, all modified release, all delayed release or all pulse release, or used in any combination thereof including with a placebo component.

When used herein "substantially all" means more than 85%, preferably more than 90%.

Suitable drug substances can be selected from a variety of known classes of drugs including, but not limited to, analgesics, anti-inflammatory agents, anthelmintics, anti-arrhythmic agents, antibiotics (including penicillin's), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, PDE IV inhibitors, NK3 inhibitors, ppar agents, NK-2 inhibitors, CSBP/RK/p38 inhibitors, antipsychotics, vasodilators and xanthines.

A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference in its entirety. The drug substances are commercially available and/or can be prepared by techniques known in the art.

The components are generally described as having active agents, but could be formed without an active agent, e.g., a placebo, to complete the geometry or structure of the product. Additionally, the products described herein are referred to generally as pharmaceutical and/or pharmaceutical-like products but are also intended to include nutraceuticals, medical foods, vitamins, minerals, OTC medications, veterinarian products, personalized sports nutrition, personalized medicine, micro ingredients and/or nutritional products.

All publications, including but not limited to patents and patent applications, cited in this specification are herein incorporated by reference as if each individual publication were specifically and individually indicated to be incorporated by reference herein as though fully set forth.

The present invention having been thus described with particular reference to the preferred forms thereof, it will be obvious that various changes and modifications may be made therein without departing from the spirit and scope of the present invention as defined herein.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the examples herein are to be construed as merely illustrative and not a limitation of the scope of the present invention in any way. The embodiments of the invention in which an exclusive property or privilege is claimed are defined as follows.

What is claimed is:

1. A method of producing a pharmaceutical product, the method comprising:
    independently forming at least three solid tablets by individually compressing a granulate mixture of at least one tablet excipient to form each of said at least three solid tablets, wherein at least two of said at least three solid tablets comprise an active agent; and
    assembling said at least three solid tablets into a single delivery vehicle,
    wherein said at least three solid tablets are an upper component, a lower component, and a one or more middle components between said upper and lower components in said single delivery vehicle, wherein said upper component and said lower component each has an inner surface, wherein each inner surface is comprised of a recess and/or projection, wherein the inner surfaces of said upper and lower components are mirror images of each other, and wherein said one or more middle components fits between said upper and said lower components.

2. The method of claim 1, further comprising coating at least one of said at least three solid tablets.

3. The method of claim 1, wherein said at least three solid tablets are assembled so that they are interlocked with a mechanical connection in said single delivery vehicle.

4. The method of claim 1, wherein at least three solid tablets are assembled so that they are interlocked via a connection method selected from the group consisting of a locking pin mechanism, a snap-fit, a screw-fit, an injection molded locking pin, banding, shrink wrapping, injection mold gluing, lasers, microwaves, heat, compression, ultrasonic welding, thermal welding, and any combinations thereof.

5. The method of claim 1, wherein said at least three solid tablets are assembled into said single delivery vehicle by applying an adhesive to at least one of said at least three solid tablets and pressing said at least three solid tablets together to form said single delivery vehicle.

6. The method of claim 1, wherein said one or more middle components has a shape selected from the group consisting of oval, round, and rectangular.

7. A method of producing a pharmaceutical product, the method comprising:
    independently forming an upper solid tablet by compressing a granulate mixture of at least one tablet excipient and an orally ingestible pharmaceutically active agent so that said upper solid tablet has a first recess that extends to an outer edge of said upper solid tablet;
    independently forming a lower solid tablet by compressing a granulate mixture of at least one tablet excipient and an orally ingestible pharmaceutically active agent so that said lower solid tablet has a second recess that extends to an outer edge of said lower solid tablet;
    independently forming a one or more middle solid tablets by compressing a granulate mixture of at least one tablet excipient and an at least one orally ingestible pharmaceutically active agent so that said one or more middle solid tablets has a desired shape, wherein said first and second recesses conform to said desired shape; and
    assembling an at least three layer pharmaceutical product by placing said one or more middle solid tablets into said first and second recesses of said upper and lower solid tablets, respectively, to form a single delivery vehicle with edges of said one or more middle solid tablets being exposed at said first and second recesses.

8. The method of claim 7, wherein said desired shape is selected from the group consisting of oval, round, and rectangular.

9. The method of claim 7, further comprising coating at least one of said upper, said one or more middle, and said lower solid tablets.

10. The method of claim 7, wherein said assembling step further comprises interlocking said one or more middle solid tablets into said first and second recesses of said upper and lower solid tablets, respectively, with a mechanical connection.

11. The method of claim 7, wherein said assembling step further comprises applying an adhesive to at least one of said upper, said one or more middle, and said lower solid tablets.

12. A method of producing a pharmaceutical product, the method comprising:
    independently forming at least three solid tablets by individually compressing a granulate mixture of at least one tablet excipient to form each of said at least three solid tablets, wherein at least two of said at least three solid tablets comprise an active agent; and
    assembling said at least three solid tablets into a single delivery vehicle;

wherein said at least three solid tablets are an upper component, a lower component, and one or more middle components between said upper and lower components in said single delivery vehicle, wherein said upper component and said lower component each has an inner surface, wherein each inner surface has a plurality of recesses and/or projections, wherein the inner surfaces of said upper and lower components are complementary images of each other, and wherein said one or more middle components fits between said complementary images of the inner surfaces of said upper and said lower components.

13. The method of claim 1, wherein the surface of said one or more middle components is complementary to the inner surfaces of said upper and said lower components.

14. The method of claim 12, wherein the surface of said one or more middle components is complementary to the inner surfaces of said upper and said lower components.

15. The method of claim 1, wherein the said upper component, said lower component and said one or more middle components have interlocking shapes providing non-releasable connections between said upper component, said lower component and said one or more middle components.

16. The method of claim 7, wherein the said upper component, said lower component and said one or more middle components have interlocking shapes providing non-releasable connections between said upper component, said lower component and said one or more middle components.

17. The method of claim 12, wherein the said upper component, said lower component and said one or more middle components have interlocking shapes providing non-releasable connections between said upper component, said lower component and said one or more middle components.

* * * * *